US011814659B2

(12) United States Patent
Stephanopoulos et al.

(10) Patent No.: US 11,814,659 B2
(45) Date of Patent: Nov. 14, 2023

(54) TUNABLE NANOSCALE CAGES FROM SELF-ASSEMBLING DNA AND PROTEIN BUILDING BLOCKS

(71) Applicants: Nicholas Stephanopoulos, Scottsdale, AZ (US); Yang Xu, Chandler, AZ (US)

(72) Inventors: Nicholas Stephanopoulos, Scottsdale, AZ (US); Yang Xu, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 782 days.

(21) Appl. No.: 16/816,029

(22) Filed: Mar. 11, 2020

(65) Prior Publication Data

US 2020/0289658 A1    Sep. 17, 2020

Related U.S. Application Data

(60) Provisional application No. 62/816,729, filed on Mar. 11, 2019.

(51) Int. Cl.
*C12N 9/88* (2006.01)
*C07K 19/00* (2006.01)
*B82Y 5/00* (2011.01)
*C12N 15/11* (2006.01)

(52) U.S. Cl.
CPC .............. *C12N 9/88* (2013.01); *B82Y 5/00* (2013.01); *C07K 19/00* (2013.01); *C12N 15/11* (2013.01); *C12Y 401/02014* (2013.01)

(58) Field of Classification Search
CPC . C12N 9/88; C12N 15/11; C12N 9/96; B82Y 5/00; B82Y 30/00; B82Y 40/00; C07K 19/00; C12Y 401/02014; C12Q 1/68; A61K 47/549; A61K 47/62; A61K 47/6949
See application file for complete search history.

(56) References Cited

U.S. PATENT DOCUMENTS

| 10,669,534 B2 * | 6/2020 | Fu ........................... C12N 9/96 |
| 2020/0140911 A1 | 5/2020 | Stephanopoulos et al. |
| 2020/0386750 A1 | 12/2020 | Green et al. |
| 2020/0390814 A1 * | 12/2020 | Yan ..................... A61K 47/6921 |

FOREIGN PATENT DOCUMENTS

WO    2020257690 A1    12/2020

OTHER PUBLICATIONS

Patterson et al., Evaluation of a symmetry-based strategy for assembling protein complexes. RSC Adv., 2011, vol. 1: 1004-1012. (Year: 2011).*
Xu et al., Tunable Nanoscale Cages from Self-Assembling DNA and Protein Building Blocks. ACS Nano., 2019, vol. 13: 3545-3554. (Year: 2019).*
Lou et al., Peptide-oligonucleotide conjugates as nanoscale building blocks for assembly of an artificial three-helix protein mimic. Nat. Comunn., 2016, vol. 7:12994, pp. 1-9. (Year: 2016).*
MacCulloch et al., Emerging applications of peptide-oligonucleotide conjugates: bioactive scaffolds, self-assembling systems, and hybrid nanomaterials. Org. Biomol. Chem., 2019, vol. 17: 1668-1682. (Year: 2019).*
Sadowski, J. P.; et al., Developmental Self-Assembly of a DNA Tetrahedron. Acs Nano 2014, 8 (4), 3251-3259.
Seiler, C. Y.; et al. Nucleic Acids Res 2014, 42, (Database issue), D1253-60.
Shi, X. L.; et al., Programmable DNA tile self-assembly using a hierarchical sub-tile strategy. Nanotechnology 2014, 25 (7).
Simmons, C. R.; et al., Size-Selective Incorporation of DNA Nanocages into Nanoporous Antimony-Doped Tin Oxide Materials. Acs Nano 2011, 5 (7), 6060-6068.
Stephanopoulos et al. "Bioactive DNA-peptide nanotubes enhance the differentitation of neural stem cells into neurons," Nano Letters, 2015, 15(1), 603-9.
Stephanopoulos, N. et al. "Immobilization and one-dimensional arrangement of virus capsids with nanoscale precision using DNA origami." Nano letters 10.7 (2010): 2714-2720.
Stephanopoulos, N., et al., Choosing an effective protein bioconjugation strategy, Natural Chemical Biology, 2011, 7:876.
Stephanopoulos, N.; et al. Nanoscale integration of sensitizing chromophores and porphyrins with bacteriophage MS2. Angew. Chem. Int. Ed. Engl. 48, 9498-9502 (2009).
Stephanopoulos, N., et al. Dual-surface modified virus capsids for targeted delivery of photodynamic agents to cancer cells. ACS Nano 4, 6014-6020 (2010).
Sun, W.; et al., Casting inorganic structures with DNA molds. Science 2014, 346 (6210), 717.
Trinh, T.; et al., DNA-imprinted polymer nanoparticles with monodispersity and prescribed DNA-strand patterns. Nature Chemistry 2018, 10 (2), 184-192.
Walls, A. C.; et al., Cryo-electron microscopy structure of a coronavirus spike glycoprotein trimer. Nature 2016, 531 (7592), 114.
Walsh, A. S.; et al., DNA Cage Delivery to Mammalian Cells. Acs Nano 2011, 5 (7), 5427-5432.
Wang, P. F.; et al., Retrosynthetic Analysis-Guided Breaking Tile Symmetry for the Assembly of Complex DNA Nanostructures. Journal of the American Chemical Society 2016, 138 (41), 13579-13585.
Wang, S.; et al., Simultaneous Imaging of Three Tumor-Related mRNAs in Living Cells with a DNA Tetrahedron-Based Multicolor Nanoprobe. Acs Sensors 2017, 2 (6), 735-739.
Wilks, T. R.; et al., "Giant Surfactants" Created by the Fast and Efficient Functionalization of a DNA Tetrahedron with a Temperature-Responsive Polymer. Acs Nano 2013, 7 (10), 8561-8572.

(Continued)

*Primary Examiner* — Ganapathirama Raghu
(74) *Attorney, Agent, or Firm* — Quarles & Brady, LLP

(57) ABSTRACT

Described herein are polyhedral, three-dimensional tunable nanocages assembled with a multimeric protein covalently linked to a polynucleotide handle and a DNA origami base assembly including sequences complementary to the polynucleotide handles, wherein the polynucleotide handle and the complementary sequences hybridize to for double-stranded DNA helices.

6 Claims, 31 Drawing Sheets
(28 of 31 Drawing Sheet(s) Filed in Color)

Specification includes a Sequence Listing.

(56) References Cited

OTHER PUBLICATIONS

Yan, X. et al., "Antibody-Bridged Beacon for Homogeneous Detection of Small Molecules", Analytical Chemistry, Aug. 2018, vol. 90, pp. 9667-9672 DOI:10.1021/acs.analchem.8b02510.

Zhang, F.; et al., Complex wireframe DNA origami nanostructures with multi-arm junction vertices. Nature Nanotechnology 2015, 10 (9), 779.

Zhao, Z.; et al., Nanocaged enzymes with enhanced catalytic activity and increased stability against protease digestion. Nature Communications 2016, 7.

Zlotnick, A.; et al., Mechanism of capsid assembly for an icosahedral plant virus. Virology 2000, 277 (2), 450-456.

Aldaye, F. A.; et al., Modular access to structurally switchable 3D discrete DNA assemblies. Journal of the American Chemical Society 2007, 129 (44), 13376.

Bai, X. C.; et al., Cryo-EM structure of a 3D DNA-origami object. Proceedings of the National Academy of Sciences of the United States of America 2012, 109 (49), 20012-20017.

Bale, J. B.; et al., Accurate design of megadalton-scale two-component icosahedral protein complexes. Science 2016, 353 (6297), 389-394.

Baskin, J. M.; et al., Copper-free click chemistry for dynamic in vivo imaging. Proceedings of the National Academy of Sciences of the United States of America 2007, 104 (43), 16793-16797.

Benson, E.; et al., DNA rendering of polyhedral meshes at the nanoscale. Nature 2015, 523 (7561), 441-U139.

Bhatia, D.; et al., Quantum dot-loaded monofunctionalized DNA icosahedra for single-particle tracking of endocytic pathways. Nature Nanotechnology 2016, 11 (12), 1112-1119.

Bruun, T. U. J.; et al., Engineering a Rugged Nanoscaffold To Enhance Plug-and-Display Vaccination. Acs Nano 2018, 12(9), 8855-8866.

Chen, J. H.; et al., Synthesis From DNA of a Molecule with the Connectivity of a Cube. Nature 1991, 350(6319), 631-633.

Chidchob, P.; et al., Synergy of Two Assembly Languages in DNA Nanostructures: Self-Assembly of Sequence-Defined Polymers on DNA Cages. Journal of the American Chemical Society 2016, 138 (13), 4416-4425.

Chin, J. W.; et al., Addition of p-azido-L-phenylaianine to the genetic code of *Escherichia coli*. Journal of the American Chemical Society 2002, 124 (31), 9026-9027.

Cormier, C. Y., et al. "PSI: Biology-materials repository: a biologist's resource for protein expression plasmids." Journal of structural and functional genomics 12.2 (2011): 55-62.

Das, R.; et al., Macromolecular modeling with Rosetta. Annual Review of Biochemistry 2008, 77, 363-382.

Dedeo, M. T.; et al., Viral Capsids as Self-Assembling Templates for New Materials. Molecular Assembly in Natural and Engineered Systems, vol. 103 2011, 103, 353-392.

Ding et al. "Gold nanoparticle self-similar chain structure organized by DNA origami," Journal of the American Chemical Society, 2010, 132(10), 3248.

Douglas, S. M.; et al., Self-assembly of DNA into nanoscale three-dimensional shapes. Nature 2009, 459 (7245), 414-418.

Douglas, S. M.; et al., Rapid prototyping of 3D DNA-origami shapes with caDNAno. Nucleic Acids Research 2009, 37 (15), 5001-5006.

Dutta et al. "A DNA-directed light-barvesting/reaction center system," Journal of the American Chemical Society, 2014, 136(47), 16618-16625.

Edwardson, T. G. W.; et al., Site-specific positioning of dendritic alkyl chains on DNA cages enables their geometry-dependent self-assembly. Nature Chemistry 2013, 5 (10), 868-875.

Flory, J. et al., "Low Temperature Assembly of Functional 3D DNA-PNA-ProteinComplexes", Journal of the American Chemical Society, May 2014, vol. 136, pp. 8283-8295 10.1021/ja501228c.

Flory, J. et al., "Purification and assembly of thermostable Cy5labeled ?-PNAs into a 3D DNA nanocage", Artificial DNA: PNA & XNA, Sep.-Dec. 2014, vol. 5, No. 3, article e992181, 8 pages DOI:10.4161/1949095X.2014.992181.

Freeman, R.; et al., Instructing cells with programmable peptide DNA hybrids. Nature Communications 2017, 8.

Fullerton, S. W. B.; et al., Mechanism of the Class IKDPG aldolase. Bioorganic & Medicinal Chemistry 2006, 14 (9), 3002-3010.

Gilmore, J.M., et al. N-terminal protein modification through a biomimetic transamination reaction. Angew. Chem. Int. Ed. Engl. 45, 5307-5311 (2006).

Goodman, R. P., et al. "Rapid chiral assembly of rigid DNA building blocks for molecular nanofabrication." Science 310.5754 (2005): 1661-1665.

Hahn, J.; et al., Addressing the Instability of DNA Nanostructures in Tissue Culture. Acs Nano 2014, 8 (9), 8765-8775.

Halldorsson, S.; et al., Shielding and activation of a viral membrane fusion protein. Nature Communications 2018, 9.

Han, D.; et al., DNA Origami with Complex Curvatures in Three-Dimensional Space. Science 2011, 332 (6027), 342-346.

He, L.; et al., Fluorescence Resonance Energy Transfer-Based DNA Tetrahedron Nanotweezer for Highly Reliable Detection of Tumor-Related mRNA in Living Cells. Acs Nano 2017, 11 (4), 4060-4066.

He, Y.; et al., Hierarchical self-assembly of DNA into symmetric supramolecular polyhedra. Nature 2008, 452 (7184), 198-U41.

Hou, C. et al., "Supramolecular Protein Assemblies Based on DNA Templates", Physical Chemistry Letters, Aug. 2017, pp. 8, No. 3970-3979 DOI:10.1021/acs.jpclett.7b01564.

Hsia et al. "Design of a hyperstable 60-subunit protein icosahedron," Nature 2016, 535 (7610), 136.

Huang, P. S.; et al., The coming of age of de novo protein design. Nature 2016, 537 (7620), 320-327.

Jiang, S. X.; et al., Understanding the Elementary Steps in DNA Tile-Based Self-Assembly. Acs Nano 2017, 11 (9), 9370-9381.

Kashiwagi, D.; et al., Protein Nanotube Selectively Cleavable with DNA: Supramolecular Polymerization of "DNA-Appended Molecular Chaperones". Journal of the American Chemical Society 2018, 140 (1), 26-29.

Ke, Y.; et al., Three-Dimensional Structures Self-Assembled from DNA Bricks. Science 2012, 338 (6111), 1177-1183.

King, N. P.; et al., Accurate design of co-assembling multi-component protein nanomaterials. Nature 2014, 510 (7503), 103.

Kirchdoerfer, R. N.; et al., Pre-fusion structure of a human coronavirus spike protein. Nature 2016, 531 (7592), 118-121.

Lee, H. et al., Molecularly self-assembled nucleic acid nanoparticles for targeted in vivo siRNA delivery. Nature Nanotechnology 2012, 7 (6), 389-393.

Li, Z.; et al., A Replicable Tetrahedral Nanostructure Self-Assembled from a Single DNA Strand. Journal of the American Chemical Society 2009, 131 (36), 13093-13098.

Liu, C. C.; et al., Adding New Chemistries to the Genetic Code. Annual Review of Biochemistry, vol. 79 2010, 79, 413-444.

Liu, X. T.; et al., A dual-targeting DNA tetrahedron nanocarrier for breast cancer cell imaging and drug delivery. Talanta 2018, 179, 356-363.

Lu, N.; et al., Charge Transport within a Three-Dimensional DNA Nanostructure Framework. Journal of the American Chemical Society 2012, 134 (32), 13148-13151.

Marth, G.; et al., Precision Templated Bottom-Up Multiprotein Nanoassembly through Defined Click Chemistry Linkage to DNA. Acs Nano 2017, 11 (5), 5003-5010.

Martin, T. G.; et al., Design of a molecular support for cryo-EM structure determination. Proceedings of the National Academy of Sciences of the United States of America 2016, 113 (47), E7456-E7463.

Mavridis, I. M.; et al., Structure of 2-Keto-3-Deoxy-6-Phosphogluconate Aldolase at 2.8 a Resolution. Journal of Molecular Biology 1982, 162 (2), 419-444.

McMillan, J. R.; et al., DNA-Functionalized, Bivalent Proteins. Journal of the American Chemical Society 2018, 140 (22), 6776-6779.

Mei, Q. A.; et al., Stability of DNA Origami Nanoarrays in Cell Lysate. Nano Letters 2011, 11 (4), 1477-1482.

(56) References Cited

OTHER PUBLICATIONS

Miller, R. A.; et al., Self-assembling light-harvesting systems from synthetically modified tobacco mosaic virus coat proteins. Journal of the American Chemical Society 2007, 129 (11), 3104-3109.

Patterson et al. "Evaluation of a symmetry-based strategy for assembling protein complexes," Rsc Advances, 2011, 1 (6), 1004-1012.

Rothemund "Folding DNA to create nanoscale shapes and patterns," Nature, 440, 297-302, 2006.

* cited by examiner

FIGS. 7A-7E CONTINUED
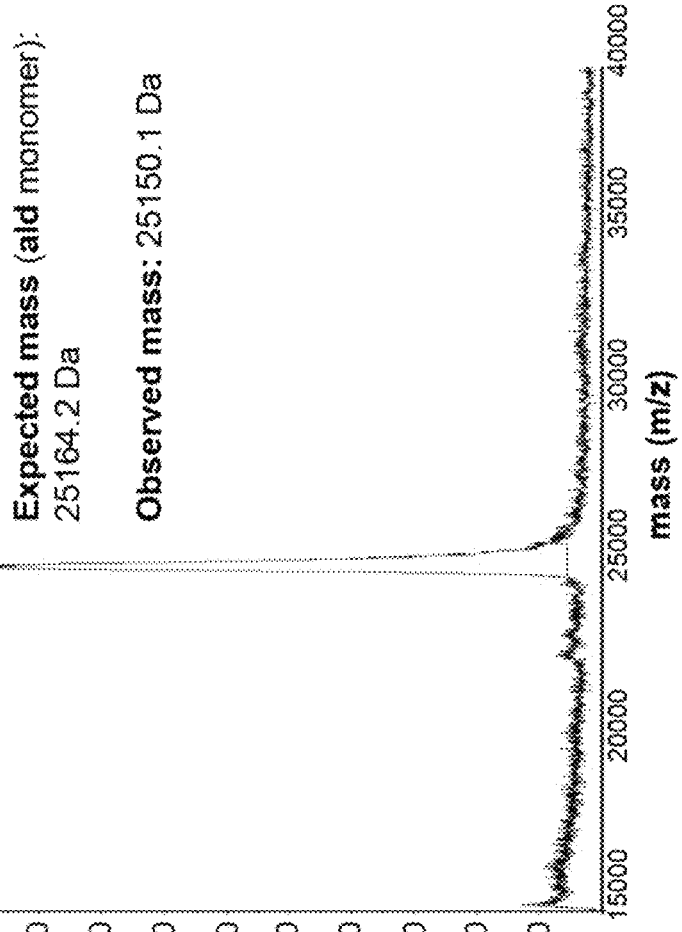
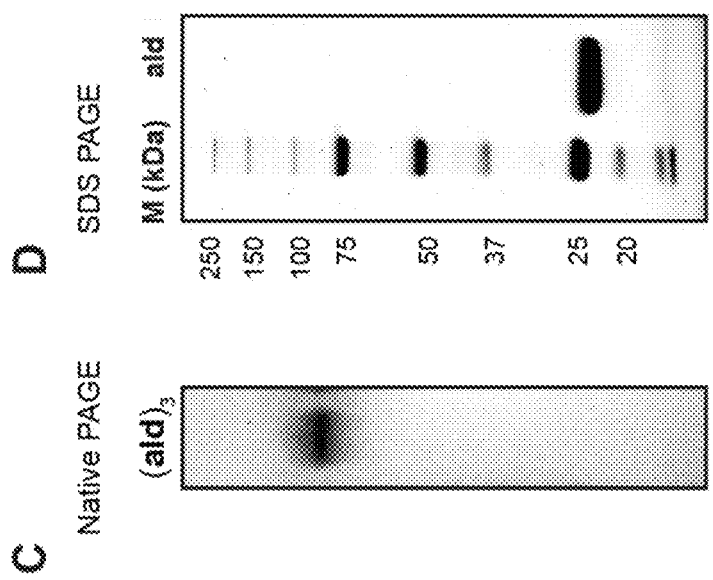

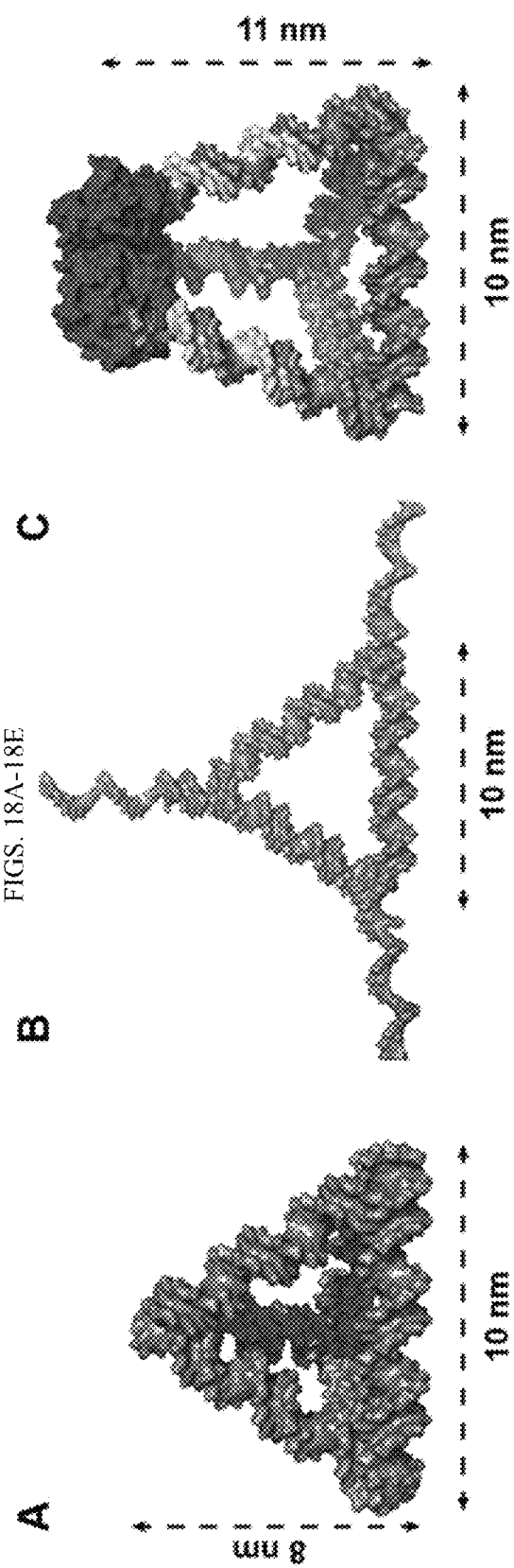
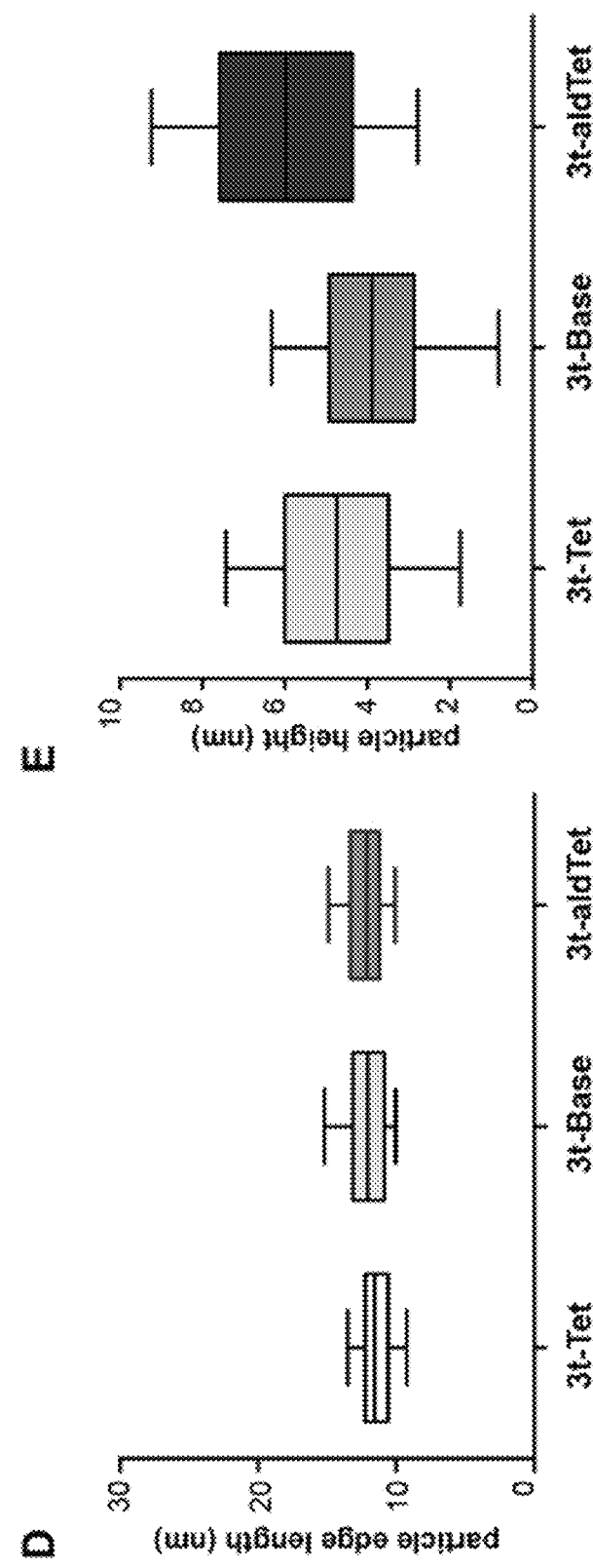
FIGS. 18A-18E

TUNABLE NANOSCALE CAGES FROM SELF-ASSEMBLING DNA AND PROTEIN BUILDING BLOCKS

CROSS-REFERENCE TO RELATED APPLICATIONS

This application claims priority to U.S. Provisional Application No. 62/816,729, filed Mar. 11, 2019, which is incorporated herein by reference in its entirety.

STATEMENT REGARDING FEDERALLY SPONSORED RESEARCH

This invention was made with government support under FA9550-17-1-0053 awarded by the Air Force Office of Scientific Research (AFOSR). The government has certain rights in the invention.

REFERENCE TO A SEQUENCE LISTING SUBMITTED VIA EFS-WEB

The content of the ASCII text file of the sequence listing named "112624_01182_ST25.txt" which is 19.3 kb in size was created on Mar. 9, 2020 and electronically submitted via EFS-Web herewith the application is incorporated herein by reference in its entirety.

BACKGROUND

Three-dimensional (3D) cages are one of the most important targets for nanotechnology, with applications including transporting cargo for imaging or drug delivery, confining catalysts in nanoscale reactors, positioning chemical elements to mimic photosynthesis, and serving as programmable "molds" or amphiphiles for polymeric or inorganic nanoparticle synthesis and encapsulation. Viruses like MS2 or CPMV represent one of nature's solutions to biomolecular nano-cages, with multiple protein components self-assembling in a highly symmetrical fashion to form a closed-shell structure. Viral capsids have been employed extensively as nano-scale scaffolds for diverse applications but have the disadvantage of being limited to naturally-occurring structures and symmetries. Inspired by viral capsids, there has been extensive research in the re-design of non-assembling protein components to form self-assembled cages. For example, naturally oligomeric proteins have been engineered (often with the aid of software like Rosetta) to self-assemble into highly symmetric structures such as tetrahedral, and megadalton scale cages. This elegant approach yields biologically relevant and often highly stable assemblies, but can require technical expertise in protein design that is challenging for the non-expert. Furthermore, tuning the nano-cage parameters (such as the size and volume) usually requires re-engineering the system with new protein building blocks, and it can be difficult to build highly anisotropic or asymmetrically-modified structures.

As an alternative approach, DNA has been used as a building block to construct well-defined cages through the programmable assembly of individual strands by Watson-Crick pairing. A wealth of 3D structures have been reported, with designs using wireframe, tile-based, and densely packed arrangements of DNA helices. These nano-cages are tunable in both geometry and size, and can be functionalized by modifying the individually addressable, unique component strands. Furthermore, software such as Cadnano and the low-cost availability of oligonucleotides from commercial suppliers results in easier access for the non-expert. This flexibility and accessibility comes at the expense of chemical homogeneity, where the final DNA nanostructures are restricted to the physical and chemical properties of the DNA duplex. As a result, DNA cages must be further elaborated with receptor-binding peptides or proteins to imbue them with bioactivity, and many structures require supra-physiological concentrations of magnesium for stability.

A need exists in the art for development of additional nanocage scaffolds with improved tenability and improved functionality.

SUMMARY OF THE DISCLOSURE

In a first aspect, provided herein is a three-dimensional nanocage comprising a protein covalently linked to a polynucleotide handle and a DNA assembly comprising a polynucleotide arm complementary to the polynucleotide handle linked to the protein, wherein the polynucleotide handle and the polynucleotide arm form a double-stranded complex linked to the protein to the DNA assembly. In some embodiments, the protein is a multimeric protein. In some embodiments, each monomer of the multimeric protein is covalently linked to a polynucleotide handle. In some embodiments, the protein is selected from the group consisting of a homotrimer, a homotetramer, a homopentamer, a homohexamer, a homoheptamer, a homooctamer, a homononamer, a homodecamer, a homoundecamer, and a homododecamer.

In some embodiments, the polynucleotide handle is covalently linked to a cysteine by a disulfide linkage. In some embodiments, the polynucleotide handle is covalently linked to a 4-azidophenylalanine residue.

In some embodiments, the DNA assembly comprises at least 4 oligonucleotides. In some embodiments, the DNA assembly comprises at least 5 oligonucleotides. In some embodiments, the polynucleotide handle is at least 15 base pairs long. In some embodiments, the protein is a homotrimer and the DNA assembly comprises 4 oligonucleotides.

In some embodiments, a three-dimensional nanocage described herein additionally comprising a payload molecule. In some embodiments, the payload molecule is selected from the group consisting of a nucleic acid, a polypeptide, a protein, an enzyme, an antibody, a phospholipid, a carbohydrate, and a polysaccharide.

In a second aspect, provided herein is a polyhedral nanocage comprising a multimeric protein, wherein each monomer of the multimeric protein is covalently linked to a polynucleotide handle and a DNA assembly of at least 4 oligonucleotides comprising a polynucleotide arm complementary to the polynucleotide handle, wherein the polynucleotide handle and the polynucleotide arm are hybridized to form a double stranded DNA helix linking the multimeric protein to the DNA assembly. In some embodiments, the polynucleotide handle is covalently linked to a solvent exposed cysteine residue by a disulfide linkage. In some embodiments, the multimeric protein comprises a 4-azidophenylalanine residue. In some embodiments, the polynucleotide handle is covalently linked to the 4-azidophenylalanine residue. In some embodiments, each oligonucleotide of the DNA assembly is at least 15 base pairs long. In some embodiments, each oligonucleotide of the DNA assembly is at least 21 base pairs long.

In some embodiments, the polyhedral nanocage described herein additionally comprising a payload.

In some embodiments, the multimeric protein is scaffold for the attachment of a small molecule, a targeting peptide, an antibody, or a fusion protein.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 1A shows modification of a homotrimer aldolase (ald$_3$) protein building block at a uniquely reactive residue with ssDNA handles. FIG. 1B shows self-assembly of four unique DNA strands to yield a triangular base with three complementary handles to the protein. FIG. 1C shows annealing of the protein-DNA conjugate and triangular base will result in a tetrahedral cage including both the protein and the DNA structural units. The dimensions of the cage are tunable by changing the length of the DNA strands in the triangular base.

FIG. 2A shows an underside view of ald$_3$ showing the three Cys54 residues in yellow. FIG. 2B shows a side view of ald$_3$. FIG. 2C shows the strategy for modifying the protein with DNA using thiol-specific chemistry. FIG. 2D shows denaturing SDS-PAGE of protein and protein-DNA conjugate. Lane M: protein molecular weight ladder; 1: unmodified ald$_3$; 2: purified (ald-DNA)$_3$. FIG. 2E shows native PAGE of protein samples. Lane 1: unmodified ald$_3$; 2: (ald-DNA)$_3$; 3: (ald-DNA)$_3$+complementary DNA; 4: (ald-DNA)$_3$+mismatched DNA. FIGS. 2F and 2G show AFM imaging and height profiles ald$_3$ and (ald-DNA)$_3$. Scale bar: 25 nm.

FIG. 3A shows self-assembly of (ald-DNA)$_3$ with multi-crossover (MX) DNA tiles bearing complementary handles. FIG. 3B shows native PAGE of (ald-DNA)$_3$ and MX tile association. FIG. 3C shows AFM images of indicated bands, isolated from the gel. Scale bar: 20 nm. FIG. 3D shows design of triangular DNA origami with three complementary handles to (ald-DNA)$_3$. FIGS. 3E and 3F show AFM images and height profiles of origami before and after protein association. Scale bar: 50 nm.

FIG. 4A shows design of three-turn protein-DNA tetrahedron (3t-aldTet). FIG. 4B shows native PAGE of purified 3t-Tet (lane 1), 3t-Base (lane 2), 3t-aldTet (lane 3). FIG. 4C shows AFM images of 3t-Tet, 3t-Base, and 3t-aldTet. FIG. 4D shows design of four-turn protein-DNA tetrahedron (4t-aldTet). FIG. 4E shows native PAGE of 4t-Tet (lane 1), 4t-Base (lane 2), 4t-aldTet (lane 3). FIG. 4F shows AFM images of 4t-Tet, 4t-Base, and 4t-aldTet. Scale bars for AFM images: 15 nm (zoom-ins), 100 nm (zoom-outs).

FIG. 5A shows a schematic of TCEP cleavage of 3t-aldTet. Reduction of the disulfide linkage between the protein and DNA should result in a base with double-stranded DNA arms if all three are bound to the protein. FIG. 5B shows native PAGE of 3t-Base (lane 1), 3t-aldTet (lane 2, 4), 3t-Base+complementary handles (lane 3), and 3t-aldTet following TCEP cleavage (lane 5). FIG. 5C shows AFM imaging of major band isolated from lane 5 (scale bar: 10 nm).

FIG. 6A shows the location of azidophenylalanine residues in the two mutants used. FIG. 6B shows SPAAC reaction between DNA-DBCO and ald containing (azF). FIGS. 6C and 6D show denaturing PAGE of the E54(azF) and E74(azF) mutants, respectively. In both gels lane 1 is the unmodified protein, and lane 2 is the (ald-DNA)$_3$ conjugate. FIGS. 6E and 6F show native PAGE and AFM images of the structures formed by the E54(azF) and E74(azF) (ald-DNA)$_3$ conjugates, respectively, with 3t-Base. The AFM images correspond to the bands in the red box. Scale bars: 25 nm.

FIG. 7A) Surface representation of the aldolase trimer: blue indicates one monomer, orange denotes position 54 (mutated to cysteine), and yellow indicates native disulfide bonds. FIG. 7B) Size exclusion chromatogram of the purified trimer. BSA is used as a control given its similar size to the assembled trimer. FIG. 7C) Native PAGE and FIG. 7D) Denaturing SDS-PAGE analysis of the purified aldolase protein. FIG. 7E) MALDI-TOF/TOF mass spectrum of the purified protein.

FIG. 8A) The aldolase-DNA conjugate was purified via anion exchange chromatography. Pk1, 2, and 3 indicate the three sample peaks collected. FIG. 8B) SDS-PAGE analysis of the three collected peaks, using wild-type aldolase (ald) as a reference. The orange arrow indicates unmodified ald and the blue arrow the (ald-DNA) conjugate. Pk 2 contains >95% purity of the desired (ald-DNA)$_3$ conjugate, and was used for subsequent experiments.

FIG. 9A) SDS-PAGE of SPDP-DNA conjugation to E54C aldolase. Lane 1: E54C aldolase prior to conjugation. Lane 2: wild-type aldolase exposed to SPDP-DNA, demonstrating that there is no non-specific linkage in the absence of C54; thus, the endogenous cysteine residues are unreactive under these conditions. Lane 3: E54C aldolase following SPDP-DNA conjugation but prior to purification; the upper band shows a conversion of ~50% per protein monomer. FIG. 9B) Circular dichroism spectrum of (ald)$_3$, (ald-DNA)$_3$, and free DNA to confirm that the DNA modification did not perturb the aldolase structure. FIG. 9C) AFM image E54C (ald)$_3$ protein prior to DNA modification. FIG. 9D) AFM image of purified (ald-DNA)$_3$. Scale bars: 100 nm. FIG. 9E) Box plot of diameter distribution for (ald)$_3$ and (ald-DNA)$_3$. The distributions are very similar, demonstrating that the trimers are intact even after DNA modification. A total of 30 particles for each sample were counted from the AFM images using NanoScope Analysis.

FIG. 10A) Schematic illustrations and strand design diagram for the MX tile (SEQ ID NOs:18 and 20-25). The left edge of the tile (indicated by the box) is extended with complementary handles complementary to the ald-DNA sequence. FIG. 10B) Native PAGE (5%) analysis of MX tile association with the (ald-DNA)$_3$ sample. Lanes 1 and 3: purified MX tile. Lane 2: MX tile mixed with (ald-DNA)$_3$ bearing the complementary handle; higher bands indicate protein binding to the tile. Lane 4: MX tile mixed with (ald-DNA)$_3$ where the DNA sequence is non-complementary (A)$_{21}$ and no association between the protein and the tile is seen. FIG. 10C) AFM image of aldolase-DNA assembled with MX tiles (scale bar: 100 nm), with a histogram showing the distribution of trimers bearing 0-3 tiles. Most proteins have three tiles bound, but smaller populations of 0-2 tiles are also seen. Samples were purified from a gel, demonstrating that breakdown of tiles from aldolase can occur during sample handling (e.g. centrifugation with molecular weight cutoff filters). FIG. 10D) Box plot of MX tile length distribution; the observed length is very close to 30 nm as dictated by the design. A total of 30 particles were counted from the AFM images using NanoScope Analysis. FIG. 10E) Native PAGE analysis of MX tile assembly with (ald-DNA)$_3$ at different temperatures. Lane 1: MX tile only. Lanes 2-5: assembly at 55° C., 37° C., 25° C., and room temperature. Only 55° C. yields upper bands indicative of protein-DNA self-assembly.

FIG. 11A) Schematic illustration of the triangular origami with handles (left), origami with handles complementary to the (ald-DNA)$_3$ (middle), and origami with non-complementary (ald-DNA)$_3$ handles (right). FIG. 11B) Zoom in and wide-field AFM image of the three samples from (FIG. 11A). Scale bars: 400 nm. Only origami with complementary handles show protein in the central cavity. FIG. 11C) Agarose gel electrophoresis. Lane 1: bacteriophage M13 genome (scaffold strand). Lane 2: (ald-DNA)$_3$. Lane 3: annealed origami prior to purification from gel and assembly with the (ald-DNA)$_3$; the intense upper band is the desired structure, the diffuse lower band is excess staple strands. The upper band was excised and used for self-assembly with (ald-DNA)$_3$.

FIG. 12A) Zoom-out AFM images of origami assembly with (ald-DNA)$_3$. Scale bar: 200 nm, applicable to all images. Green circles indicate origami with well-positioned protein; Red circles indicate empty origami; White circles indicate ambiguous cases, e.g. where the protein is not in the center of the cavity. FIG. 12B) Distribution of Green, White, and Red origami assembled with (ald-DNA)$_3$. Images were analyzed with Adobe Photoshop to determine the statistical distribution.

FIGS. 13A and 13B) Schematic illustrations of 3t-Base (left) and 4t-Base (right) self-assembly from four constituent strands. FIG. 13C) DNA sequence design of 3t-Base and 4t-Base (SEQ ID NOs:26-29 and 36-39). FIG. 13D) Size exclusion FPLC traces of 3t-Base and 4t-Base purification. The major peak was collected and used for self-assembly with (ald-DNA)$_3$. FIG. 13E) Native 5% PAGE characterization of purified 3t-Base and 4t-Base. For 4t-AldTet, the directionality of the handles was designed backwards, so the DNA handles were conjugated to the protein on the 3' end instead of the 5' end (as with the three-turn sample).

FIG. 14A) Self-assembly of 3t-aldTet. Lane 1: 3t-Base. Lane 2: 3t-Base assembly with (ald-DNA)$_3$; the boxed band is the desired 3t-aldTet (which was excised from the gel for FIG. 4), whereas the upper bands are the association of the protein with multiple 3t-Base structures. Lane 3: 3t-Base assembly with non-complementary (ald-(A)$_{21}$)$_3$. The lack of upper bands confirms that the association in Lane 2 is mediated by DNA hybridization. FIG. 14B) Self-assembly of 4t-aldTet. Lane 1: 4t-Base. Lane 2: 4t-Base assembly with (ald-DNA)$_3$; the boxed band is the desired 4t-aldTet (which was excised from the gel for FIG. 4), whereas the upper bands are the association of the protein with multiple 4t-Base structures. Lane 3: 4t-Base assembly with non-complementary (ald-(A)$_{21}$)$_3$. The lack of upper bands confirms that the association in Lane 2 is mediated by DNA hybridization.

FIG. 15A) 3t-Tet. FIG. 15B) 3t-Base. FIG. 15C) 3t-aldTet. Scale bars: 100 nm.

FIG. 16A) 4t-Tet. FIG. 16B) 4t-Base. FIG. 16C) 4t-aldTet. Scale bars: 100 nm.

FIG. 17A) In an effort to increase the yield of 3t-aldTet formation, (ald)$_3$ was modified with three (A)$_{21}$ (SEQ ID NO:47) handles, and 3t-Base with three complementary (T)$_{21}$ (SEQ ID NO:48) handles. We hypothesized that the ability of poly(A) handles to "slide" along poly(T) complements would allow for better assembly of the two components, based on success with even more sterically-demanding viral capsid-origami assemblies.[5] Contrary to this expectation, the co-assembly instead resulted in two-dimensional matted aggregates, perhaps due to the ability of the poly(A) handles to bind at arbitrary locations of the poly(T) complements. FIG. 17B) Native PAGE demonstrates that compared with 3t-Base((T)$_{21}$), addition of (ald-(A)$_{21}$)$_3$ results primarily in large aggregates unable to penetrate the gel. Lanes 3-6 correspond to 0, 0.1, 0.2, 0.4 and 1 equiv. of (ald-DNA)$_3$ added. FIG. 17C) AFM image of samples, showing aggregated and tangled mats of triangular structures and protein trimers. Scale bar: 200 nm.

FIGS. 18A-18E show edge length and height measurements for three-turn samples. FIGS. 18A-18C) Design and calculated dimensions of 3t-Tet, 3t-Base, and 3t-aldTet, respectively. FIGS. 18D and 18E) Box plots of distributions of edge lengths and particle heights, respectively, for samples as measured from AFM images. At least 300 particles were auto-counted for height analyses and 30 particles were manually counted for edge length analyses using NanoScope Analysis.

FIGS. 19A-19C) Design and calculated dimensions of 4t-Tet, 4t-Base, and 4t-aldTet, respectively. FIGS. 19D and 19E) Box plots of distributions of edge lengths and particle heights, respectively, for samples as measured from AFM images. At least 300 particles were auto-counted for height analyses and 30 particles were manually counted for edge length analyses using NanoScope Analysis.

FIG. 10A) Native PAGE (5%) of 3t-Base bearing 1, 2 and 3 handles. FIG. 20B) Native PAGE (5%) for self-assembly of (ald-DNA)$_3$ with 3t-Base bearing 1-3 handles. FIG. 20C) AFM images of (ald-DNA)$_3$ assembled with 3t-Base with two handles. FIG. 20D) AFM images of (ald-DNA)$_3$ assembled with 3t-Base with one handle. Scale bars for AFM images: 25 nm (zoom-ins), 100 nm (wide-field).

FIG. 21A) Molecular surface of ald$_3$ with E54(azF) mutation. The non-canonical amino acid is indicated in red. FIGS. 21B and 21C) FPLC chromatogram and SDS-page analysis of purified E54(azF) protein. FIG. 21D) Molecular surface of ald$_3$ with E74(azF) mutation. The non-canonical amino acid is indicated in red. FIGS. 21E and 21F) FPLC chromatogram and SDS-PAGE analysis of purified E74(azF) protein. Pk2 was used for subsequent experiments.

FIG. 11A) E54(azF) (ald-DNA)$_3$ assembly with 3t-Base. Lane 1: 3t-Base; Lane 2: 3t-Base+mismatched (ald-(A)$_{21}$)$_3$; no band shift is seen, confirming the specificity of DNA hybridization. Lane 3: 3t-Base+(ald-DNA)$_3$ demonstrating cage formation. FIG. 22B) E74(azF) (ald-DNA)$_3$ assembly with 4t-Base. Lane 1: 4t-Base; Lane 2: 4t-Base+(ald-DNA)$_3$ demonstrating cage formation. Lane 3: 3t-Base+mismatched (ald-(A)$_{21}$)$_3$; no band shift is seen, confirming the specificity of DNA hybridization.

FIGS. 23A and 23C) Wide-field and zoom-in AFM images, respectively, of 3t-aldTet with E54(azF) aldolase. FIGS. 23B and 23D) Wide-field and zoom-in AFM images, respectively, of 3t-aldTet with E74 (azF) aldolase. FIGS. 23E and 23F) Box plots of distributions in edge length and particle height, respectively, for 3t-aldTet with (azF)-aldolase. Scale bars for AFM images: 100 nm (wide-field), 25 nm (zoom-ins). At least 300 particles were auto-counted for height analyses and 30 particles were manually counted for edge length analyses using NanoScope Analysis.

FIG. 24A) Native PAGE of purified E54(azF) ald (Lanes 1 and 2) compared with E54C ald (lanes 3-5). The (azF)-containing protein shows one major band, whereas the protein with mutagenic cysteine shows multiple higher bands due to disulfide formation and protein aggregation. FIG. 24B) Denaturing PAGE of DNA conjugation to ald. Lane 1: E54C ald. Lane 2: E54C ald following DTT treatment and reaction with SPDP-DNA; multiple higher bands are seen. Lane 3: E54(azF) aid. Lane 4: E54(azF) aid following conjugation with DBCO-DNA; only a single protein-DNA conjugate band is seen.

FIG. 25A shows an embodiment with the protein component located on an exterior edge of the nanocage. FIG. 25B shows an embodiment with the protein component positioned within the interior cavity of the nanocage.

DETAILED DESCRIPTION OF THE DISCLOSURE

Figures 1A, 1B, 1C:
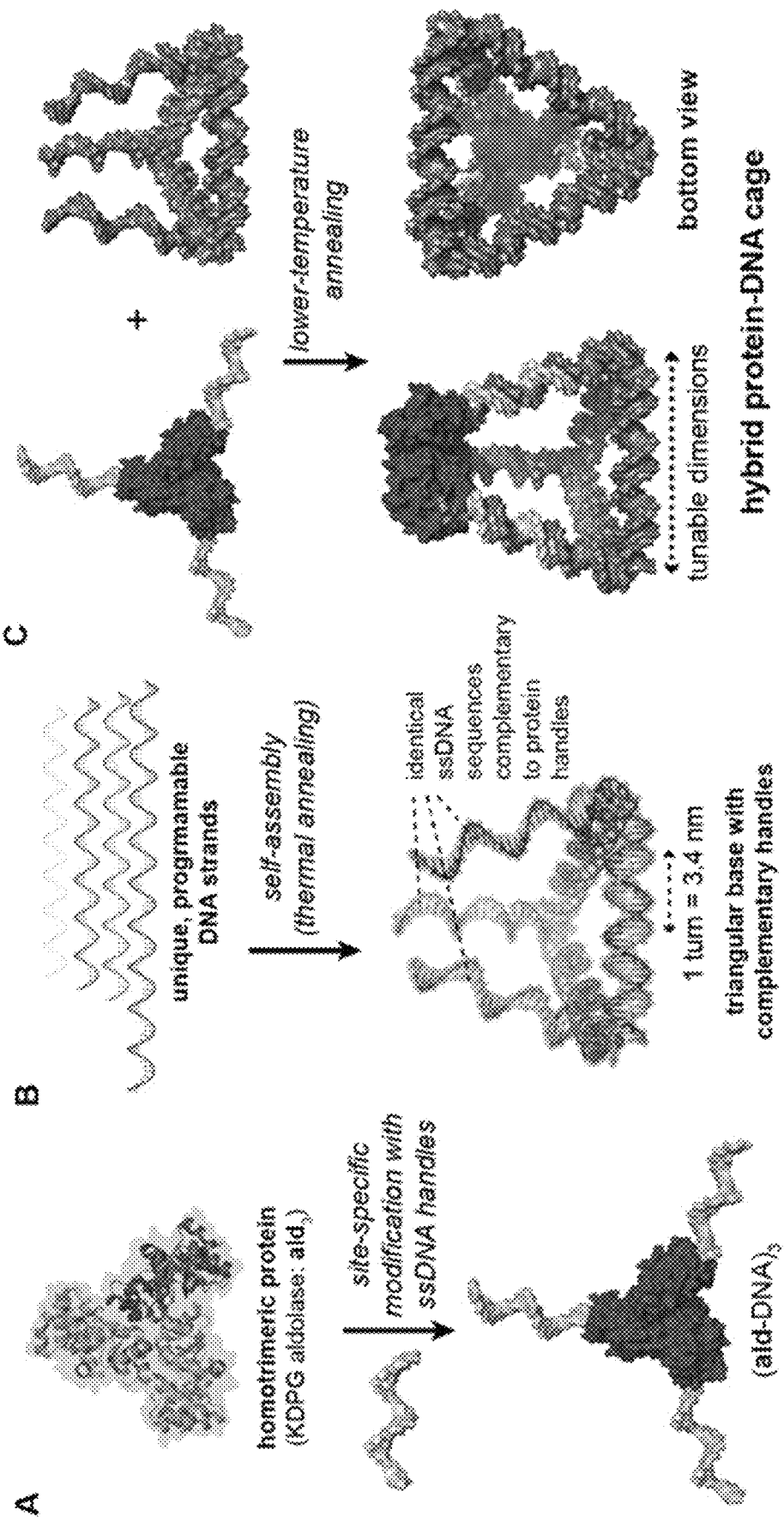
FIGS. 1A-1C show hybrid protein-DNA cage design.

The present disclosure describes tunable, self-assembling DNA-protein nanocages.

Described herein are hybrid nanocages that merge self-assembling protein building blocks with DNA scaffolds. These hybrid nanocages combine the bioactivity and chemical diversity of the protein building blocks with the programmability of DNA scaffolds. The hybrid nanocages form programmable and tunable polyhedron structures. The three-dimensional nanocages include a protein component and a DNA base, whereby the protein component and the DNA base are joined by hybridization of complementary nucleotide sequences covalently linked to the protein component and built into the DNA base. The size of the nanocage assembly can be tuned by changing the length of each DNA edge, whereas the protein provides a novel scaffold for the attachment of small molecules, targeting peptides, or even fusion proteins.

The protein component may include any suitable multimeric protein that can be functionalized or conjugated for covalent linkage to a polynucleotide handle. In some embodiments, each subunit of the multimeric protein is covalently linked to a polynucleotide handle. In some embodiments, the design of the nanocage may require multiple polynucleotide handles covalently linked to each subunit of the multimeric protein. In some embodiments, the design of the nanocage may require covalently linked polynucleotide handles at select subunits but not all subunits. The protein component may be a homomeric protein having multiple subunits of the same amino acid sequence or may be a heteromeric protein having two or more subunits of two or more amino acid sequences. In some embodiments, the protein component is a homotrimer, homotetramer, homopentamer, homohexamer, homoheptamer, homooctamer, homononamer, homodecamer, homoundecamer, homododecamer, or other multimeric protein in which each subunit has the same amino acid sequence. In some embodiments, the protein component is a heteromeric protein including submits of different amino acid sequences. In one embodiment, the protein component is 2-dehydro-3-deoxy-phosphogluconate (KDPG) aldolase ("aid").

The polynucleotide handle may be covalently linked to the protein component by any suitable chemical reaction known in the art. See Stephanopoulos et al. 2011 (Stephanopoulos, N., and Francis, M. B., Choosing an effective protein bioconjugation strategy, Natural Chemical Biology, 2011, 7:876), which is incorporated herein by reference.

In some embodiments, the polynucleotide handle is linked to a cysteine on the protein using thiol-selective chemistry such as, but not limited to, the heterobifunctional crosslinker succinimidyl 3-(2-pyridyldithio)propionate (SPDP) and a 5'amino modified oligonucleotide. The cysteine maybe a solvent-exposed cysteine reside present in the wild-type protein or the protein may be mutated at a solvent-exposed residue to incorporate a cysteine. The solvent-exposed cysteine may be located on the outer edge of the protein or may be a surface of the protein monomer.

As used herein "solvent-exposed" refers to an amino acid that, when the protein is folded into the proper tertiary and quaternary structure, is partially or completely exposed to solvent on the edge or surface of the protein.

In some embodiments, the polynucleotide handle is linked to a non-canonical or non-natural amino acid, including but not limited to 4-azidophenylalanine (azF). The protein component may be mutated to incorporate a non-canonical amino acid using, for example, the Schultz amber codon suppression method. Using non-canonical azF, the polynucleotide handle may be functionalized with a dibenzocyclooctyne (DBCO) moiety prior to covalent linkage to the azF-modified protein component.

In some embodiments, the polynucleotide handle is linked by N-terminal transamination of the protein component followed by reaction with aminooxy DNA. See, for example, Gilmore et al. (Gilmore, J. M., Scheck, R. A., Esser-Kahn, A. P., Joshi, N. S. & Francis, M. B. N-terminal protein modification through a biomimetic transamination reaction. *Angew. Chem. Int. Ed. Engl.* 45, 5307-5311 (2006)), which is incorporated herein by reference.

In some embodiments, the polynucleotide handle is by oxidative coupling of modified DNA with 4-aminophenylalanine protein mutants. See for example Stephanopoulos et al. 2010 (Stephanopoulos, N., Tong, G. J., Hsiao, S. C. & Francis, M. B. Dual-surface modified virus capsids for targeted delivery of photodynamic agents to cancer cells. *ACS Nano* 4, 6014-6020 (2010)) and Stephanopoulos et al. 2009 (Stephanopoulos, N., Carrico, Z. M. & Francis, M. B. Nanoscale integration of sensitizing chromophores and porphyrins with bacteriophage MS2. *Angew. Chem. Int. Ed. Engl.* 48, 9498-9502 (2009)), both of which are incorporated herein by reference.

The polynucleotide handle is a DNA sequence covalently linked to the protein component and complementary to a nucleotide strand of the DNA base of the nanocage. The polynucleotide handle and the complementary nucleotide strand of the DNA base hybridize to link the protein component to the DNA base. The length of the polynucleotide handle may be changed in accordance with the desired properties of the nanocage. In some embodiments, the polynucleotide handle is at least 6 bp, at least 9 bp, at least 12 bp, at least 15 bp, at least 18 bp, at least 21 bp, or longer. In some embodiments, the polynucleotide handles are complementary to corresponding single-stranded sequences on the DNA base over a span of at least 6 bp, at least 9 bp, at least 12 bp, at least 15 bp, at least 18 bp, at least 21 bp, or at least 24 bp. A skilled artisan will appreciate that the length of the polynucleotide handle linked to the protein component may be altered to change the properties and size of the nanocage.

Figure 25A:
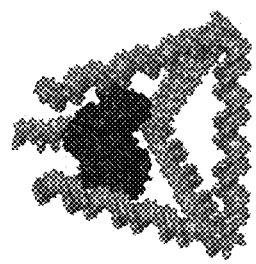
FIGS. 25A-25B show two embodiments of the protein-DNA nanocages described herein.
Figure 25B:
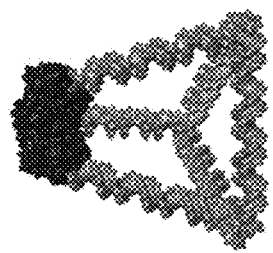

Multiple configurations of the nanocage are contemplated herein and variations in the linkage of the polynucleotide handle to the protein component may alter the resulting nanocage configuration. In some embodiments, the polynucleotide handle is linked to the protein component in a configuration that positions the protein on an exterior edge or exterior face of the nanocage (see FIG. 25A). In some embodiments, for example, the 3' end of the polynucleotide handle is exposed such that, when hybridized with the DNA assembly, the protein component is located on an exterior edge or exterior face. In some embodiments, the polynucleotide handle is linked to the protein component in a configuration that positions the protein within the interior cavity of the nanocage (see FIG. 25B). In some embodiments, for example, the 5' end of the polynucleotide handle is exposed such that, when hybridized with the DNA assembly, the protein component is located within the interior cavity of the nanocage. Various alternative arrangements of the protein and DNA assembly can be envisioned by a skilled artisan and the arrangement of the protein and DNA assembly is not limited to the embodiments described herein.

The DNA assembly used as the base of the nanocage is formed from self-assembling single-stranded DNA oligonucleotides. The single-stranded DNA oligonucleotides include complementary portions that hybridize to form a base with single-stranded handles complementary to the polynucleotide handles covalently linked to the protein component. The DNA base may be assembled from at least four or more oligonucleotides to form a base of the desired geometry. The length of the sides of the base may be tuned by changing the length of the oligonucleotides used. A skilled artisan will appreciate that the length, number of oligonucleotides and the sequences thereof may be tuned and designed to from a self-assembling base of any number of geometries. In some embodiments, 4 oligonucleotide strands may be designed to form a triangular base with three single-stranded arms to hybridize with three polynucleotide handles on the protein portion. In some embodiments, 5 oligonucleotide strands may be designed to form a square base with four single-stranded arms to hybridize with four polynucleotide handles on the protein portion. In some embodiments, 6 oligonucleotide strands may be designed to form a pentagonal base with 5 single-stranded arms to hybridize with five polynucleotide handles on the protein portion. Additional embodiments of origami DNA structures are known in the art and can be used as a base with the nanocages described herein. See for example, Rothemund "Folding DNA to create nanoscale shapes and patterns," Nature, 440, 297-302, 2006, which is incorporated herein in its entirety.

The size of the nanocage may be tuned by changing the length of the oligonucleotides used in the DNA assembly or by changing the multimeric protein selected. In some embodiments, the dimensions of the nanocage are less than 100 nm×100 nm×100 nm. In another embodiment, the dimensions of the nanocage are less than 75 nm×50 nm×50 nm. In another embodiment, the dimensions of the nanocage are about 10-70 nm×10-40 nm×10-40 nm.

The nanocage is assembled by annealing of the polynucleotide handle of the protein component to the single-stranded DNA arms of the DNA base to form hybridized double-stranded helices. Prior to or during annealing, the nanocage structure may be loaded with a payload. The payload may be therapeutic agents, bioactive compounds, biomolecular reagents, biocatalysts, and other molecular compounds of interest, or combinations thereon. The payload may include, but is not limited to, a nucleic acid, a polypeptide, a protein, an enzyme, an antibody, a phospholipid, or other macromolecule or macromolecular assembly, or combinations thereof.

In some embodiments, the protein component may be further functionalized as a molecular scaffold to assemble other oligonucleotides, proteins, enzymes, etc. The attachment of other biomolecules to the protein component will allow for multivalent targeting and cargo delivery to specific sites. Biomolecules that may be attached to the protein component include, but are not limited to, nucleic acids, polypeptides, proteins, enzymes, antibodies, carbohydrates, polysaccharides, and phospholipids.

In a particular embodiment, a nanocage described herein is a three-dimensional tetrahedral cage containing a homotrimeric protein linked to a triangular base of DNA. The protein trimer is first functionalized with single-stranded DNA polynucleotide handles at a specific amino acid on each of the three monomers (see FIG. 1A). The 4 stranded triangular DNA base, which includes three single-stranded DNA handles complementary to the polynucleotide handles on the protein timer, is self-assembled and purified separately via thermal annealing (FIG. 1B). Combining the protein and DNA base building blocks, and annealing at a lower temperature, does not disrupt the protein-protein interface nor the DNA edges at the base of the structure, yielding a three-dimensional tetrahedral cage (FIG. 1C).

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present embodiments have been described in terms of one or more preferred embodiments, and it should be appreciated that many equivalents, alternatives, variations, and modifications, aside from those expressly stated, are possible and within the scope of the embodiments.

Example 1

The embodiment described here demonstrates a protein-DNA nanocage constructed through chemical conjugation of oligonucleotide handles on a protein building block. In particular, this example demonstrates the design and assembly of a tetrahedral nanocage structure including a homotrimeric protein covalently linked to a polynucleotide handle and a triangular DNA base including 4 nucleotide strands, where the polynucleotide handles linked to the protein are complementary to and hybridize with three of the strands of the triangular DNA base.

Methods

Protein Expression—

The gene for KDPG aldolase was inserted into the pet28b+ plasmid using standard molecular cloning techniques, and then used to transform E. coli BL21(DE3) competent cells (New England Biolab Inc. USA) for protein expression. Protein sequences are provided in Table 1 and a summary of plasmids used is provided in Table 2. All expression constructs described herein were verified by DNA sequencing subsequent to cloning. The E54C mutant was prepared using a primer with the mutated nucleotides in the center of the forward and reverse primers, and introduced using the Q5 Site-Directed Mutagenesis Kit following the kit protocol (New England Biolab Inc. USA). The mutated plasmid was then transformed into E. coli BL21 (DE3) cells. For the generation of aldolase protein containing the non-canonical amino acid 4-azidophenylalanine (azF) (Bachem Americas Inc. USA), the amber (TAG) stop codon was introduced at either position 54 or 74 using a QuikChange Site-Directed mutagenesis kit (Stratagene, USA). The plasmids containing the amber mutation at position 54 or 74 were derived from the pEt28– kdgA parent plasmid. Using site directed mutagenesis, a single point mutation was made by replacing an existing amino acid in the aldolase with the TAG codon. PCR primers were designed to have 10-21 bp of homology on either side of the TAG mutation. Each set of primers was used to amplify the aldolase amber mutation using pEt28– kdgA plasmid as the template. The amplified PCR product was digested with Dpn1 to yield the new mutant plasmid.

The BL21(DE3) cells that were previously transformed with both the native and E54C mutation were used for protein expression. Cells were grown in 1× Terrific Broth (TB) at 37° C. containing 100 µg/mL ampicillin to an $OD_{600}$=0.8, then induced with 0.5 mM IPTG (isopropyl-β-D-thiogalactopyranoside) (SigmaAldrich, USA) at 37° C. for 4 hours, and then harvested by centrifugation at 6000 RPM for 20 minutes. For the non-canonical amino acid incorporation, two plasmids were required, one for expression of the aldolase gene containing the amber stop codon and a second containing the orthogonal tRNA and aminoacyl-tRNA synthetase pair. Both the pEt28– kdgA (E54azF) and pDule2 plasmids were co-transformed into BL21(DE3) cells and grown 1× Terrific Broth (TB) at 37° C. containing supplemented with 100 µg/ml ampicillin and 50 µg/ml spectinomycin) (VWR, USA). Once the cells had reached $OD_{600}$=0.8, the non-canonical amino acid (azF) was added to the growth media to a final concentration of 1 mM and protein expression was induced with 0.5 mM IPTG and 0.02% L-arabinose (VWR, USA). Cells were shaken overnight at 37° C., and then harvested by centrifugation.

Protein Purification and Characterization—

Following protein expression, the harvested cell pellets were resuspended in lysis buffer containing 20 mM Tris pH 8.0, 150 mM NaCl, 10 mM imidazole, 0.1 µM EDTA, and lysed using sonication. After sonication, the cell lysate was centrifuged at 13,000 rpm for 30 min to remove cell debris. The supernatant was transferred onto a Ni-NTA 5 ml His-Trap HP column (GE Healthcare, USA) and rinsed with 20 mM Tris pH 8.0, 300 mM NaCl, 10 mM imidazole to remove non-specifically bound species. The His-tagged aldolase was isolated with a 20 column volume linear gradient of lysis buffer with elution buffer containing 20 mM Tris pH 8.0, 150 mM NaCl, 500 mM imidazole. Fractions were pooled and placed in 30 kDa molecular weight cutoff dialysis membranes and dialyzed overnight at 4° C. against 1 L of PBS buffer (10 mM $Na_2HPO_4$, 1.8 mM $KH_2PO_4$, 137 mM NaCl, 2.7 mM KCl pH=7.6). The aldolase protein was subjected to size exclusion chromatography with a Superdex Increase 75 10/300 GL column (GE Healthcare, USA). The peak fractions were then analyzed via SDS-PAGE and fractions corresponding to the pure aldolase were combined and concentrated using an Amicon-30 kDa (Millipore Sigma, USA) cutoff filter out small-molecular weight impurities. Fractions were further characterized for purity and mass using MALDI-TOF on an ABI4800-TOF/TOF mass spectrometer.

AFM Imaging—

Samples (2 µL) were deposited on freshly cleaved mica (Ted Pella, Inc. USA), followed by addition of 60 µl of 1×TAE buffer containing 45 mM Tris pH 8.0, 12.5 mM Mg(OAc)$_2$·6H$_2$O, and 2 mM EDTA with 2 µl of 10 mM NiCl$_2$ (hereafter referred to as "1×TAE-Mg$^{2+}$"). Samples were allowed to adsorb at room temperature for 5 min, and then scanned in a tapping mode on a Pico-Plus AFM (Molecular Imaging, Agilent Technologies) with NP—S tips (Veeco, Inc. USA). All images were collected under ambient condition in tapping mode using the AFM. Width and height profiles were determined from horizontal line scans.

Synthesis of SPDP-DNA and DBCO-DNA Conjugates—

All single-stranded DNA oligonucleotides used for conjugation were purchased from Integrated DNA Technologies, Inc. (idtdna.com). SPDP was used to crosslink aldolase to an amine-modified oligo DNA using a modification of the protocol described in Dutta et al. "A DNA-directed light-harvesting/reaction center system," Journal of the American Chemical Society, 2014, 136(47), 16618-16625, which is incorporated herein by reference. 500 µL of 400 µM 5'-amine-modified DNA oligo (5'-AmMC6-TGAGTTCCGTCAGGTCTGCTC-3' (SEQ ID NO:46)) in 1×PBS (pH 7.6) was combined with 20 equivalents of 50 mM SPDP ((N-succinimidyl 3-(2-pyridyldithio) propionate (Thermo Scientific, USA) in DMSO. The mixture was shaken for one hour at room temperature and then purified by reverse phase HPLC to remove free DNA and excess SPDP. Following SPDP modification of DNA, the conjugate was separated on a Zorbax Eclipse 5 XDB-C18 column (150×4.6 mm). 80 µL of the SPDP-DNA solution was purified via HPLC with an XDB-C18 column using an elution gradient from 10% to 60% methanol in 50 mM TEAA (triethylammonium acetate) (Thermo Fisher Scientific, USA). DNA was modified with DBCO using a modification of the protocol described in Stephanopoulos et al. "Bioactive DNA-peptide nanotubes enhance the differentiation of neural stem cells into neurons," Nano Letters, 2015, 15(1), 603-9, which is incorporated herein by reference. The amine-modified oligonucleotide was dissolved in 1×PBS and combined with 20 equivalents of DBCO-sulfo-NHS (100 mM in DMSO), and the mixture was shaken overnight at room temperature. The DBCO-DNA conjugate was purified by HPLC to remove free DNA and excess DBCO.

Protein Modification and Characterization—

Figures 8A, 8B:
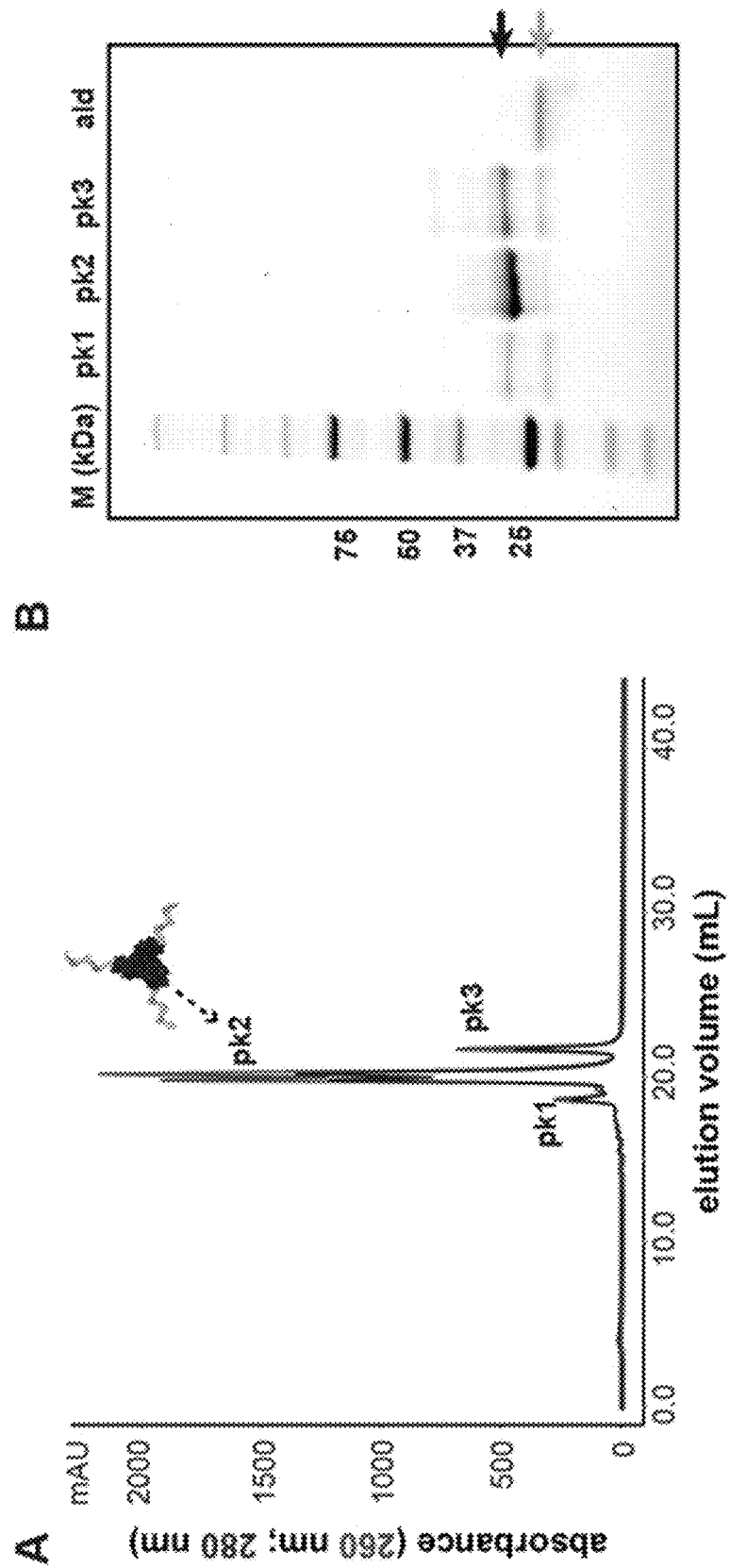
FIGS. 8A-8B show aldolase-DNA conjugation with SPDP-linked DNA.

Prior to conjugation, the purified E54C aldolase protein was treated with 10 equivalents of 100 mM DTT (1,4-dithiothreitol) for 30 min at 4° C. A 30 kDa molecular weight cutoff (MWCO) Amicon filter was used to wash the protein 3 times with PBS to remove excess DTT. To the reduced protein solution was added 6 equivalents of the purified SPDP-DNA conjugate. The reaction mixture was shaken gently overnight at 4° C. The excess SPDP-DNA was removed by filtration using a 30 kDa MWCO filter and washed twice with 20 mM Tris buffer. Following SPDP-DNA conjugation to Cys54, the solution contained a mixture of trimer bearing between 0-3 DNA strands. To isolate the aldolase trimer containing 3 oligonucleotides ((ald-DNA)$_3$), the reaction products were purified by anion exchange chromatography using a Mono Q 4.6/100 PE column (GE Healthcare, USA). As shown in FIG. 8A, three peaks from the chromatogram were collected. The fractions corresponding to each peak were concentrated using 30 kDa MWCO filters and analyzed by SDS-PAGE (FIG. 8A). For the click conjugation, freshly purified E54(azF) or E74(azF) aldolase samples were mixed with 6 equivalents of purified DBCO-DNA and shaken gently overnight at room temperature. Protein-DNA conjugates were purified using the same protocol as the thiol-mediated conjugation.

MX Tile Assembly with (ald-DNA)$_3$—

All strands comprising the MX tile were mixed together in 1×TAE-Mg$^{2+}$ buffer. The tiles were formed by thermally annealing the mixture from 90-20° C. over 2 hours. The annealed MX tiles were purified from a native PAGE gel, then mixed with 2 µl of 5 µM aldolase-DNA in in 1×TAE-Mg$^{2+}$ buffer. The MX tile and (ald-DNA)$_3$ mixture was annealed from 55-15° C. over 5 hours, followed by purification by native PAGE electrophoresis using standard elution procedures in 1×TAE-Mg$^{2+}$.

Triangular Origami Assembly with (ald-DNA)$_3$—

Figures 11A, 11B, 11C:
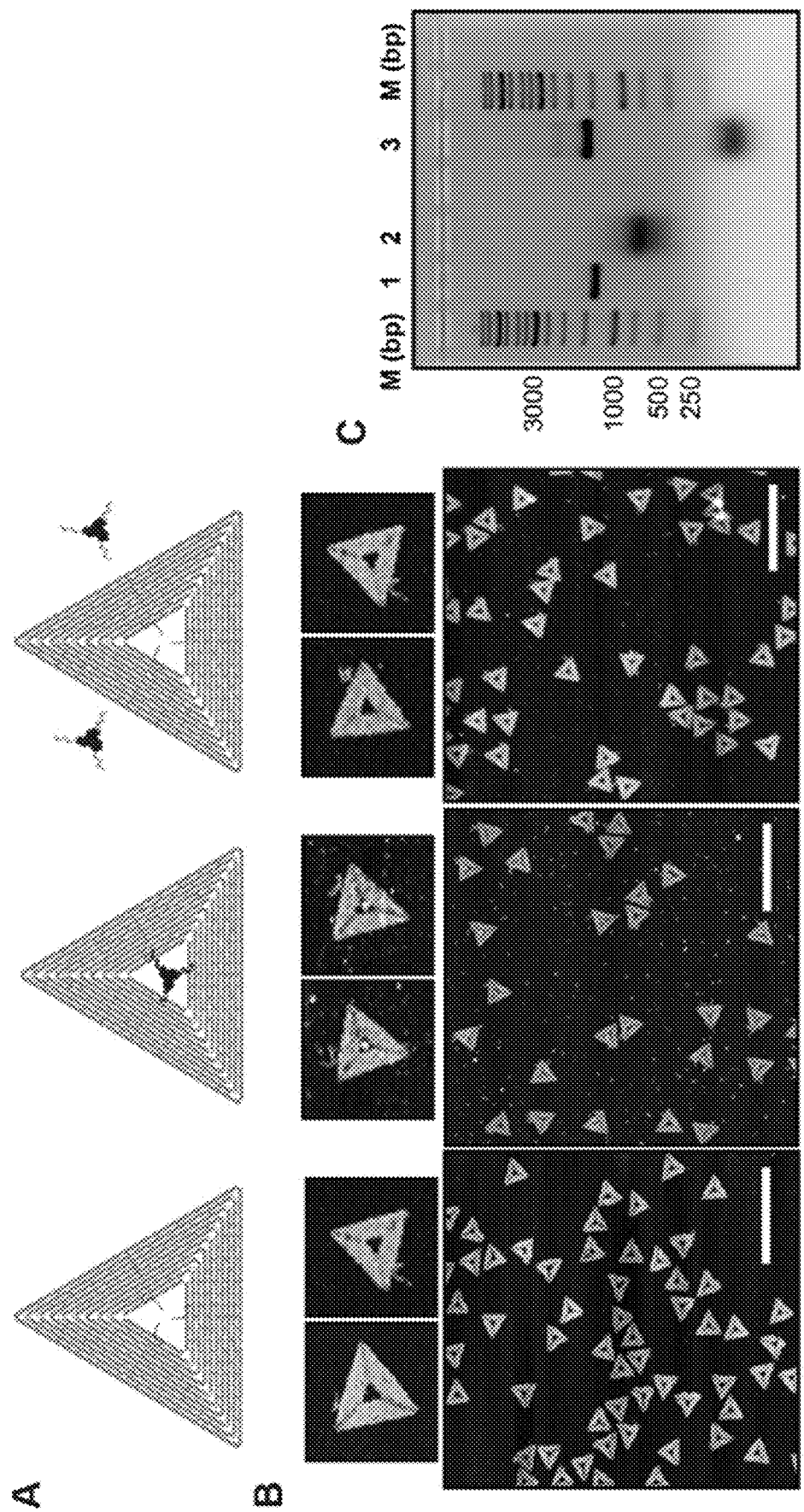
FIGS. 11A-11C show triangular origami assembly with (ald-DNA)$_3$.
Figures 12A, 12B:
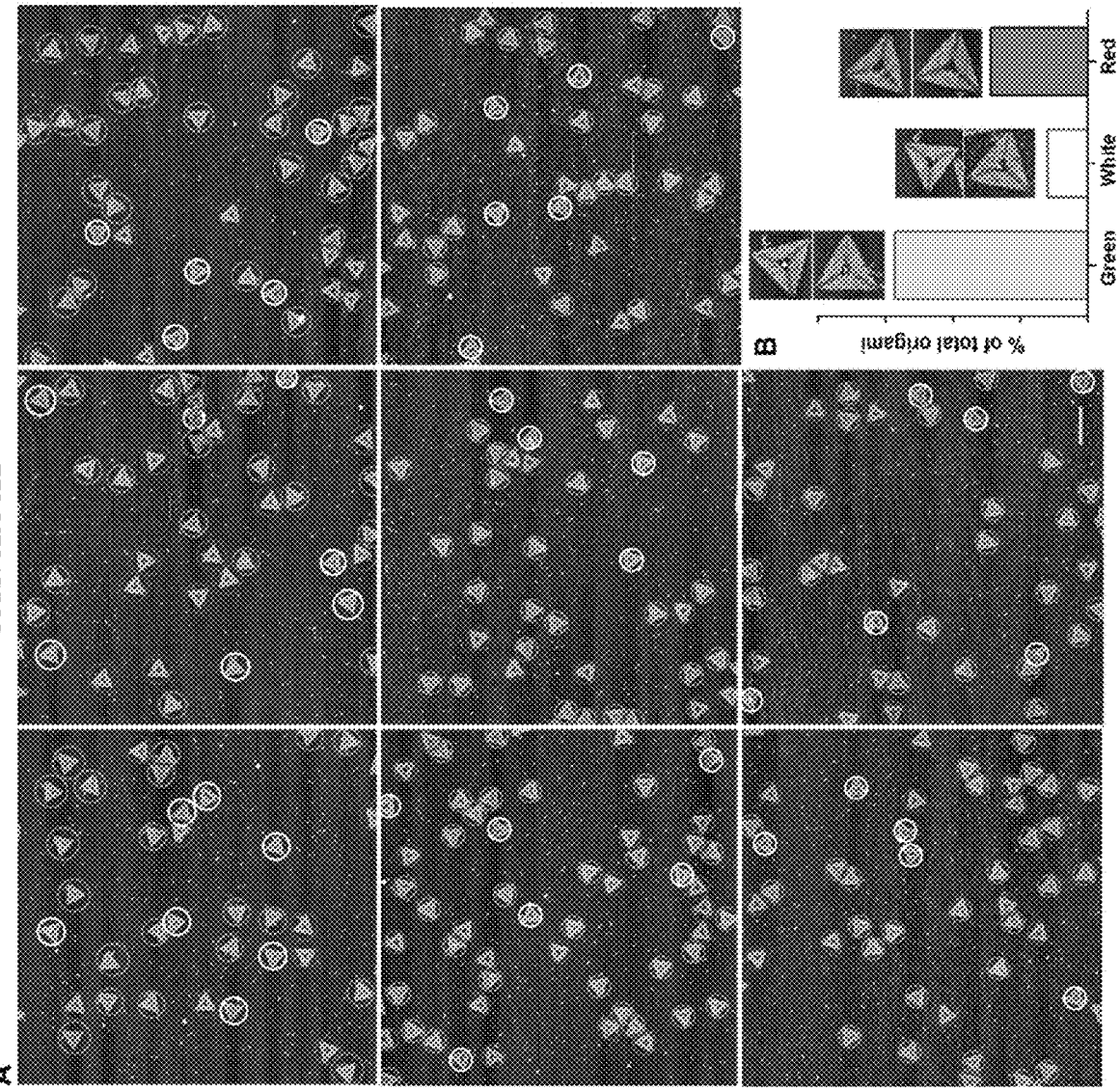
FIGS. 12A-12B show AFM quantification of (ald-DNA)$_3$ binding to triangular origami.
Figures 13A, 13B, 13C, 13D, 13E:
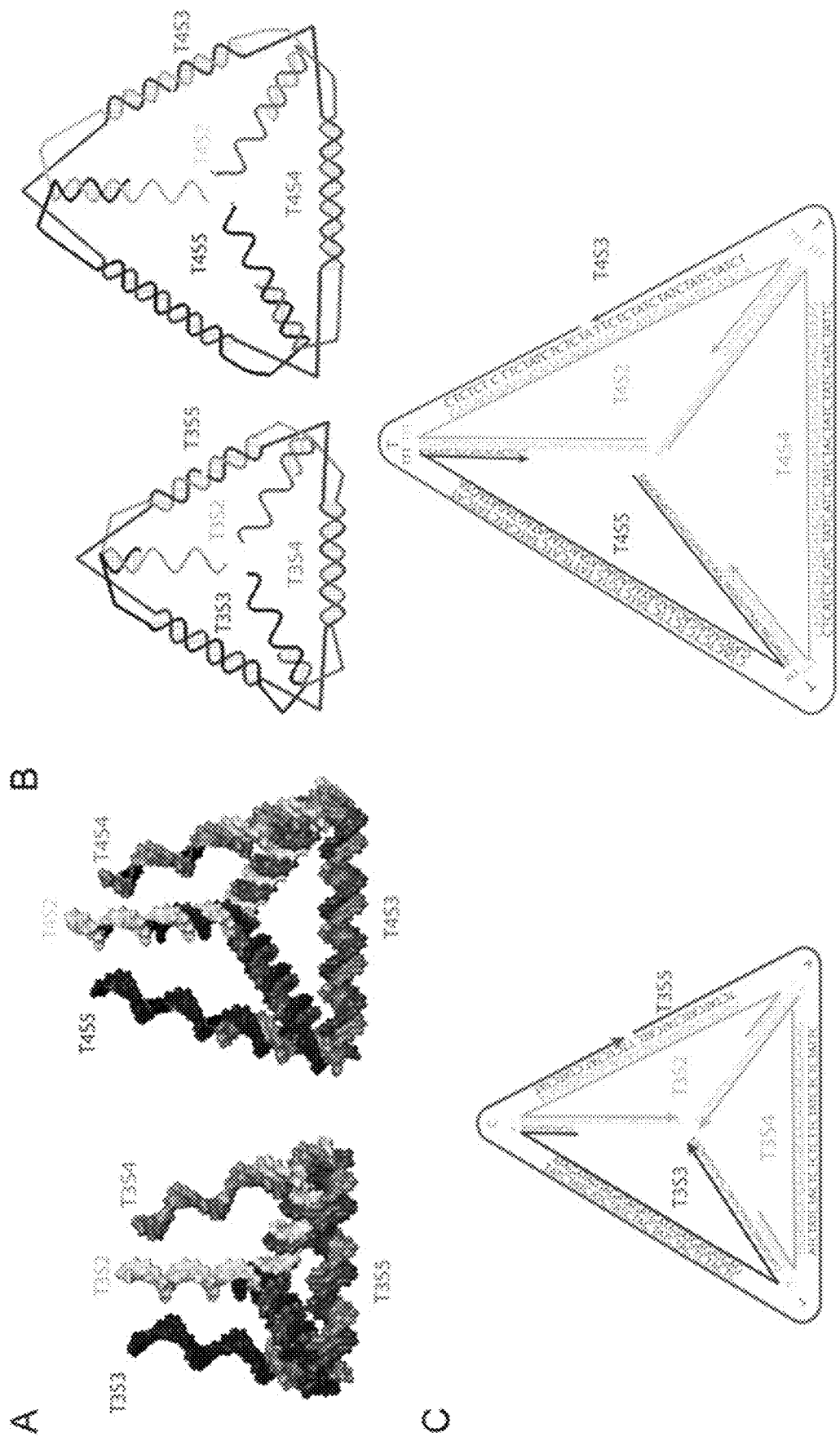
FIGS. 13A-13E show design of triangular bases for protein-DNA cages.
Figures 13A, 13B, 13C, 13D, 13E:
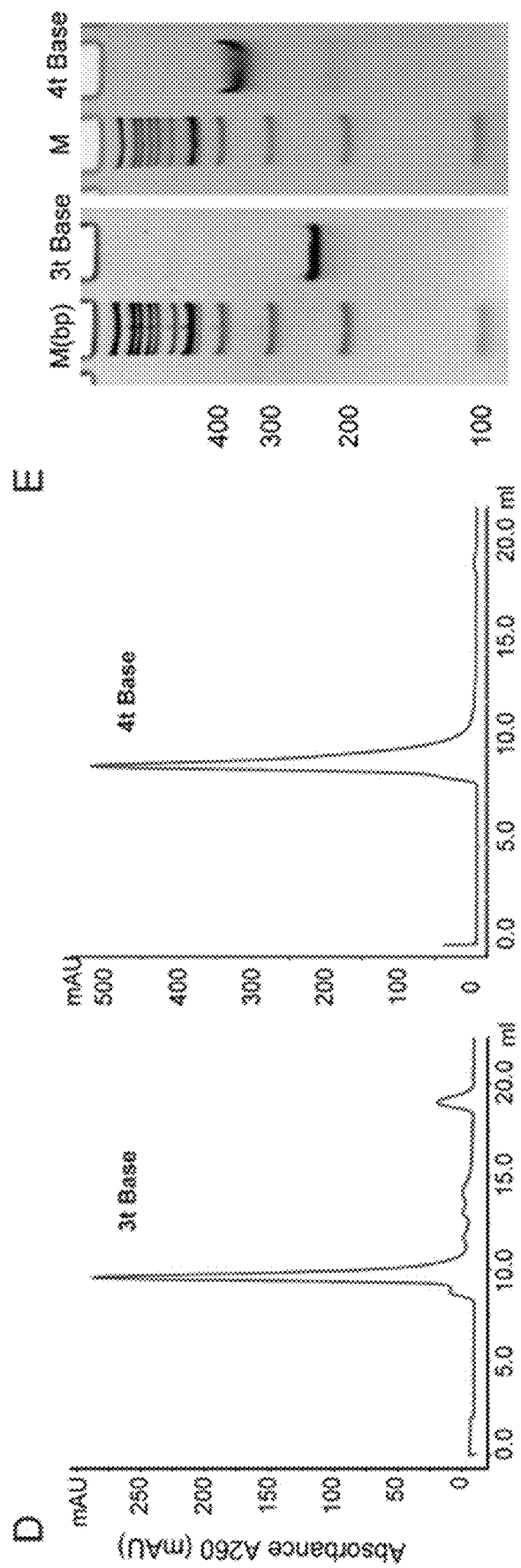

All strands for the triangle origami structure were combined in 1×TAE-Mg2+ buffer and the mixture was annealed from 90-20° C. over 2 hours. Origami design and purification followed those reported in Ding et al. "Gold nanoparticle self-similar chain structure organized by DNA origami," Journal of the American Chemical Society, 2010, 132(10), 3248-+, which is incorporated herein by reference. In order to attach the (ald-DNA)$_3$ samples, three staple strands were replaced with staples extended with complementary handles (S211, S212, and S213 below, FIGS. 11A-11C, numbering same as in Ding et al. Gold Nanoparticle Self-Similar Chain Structure Organized by DNA Origami, Journal of the American Chemical Society, 2010, 132(10), 3248, which is incorporated herein by reference in its entirety).

```
Sequences of staple strands with probes (5'→3')
S211
                                       (SEQ ID NO: 15)
TTTACGAGGCCCAATAGCAAGCAGAGCAGACCTGACGGAACTCA S212
                                       (SEQ ID NO: 16)
GCCTTTACGCCAGTTACAAAATAGAGCAGACCTGACGGAACTCA S213
                                       (SEQ ID NO: 17)
GTTAAGCCAGCCTTAAATCAAGAGAGCAGACCTGACGGAACTCA
```

Protein-DNA Cage Assembly—

All component strands of the tetrahedron were mixed together in an equimolar ratio in 1×TAE-Mg$^{2+}$ buffer. DNA samples (the Tet and Base samples) were formed by annealing the oligo mixtures from 90° C. to 20° C. for 2 hours, and then purified via size exclusion chromatography using a Superdex Increase 75 10/300 GL column. To form the aldTet samples, the corresponding Base samples were diluted 10-fold and combined with 2 µL of 5 µM aldolase-DNA in 1×TAE-Mg$^{2+}$ buffer, followed by annealing from 55-15° C. over 5 hours. The annealed aldTet samples were purified using the same procedure for the MX tiles described above. For the TCEP cleavage described in FIG. 5, a 0.3 M TCEP solution was prepared and adjusted to pH=7.0 with sodium hydroxide. The purified 3t-aldTet was incubated with 20 mM TCEP for 1 hour at room temperature in 1×TAE-Mg$^{2+}$ buffer.

Materials—

The kdgA gene of 2-dehydro-3-deoxy-phosphogluconate (KDPG) aldolase, was purchased from the DNASU plasmid repository.[1,2] The pDule2 plasmid was a gift from Prof. Matthew B. Francis (University of California, Berkeley). 4-azidophenylalanine (azF) was purchased from Bachem Americas Inc. Tris (2-Carboxyethyl) phosphine (TCEP) powder and DBCO-sulfo-NHS were purchased from Sigma Inc. N-succinimidyl 3-(2-pyridyldithio) propionate (SPDP) and dibenzocyclooctyne (DBCO-sulfo-NHS ester) were purchased from Life Technologies and BroadPharm.

ssDNA Purification—

All single-stranded DNA oligonucleotides used for the construction of the tetrahedral DNA cages, MX tiles, and triangular origami were purchased from Integrated DNA Technologies, Inc. (available on the World Wide Web at idtdna.com), and were purified by 6% denaturing polyacrylamide gel electrophoresis (PAGE). The target bands excised from the gel, eluted overnight, washed with butanol and precipitated in ethanol. The pelleted DNA was then dried and resuspended in nanopore water. The codon at the primer site for each mutation is indicated in bold in Table 3.

Results and Discussion

Figures 2A, 2B, 2C, 2D, 2E, 2F, 2G:
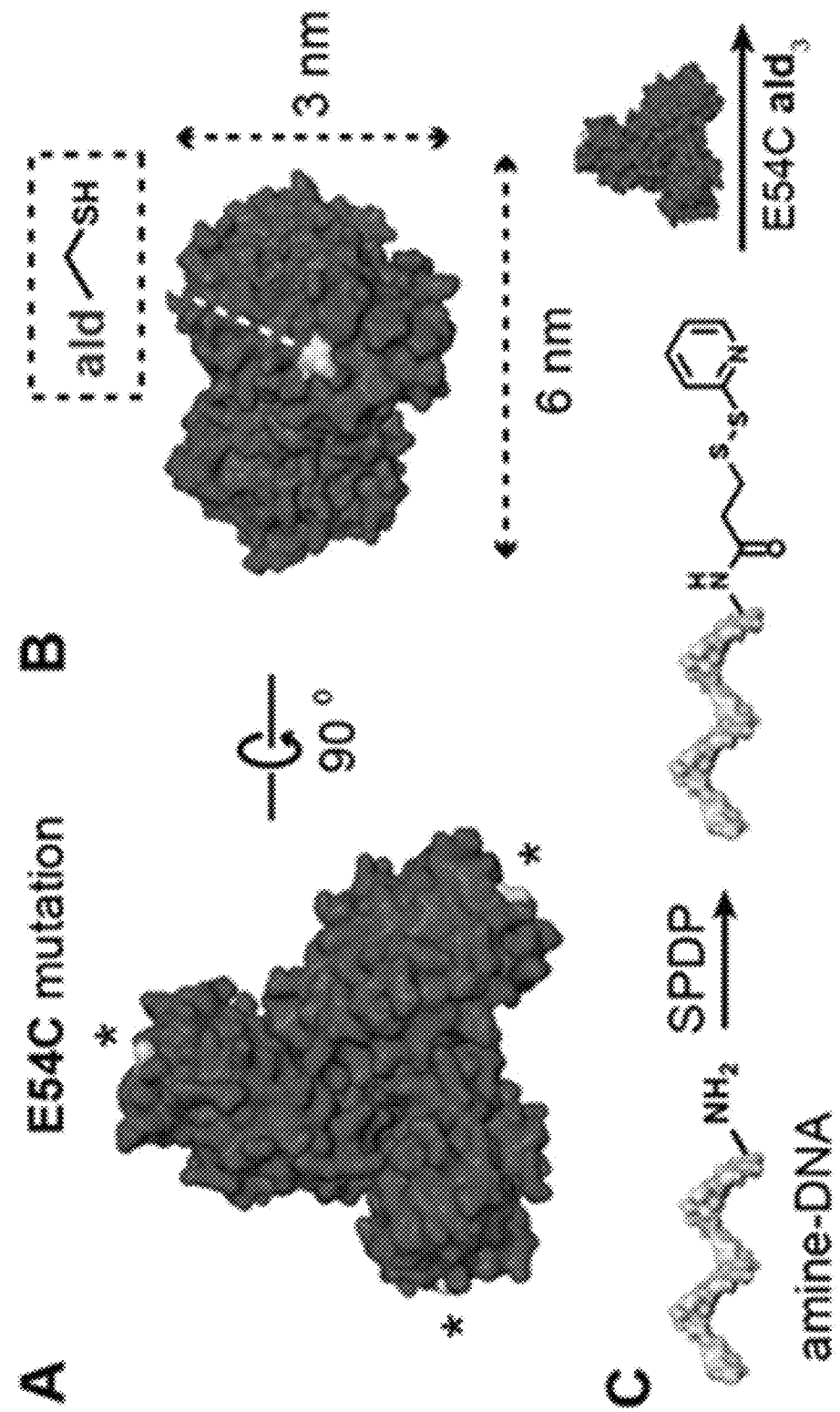
FIGS. 2A-2G show protein modification and characterization.
Figures 2A, 2B, 2C, 2D, 2E, 2F, 2G:
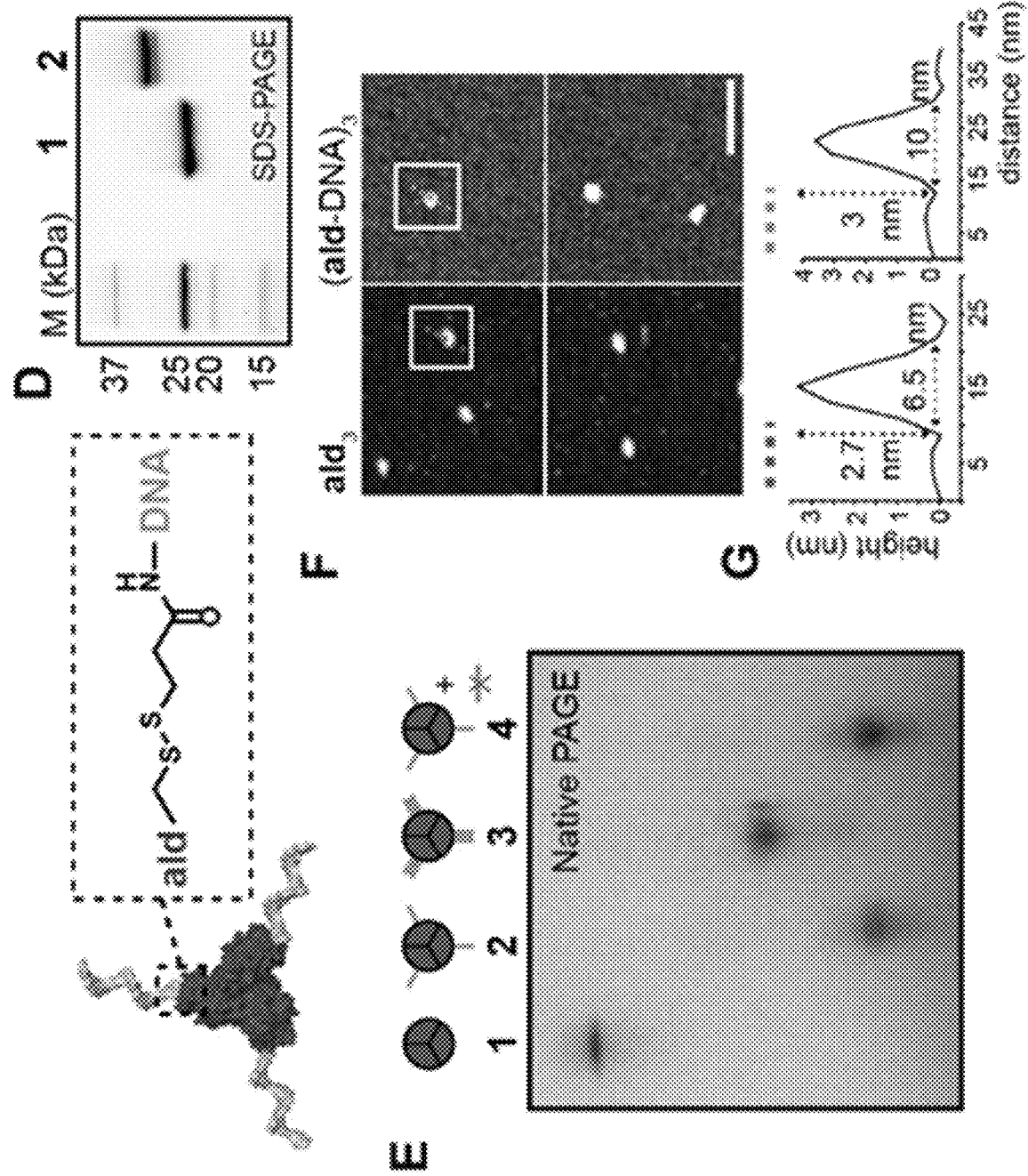
Figures 7A, 7B, 7C, 7D, 7E:
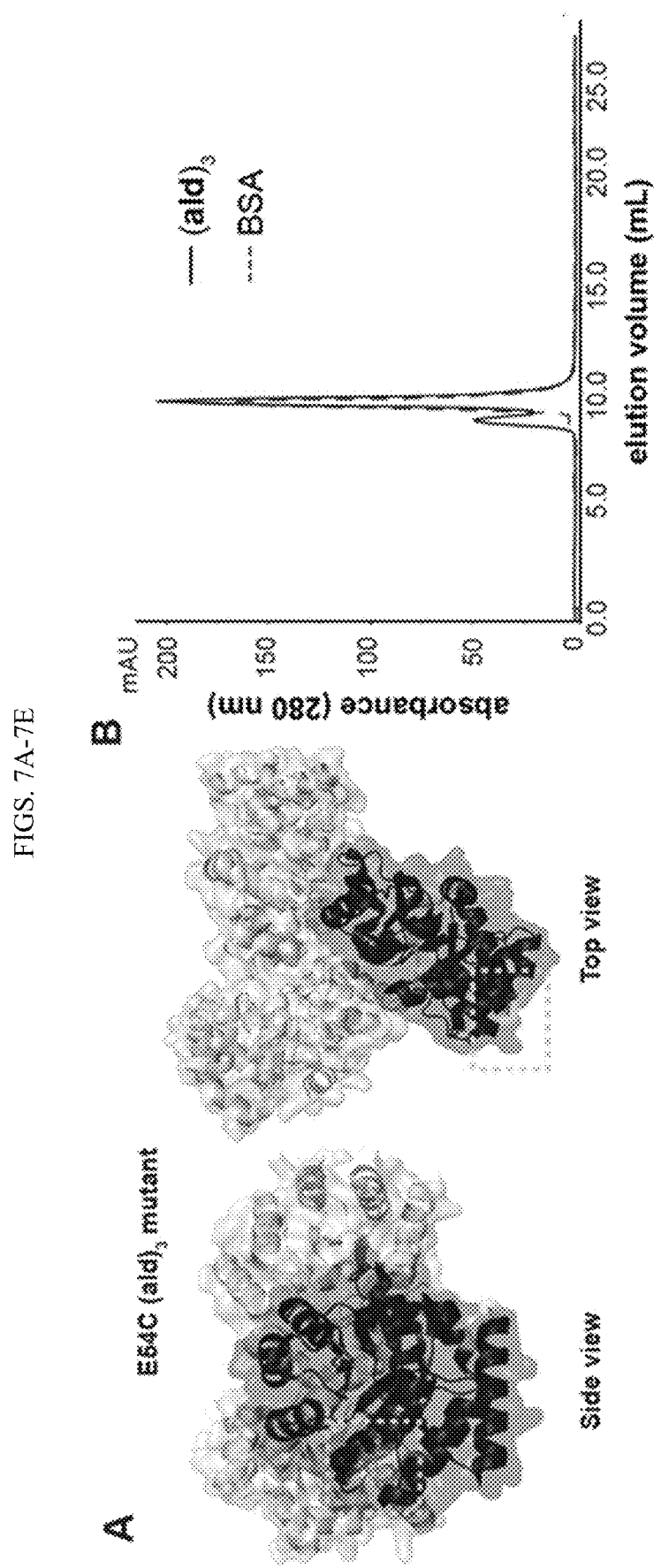
FIGS. 7A-7E show purification and characterization of aldolase.

For the trimeric protein building block, 2-dehydro-3-deoxy-phosphogluconate (KDPG) aldolase (hereafter referred to as ald), a 25 kDa protein that forms a C3-symmetric homotrimer $ald_3$ (FIG. 1A) was selected. In addition to the high thermal stability of the trimer (~80° C.), ald is readily amenable to mutagenesis and recombinant expression in *E. coli* and has been used in protein nanocage engineering. Furthermore, its size (6 nm diameter, 3 nm thickness, FIGS. 2A and 2B) is comparable with small oligonucleotide nanostructures like the four-strand DNA tetrahedron, first reported by Turberfield et al., Science 2005, and employed extensively in DNA nanotechnology. Although ald is an enzyme, here it is used as a structural building block, divorced from its chemical functionality, similar to the reports of Hsia et al. (Hsia et al. "Design of a hyperstable 60-subunit protein icosahedron," Nature 2016, 535 (7610), 136-+) and Patterson et al. (Patterson et al. "Evaluation of a symmetry-based strategy for assembling protein complexes," Rsc Advances, 2011, 1 (6), 1004-1012.) which are incorporated herein by reference. Glutamic acid 54 (E54 or Glu54), a solvent-exposed residue on the outer edge of the trimer, was selected as a suitable site for modification with DNA. This residue was mutated to cysteine (E54C) in order to carry out thiol-selective chemistry with the heterobifunctional crosslinker succinimidyl 3-(2-pyridyldithio)propionate (SPDP) and a 5'-amino modified oligonucleotide (FIG. 2C). Wild-type ald possesses four cysteine residues, but these are involved in disulfide bonds in the protein interior (FIG. 7A) therefore it appear that one may be able to selectively target the mutagenically-introduced C54 on the surface (for details regarding the expression, purification, and characterization of the E54C mutant protein see FIGS. 7A-7E).

Modification of the Aldolase Trimer with DNA—

Figures 9A, 9B, 9C, 9D, 9E:
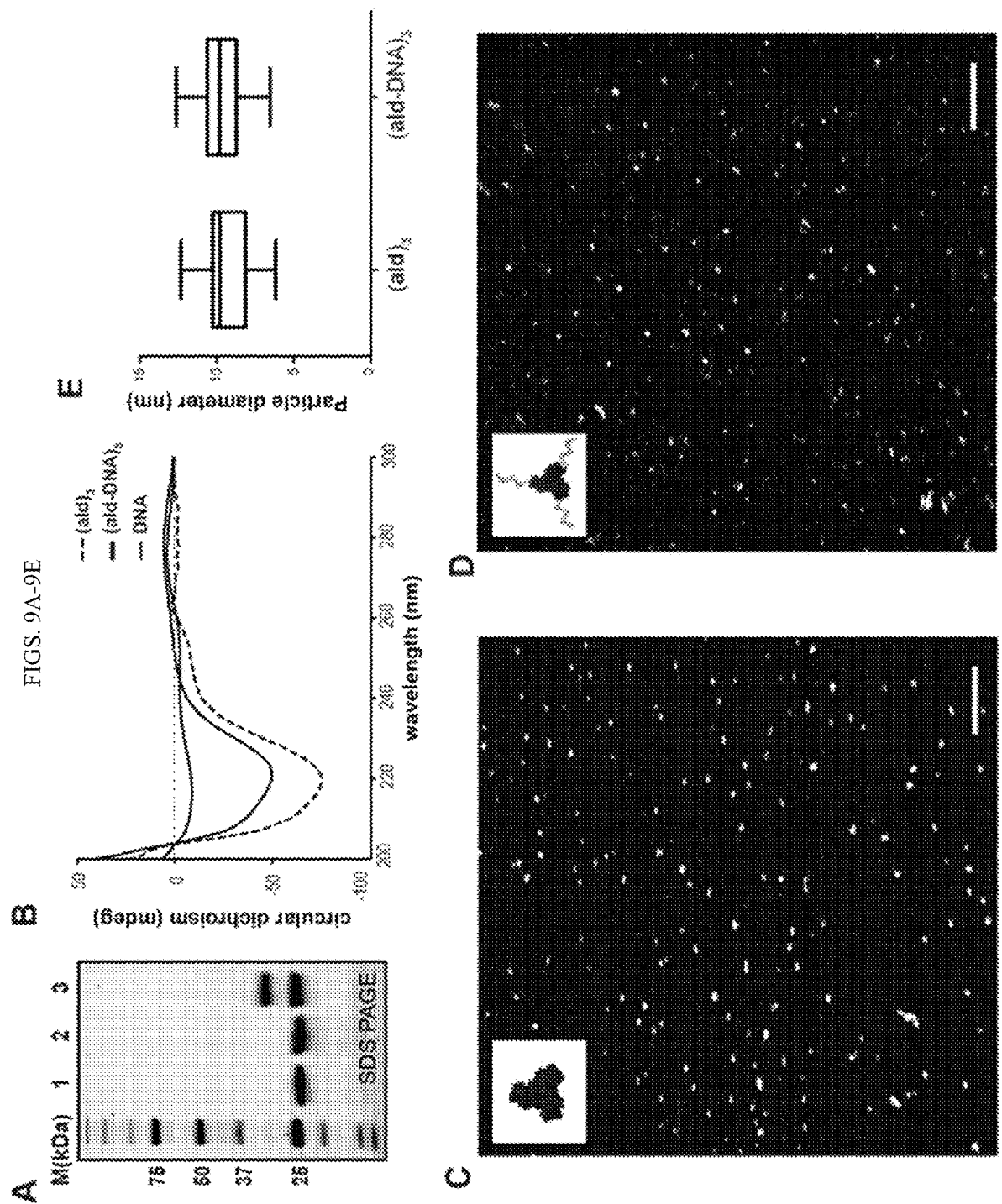
FIGS. 9A-9E show aldolase-DNA conjugation using the SPDP crosslinker.

Following exposure to 6 equivalents of purified SPDP-DNA (21 nt in length), a band with higher retention was observed by denaturing polyacrylamide gel electrophoresis (SDS-PAGE), corresponding to the ald monomer linked to the oligonucleotide, to approximately 50% yield (for reaction conditions and analysis see FIGS. 8A-8B and 9A-9E). Control experiments with wild-type protein did not show this upper band, suggesting that the native cysteines were unreactive under these conditions (FIG. 9A). The mild coupling conditions were not expected to disrupt the protein-protein interactions holding the three monomers together, therefore anion exchange chromatography was used to isolate the ald trimer with three DNA handles (referred to hereafter as $(ald-DNA)_3$) from trimers bearing two or fewer oligonucleotides (FIGS. 8A-8B). The complete modification of purified $(ald-DNA)_3$ was verified by SDS-PAGE, which showed only a band corresponding to the DNA-modified ald monomer, with lower mobility than the unmodified ald (FIG. 2D).

Then it was probed whether the trimer-linked DNA handles could bind their complementary strand using native, non-denaturing PAGE (FIG. 2E). The unmodified $ald_3$ (lane 1) in Tris buffer has a net charge of −12.2 (pI=6.9), so upon modification with three anionic DNA handles, it migrates farther towards the positive terminal of the gel (lane 2). Addition of ssDNA complementary to the handles results in a reduction of gel mobility due to the increased size of the complex (lane 3), whereas non-complementary DNA does not shift the $(ald-DNA)_3$ band (lane 4). To verify that the increased mobility in lane 2 was not due to the trimer dissociating into monomers after DNA conjugation, the samples were analyzed by AFM (FIGS. 2F and 2G). Both unmodified $ald_3$ and the $(ald-DNA)_3$ conjugate showed roughly circular structures with similar heights: ~3 nm, in good agreement from the predicted height measured from the crystal structure. The measured diameter of the $ald_3$ (6.5 nm) corresponded well with the crystal structure, whereas the $(ald-DNA)_3$ had a slightly larger diameter (10 nm) than the wild type ald which may be due to the appended oligonucleotides, but clearly demonstrated that the trimer had not dissociated into monomers as a result of the DNA conjugation. Based on all these data, it appears pure samples of the ald trimer modified with three ssDNA handles were produced, and that these handles were still functional for sequence-specific hybridization with a complementary oligonucleotide.

Experiments with Model DNA Nanostructures—

In order to test the ability of the trivalent $(ald-DNA)_3$ conjugate to organize DNA structures, a model nanostructure that could be directly imaged by AFM was synthesized. A rigid tile including two parallel DNA helices linked by four crossover points was designed, with single-stranded regions for the $(ald-DNA)_3$ handles to bind as a fifth crossover point (FIG. 3A; for tile design and characterization see sequences below and FIGS. 10A-10E).

```
Sequences of multi-crossover ("MX") tile DNA
strands (5'→3')
T1
                                 (SEQ ID NO: 18)
GAGCAGACCTAGCGGACTTGGGTAAACCGTATAAAGGCTATGTTGCACTCA

CGGACCGATGCTCCTCACCACTTCAGTTGGGCAACGGCCTAAGGGCTTG

T2
                                 (SEQ ID NO: 19)
GAGTTCCGTCAGGTCTGCTC

T3
                                 (SEQ ID NO: 20)
CAAGTCCGCTCGGCATCTGGGTCCCATAAGGTACGGTTTACC

T4
                                 (SEQ ID NO: 21)
AGACGGGCGAGTGAGTGCAACATAGCCTTTAAGCACACCAGG

T5
                                 (SEQ ID NO: 22)
GCATCGGTCCCGAGCTAACAACGCGGAACCTAGTGGTGAGGA

T6
                                 (SEQ ID NO: 23)
GTATATGCTCCTTAGGCCGTTGCCCAACTGATCAGAGAGGGT

T7
                                 (SEQ ID NO: 24)
TTTTCAAGCCCGGAGCTTTT

T8
                                 (SEQ ID NO: 25)
GCTCCGGAGCATATACACCCTCTCTGAAGGTTCCGCGTTGTTAGCTCGTCG

CCCGTCTCCTGGTGTGCTCCTTATGGGACCCAGATGCCGGACGGAACTC
```

Figures 3A, 3B, 3C, 3D, 3E, 3F:
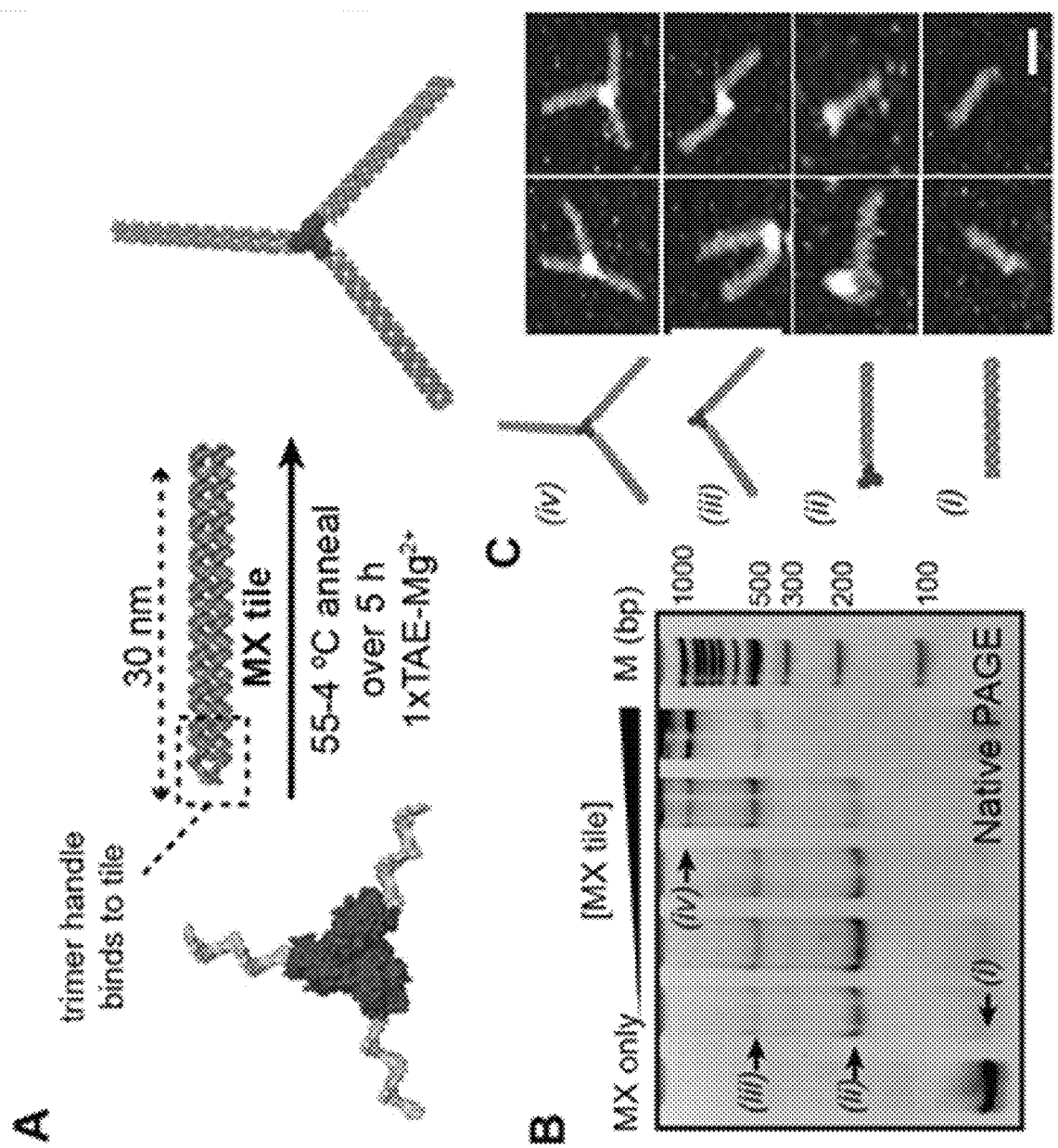
FIGS. 3A-3F show protein assembly with DNA nanostructures.
Figures 3A, 3B, 3C, 3D, 3E, 3F:
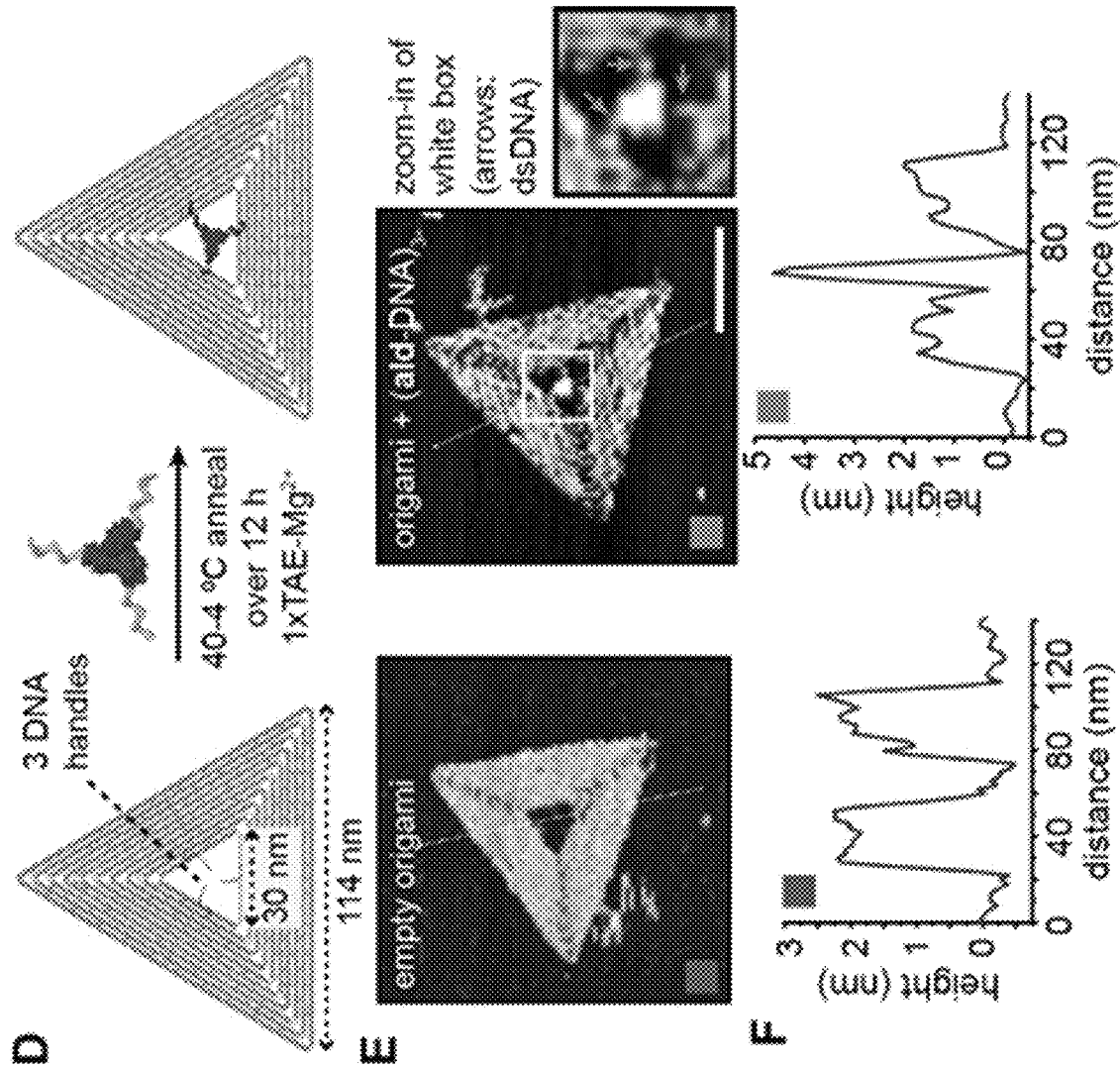
Figures 10A, 10B, 10C, 10D, 10E:
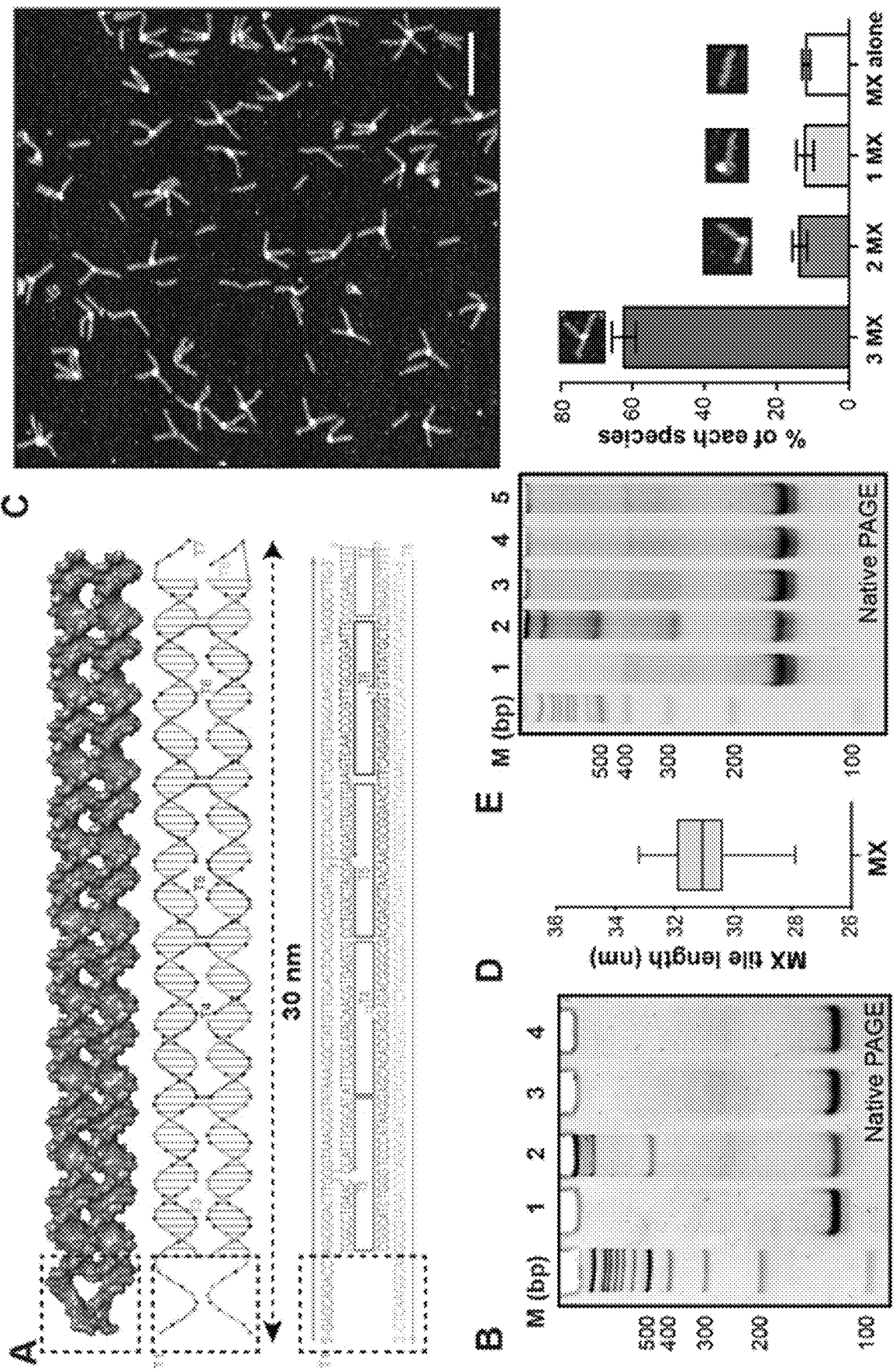
FIGS. 10A-10E show MX tile design and assembly with (ald-DNA)$_3$.

This multi-crossover ("MX") tile is 4 nm wide and 30 nm long, large enough to unambiguously image using AFM. Combining the tile with the (ald-DNA)$_3$ conjugate may yield up to three tiles linked to the (ald-DNA)$_3$ hub in a radial arrangement (FIG. 3A). Indeed, annealing the preformed and purified MX tile with (ald-DNA)$_3$ from 55 to 4° C. over 5 hours in 1×TAE-Mg$^{2+}$ buffer resulted in several distinct bands by native PAGE (FIG. 3B), with a shift towards higher bands with increasing concentration of the tile relative to (ald-DNA)$_3$. Each of these bands from the gel were purified and imaged by AFM, and they corresponded to (in order of decreasing mobility): the unmodified MX tile, and (ald-DNA)$_3$ bound to one, two, and three tiles, respectively (FIG. 3C). The length of the tiles in FIG. 3C measured 31±1.4 nm by AFM, which is in good agreement with the design (FIG. 10D). Because the DNA handles are chemically linked to ald at a single site via a hydrocarbon linker, the attachment is quite flexible, so the angles between the MX tiles and the protein vary greatly (FIGS. 10A-10E). However, the number of tiles could be readily visualized for each band, and the presence of a major band with three tiles at higher concentrations of the tile shows that the (ald-DNA)$_3$ does not dissociate even with several large DNA structures attached. The highly stable trimer protein was able to withstand annealing from 55° C., making it attractive as a building block for these hybrid materials. Control experiments with mismatched handles resulted in no association of the protein with the tiles (FIG. 10B), confirming that the binding was mediated by DNA hybridization. At lower temperatures, the MX tile associated with (ald-DNA)$_3$ was not efficient (FIG. 10E), highlighting the importance of the homotrimer stability to higher temperatures.

The binding of (ald-DNA)$_3$ to a triangular DNA origami structure with a cavity bearing three complementary handles (FIG. 3D and FIGS. 11A-11C) was also explored. Compared to the empty origami, annealing of (ald-DNA)$_3$ to the scaffold resulted in a circular structure in the center, ~10 nm in diameter and 3 nm in height (FIGS. 3E and 3F, FIG. 11B, and FIGS. 12A-12B), comparable to the dimensions of the (ald-DNA)$_3$ (FIG. 2G). Furthermore, in many images, the three DNA duplexes linking the trimer to the origami could be directly visualized (FIG. 3E, zoom-in blue arrows), further confirming its ability to bind in a trivalent fashion. As with the MX tiles, control experiments with mismatched handles resulted in origami cavities lacking protein (FIG. 10B). A trimeric protein like ald provides an attractive candidate for the scaffolding for the immobilization of other materials (including fusion proteins), so integrating it with DNA origami provides the potential for hierarchical organization of molecules. Potential applications for these multi-scale, hybrid biomolecular scaffolds including targeted delivery of medicinal species, light harvesting and artificial photosynthetic systems, or structural biology by using DNA origami as a fiducial marker to visualize proteins in techniques such as cryo-electron microscopy.

Only about 70% of origami contained well-positioned proteins in the center. Samples where the protein seemed to be "off-center" (perhaps bound by fewer than three handles) were not counted. Despite screening a number of sequences and annealing conditions, higher yields were not obtained, perhaps due to incomplete incorporation of handles, or electrostatic repulsion between the (ald-DNA)$_3$ and the origami structure.

Self-Assembly of Hybrid Tetrahedral Cages—

Figures 4A, 4B, 4C, 4D, 4E, 4F:
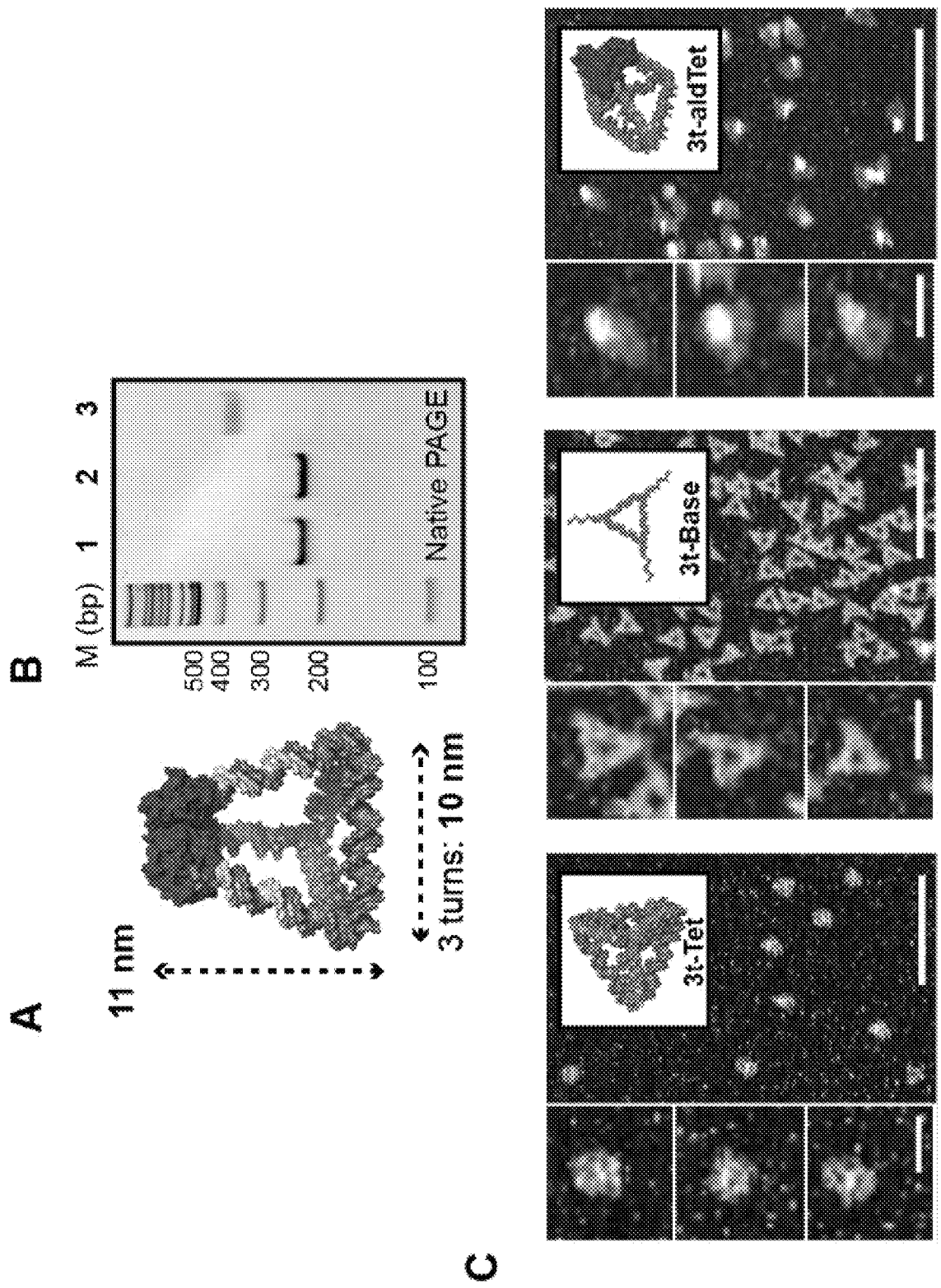
FIGS. 4A-4F show protein-DNA tetrahedral cages.
Figures 4A, 4B, 4C, 4D, 4E, 4F:
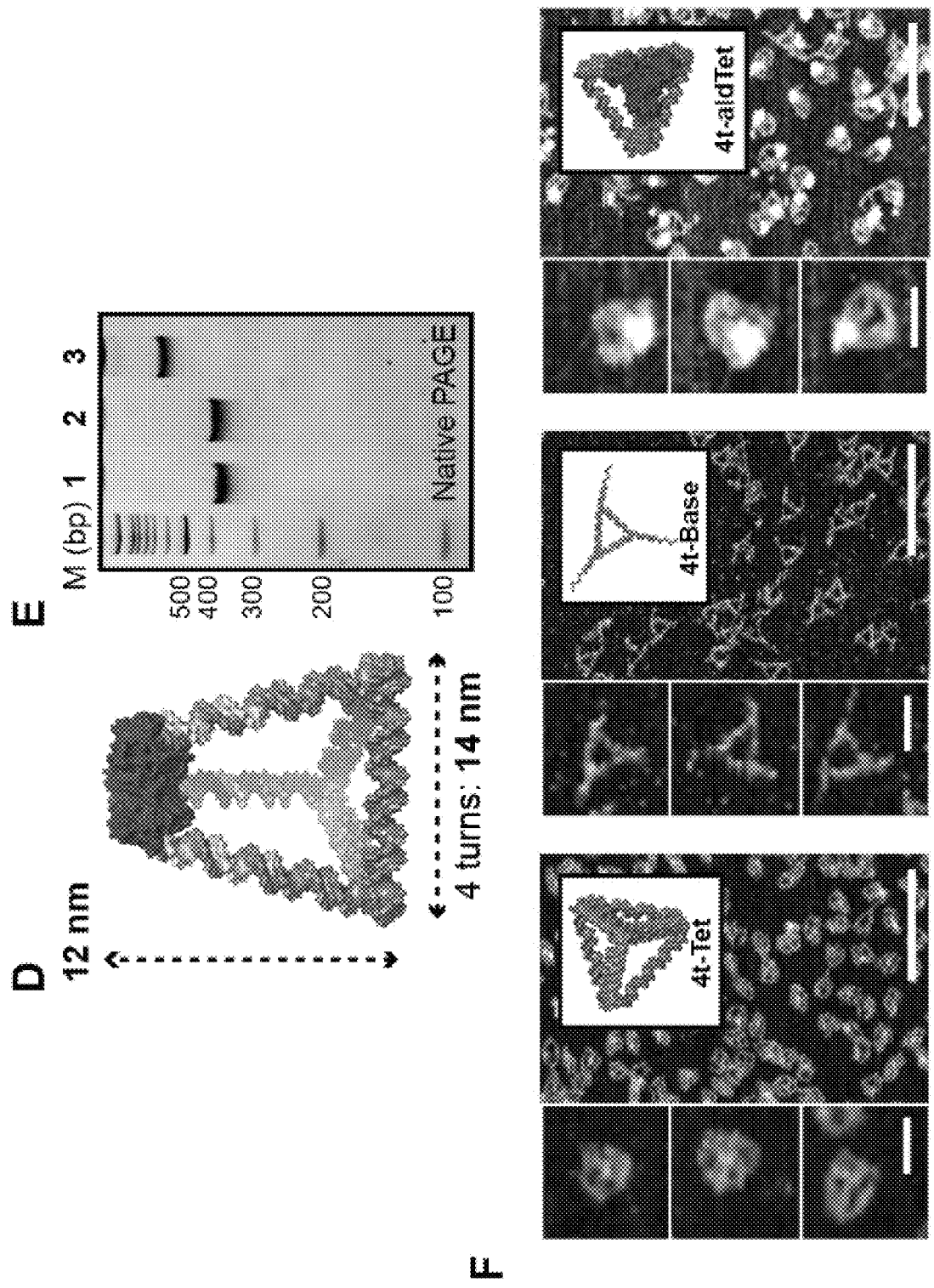

The (ald-DNA)$_3$ could reliably bind three complementary oligonucleotide strands and organize large DNA assemblies, and the next step was to make the hybrid tetrahedral protein-DNA cages outlined in FIG. 1C. A cage was designed with three helical turns of DNA (31 bp) for each of its six edges, to yield a structure with predicted dimensions of 10 nm per side and 8 nm in height (FIG. 4A). The base of the scaffold was constructed as previously shown in FIG. 1B, with three turns of DNA per side and three arms consisting of one turn of dsDNA extended with three identical 21-nt ssDNA. Hybridization of these handles to the complementary handles on (ald-DNA)$_3$ results in three helical turns for each of the three protein-linked edges in turn. This three-turn triangular base is referred to as 3t-Base (sequences below, full design shown in FIGS. 13A-13E).

DNA strand sequences for tetrahedral cage design (5'→3'):

```
Sequence conjugated with aldolase protein
THS1
                                         (SEQ ID NO: 46)
TGAGTTCCGTCAGGTCTGCTC Strands for 3t-Base (three-turn triangular base)
T3S2
                                         (SEQ ID NO: 26)
TAGATGATAGCTAGATAGTAGATAGTAGAAGAGATAGATAGATATGCGATC

GATCGGAGCAGACCTGACGGAACTCA

T3S3
                                         (SEQ ID NO: 27)
CGATCGATCGCTATAGATAGTAGATAGATGATAGATGAGATGAGTCGATCG

TAGCTGAGCAGACCTGACGGAACTCA

T3S4
                                         (SEQ ID NO: 28)
AGCTACGATCGTTAGATAGATGAGAGAGAAGATAGAGAGATAAGTGCTATC

ATCTAGAGCAGACCTGACGGAACTCA

T3S5
                                         (SEQ ID NO: 29)
CTACTATCTACTATCTACTTATCTCTCTATCTTCTCTCTCATCTATCTATC

TCATCTCATCTATCATCTATCTACTATCTATCTATCTATCTATCTCTT

Strands for 3t-Tet (three-turn all-DNA tetrahedron)
TC3S1
                                         (SEQ ID NO: 30)
GTCTGAGGCAGTTGAGAGATCTCGAACATTCC TC3S2
                                         (SEQ ID NO: 31)
TAAGTCTGAAGATCCATTTATCACCAGCTGCTGCACGCCATAGTAGACGTA

TCACCTGTCC

TC3S3
                                         (SEQ ID NO: 32)
CAGCTGGTGATAAAACGTGTAGCAAGTAGCTTTGATCTGTAATCGACTCTA

CGGGAAGAGC

TC3S4
                                         (SEQ ID NO: 33)
CAGCTGGTGATAAAACGTGTAGCAAGTAGCTTTGATCTGTAATCGACTCTA

CGGGAAGAGC

TC3S5
                                         (SEQ ID NO: 34)
ATGCCCATCCGGCTCACTACTATGGCGTGCAG

TC3S6
                                         (SEQ ID NO: 35)
CGAGTCCTCGCATGACTCAACTGCCTCAGACGGACAGGTGATACGAGAGCC

GGATGGGCATGCTCTTCCCGTAGAGATAGTACGGTATTGGAC
```

-continued

Strands for 4t-Base (four-turn triangular base)

T4S2
(SEQ ID NO: 36)
GAGCAGACCTGACGGAACTCAAGGAGTGTGATGGAGATTTATTTTGAGAGA
GAAGATAGAGAGATAAGAGATAGATAGATAGATAGATTTTCCGTGTAGTGT
TCAACGCCT

T4S3
(SEQ ID NO: 37)
ATCTCTCTATCTTCTCTCTCTTACTATCTACTATCTACTTATCTCTCTATC
TTCTCTCTCATCTCTCATCTCATCTATCATCTATCTACTATCTATCTATCT
ATTCTTCTATCTATCTATCTATCTCTT

T4S4
(SEQ ID NO: 38)
GAGCAGACCTGACGGAACTCAAGGCGTTGAACACTACACGGATTTGAATAG
ATAGATAGATAGTAGATAGATGATAGATGAGATGAGTTTCTCTCGTAGTTA
ACATCTAGC

T4S5
(SEQ ID NO: 39)
GAGCAGACCTGACGGAACTCAGCTAGATGTTAACTACGAGAGTTTGATGAG
AGAGAAGATAGAGAGATAAGTAGATAGTAGATAGTATTTATAAATCTCCAT
CACACTCCT

Strands for 4t-Tet (four-turn all-DNA tetrahedron)

TC4S1
(SEQ ID NO: 40)
CATCACATTACCATTACCTACTCATTACCCTTACATCCAACATCATTCACA
TCTATACCTACACTAACCTTACCTACATTACCTATCACTACCACTCTCCTC
ATTACCTAACCTACATCCAC

TC4S2
(SEQ ID NO: 41)
AATGTAGGTAAGGTTAGTGTTGACGACGGAGAGGTTCTTAATACTTCAAGT
GAAATGTTTTTTAAACAGGTTTGGTAGGTG

TC4S3
(SEQ ID NO: 42)
CACGGACTCTGTCGTATACATGGAGAGTGGTAGTGATAGGT

TC4S4
(SEQ ID NO: 43)
GACTGGAGTGTAATCGCTAGTGGTAATGGTAATGTGATGAGTGGATGTAGG
TTAGGTAATGTTGTATACGACAGAGTCCGTGCACCTACCAAACCTGTTTAA
TATAGCGAACGATTATAATGA

TC4S5
(SEQ ID NO: 44)
TGGATGTAAGGGTAATGAGTTCTAGCGATTACACTCCAGTCTCATTATAAT
CGTTCGCTATTAAAACATTTCACTTGAAGTA

TC4S6
(SEQ ID NO: 45)
TTAAGAACCTCTCCGTCGTCTGGTATAGATGTGAATGATGT

For comparison, an all-DNA tetrahedron with three helical turns edge was designed, 3t-Tet (FIG. 18A).[33] Both 3t-Tet and 3t-Base were self-assembled via thermal annealing, purified by native PAGE (FIG. 4B and FIGS. 14A and 14B), and imaged via AFM (FIG. 4C and FIGS. 15A-15C). The images show well-formed, cage-like particles with a triangular base and six edges for 3t-Tet, with an average height of 5 nm, and an average edge length of 11 nm (see FIGS. 18A-18E for size distributions of all particles from AFM). The height measurement is slightly shorter than predicted from the structure design, indicating that the cages are flexible and deform upon adsorption to the mica surface, whereas the edge measurements correlated closely with the intended 10 nm design. AFM imaging of 3t-Base showed open triangular structures on the surface, with three short arms. These particles had a smaller height than 3t-Tet (4 nm) but with a similar edge length of 11 nm, as expected.

Figures 14A, 14B:
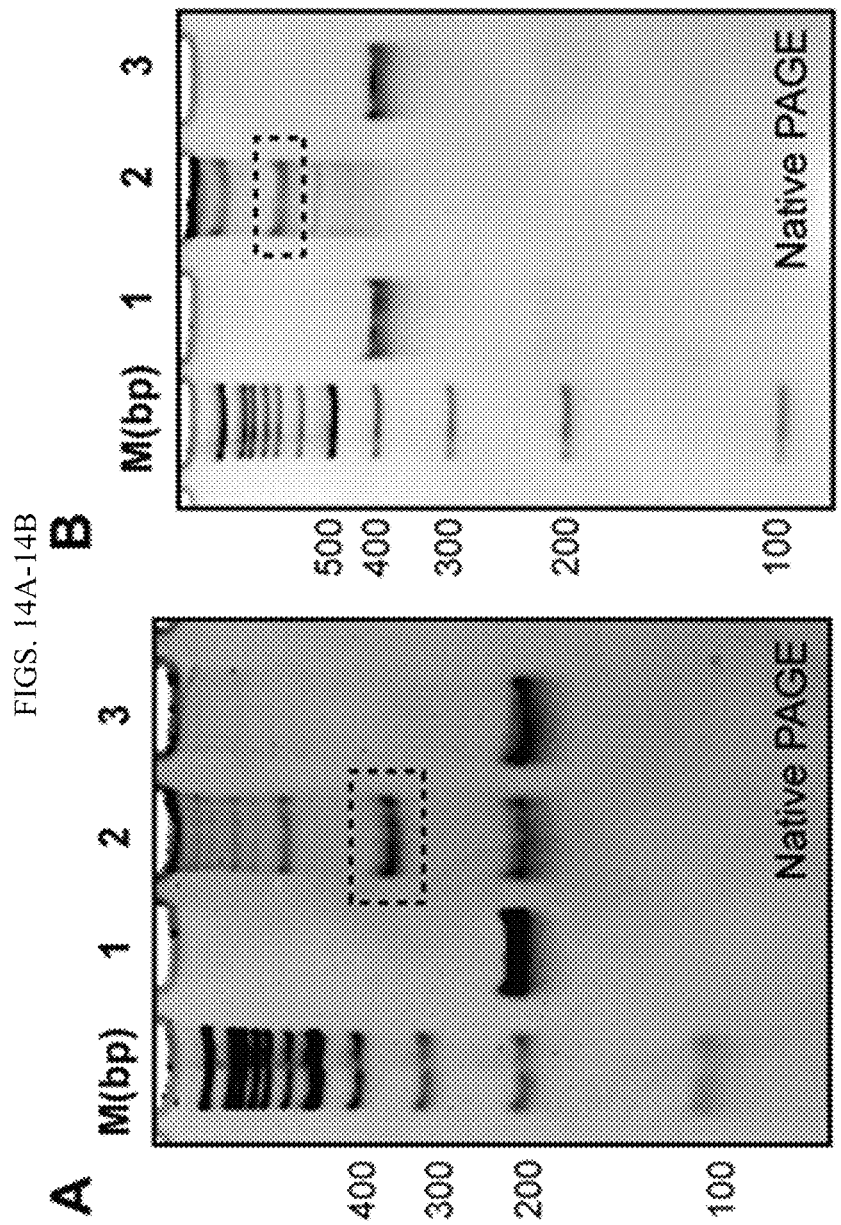
FIGS. 14A-14B show native PAGE of 3t-aldTet and 4t-aldTet self-assembly.
Figures 15A, 15B, 15C:
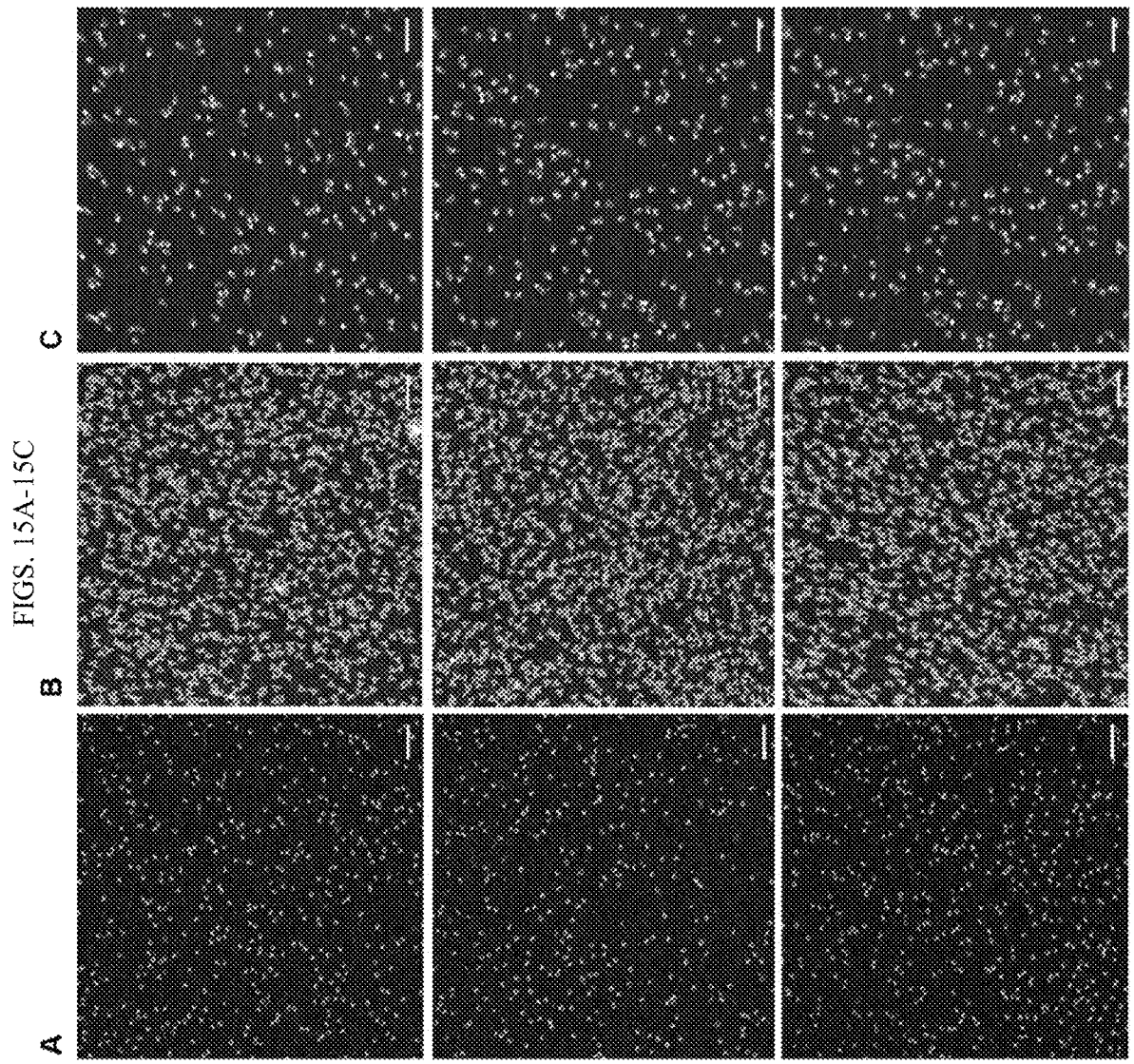
FIGS. 15A-15C show wide-field AFM images of three-turn samples.
Figures 16A, 16B, 16C:
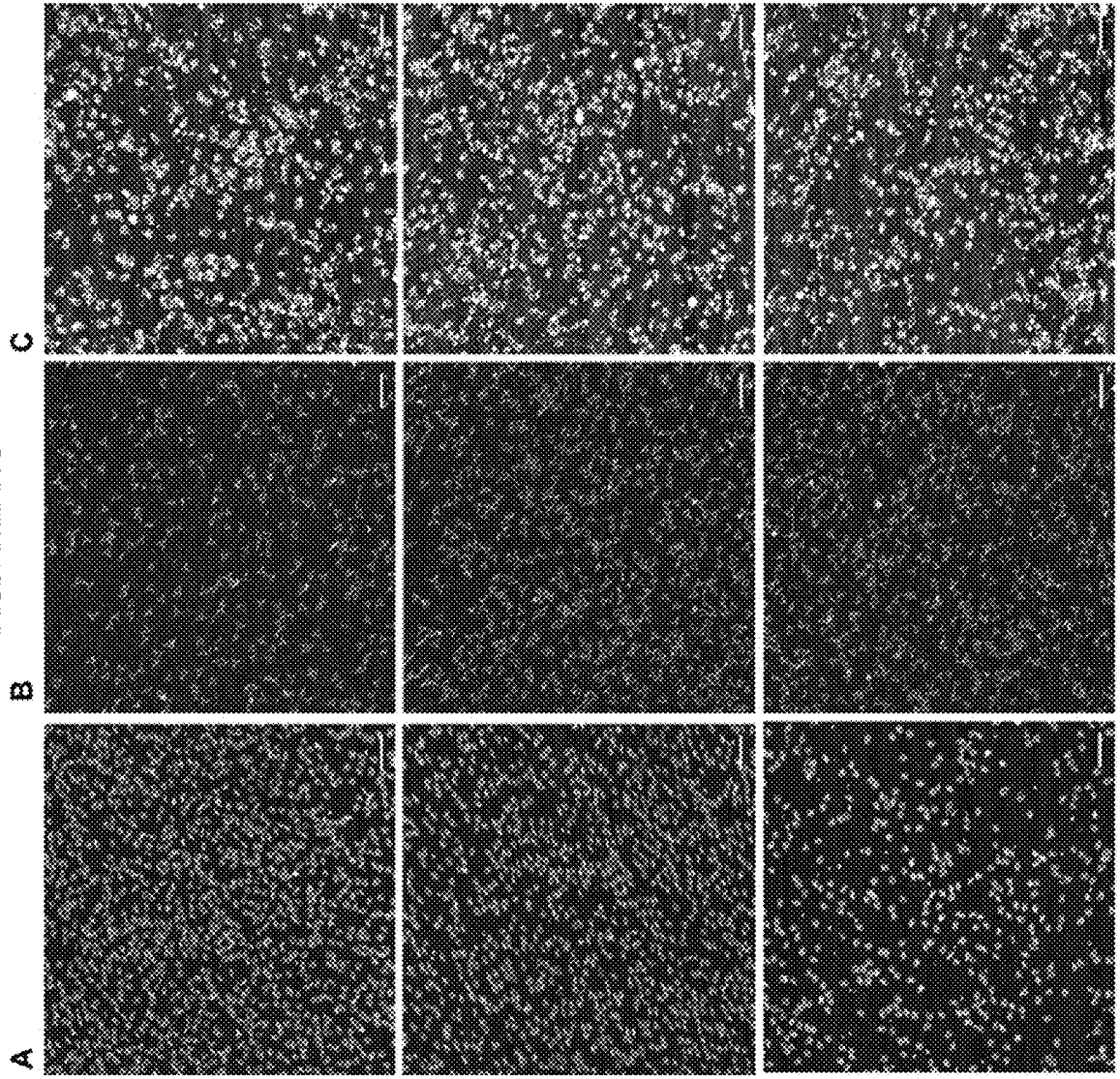
FIGS. 16A-16C show wide-field AFM images of four-turn samples.
Figures 17A, 17B, 17C:
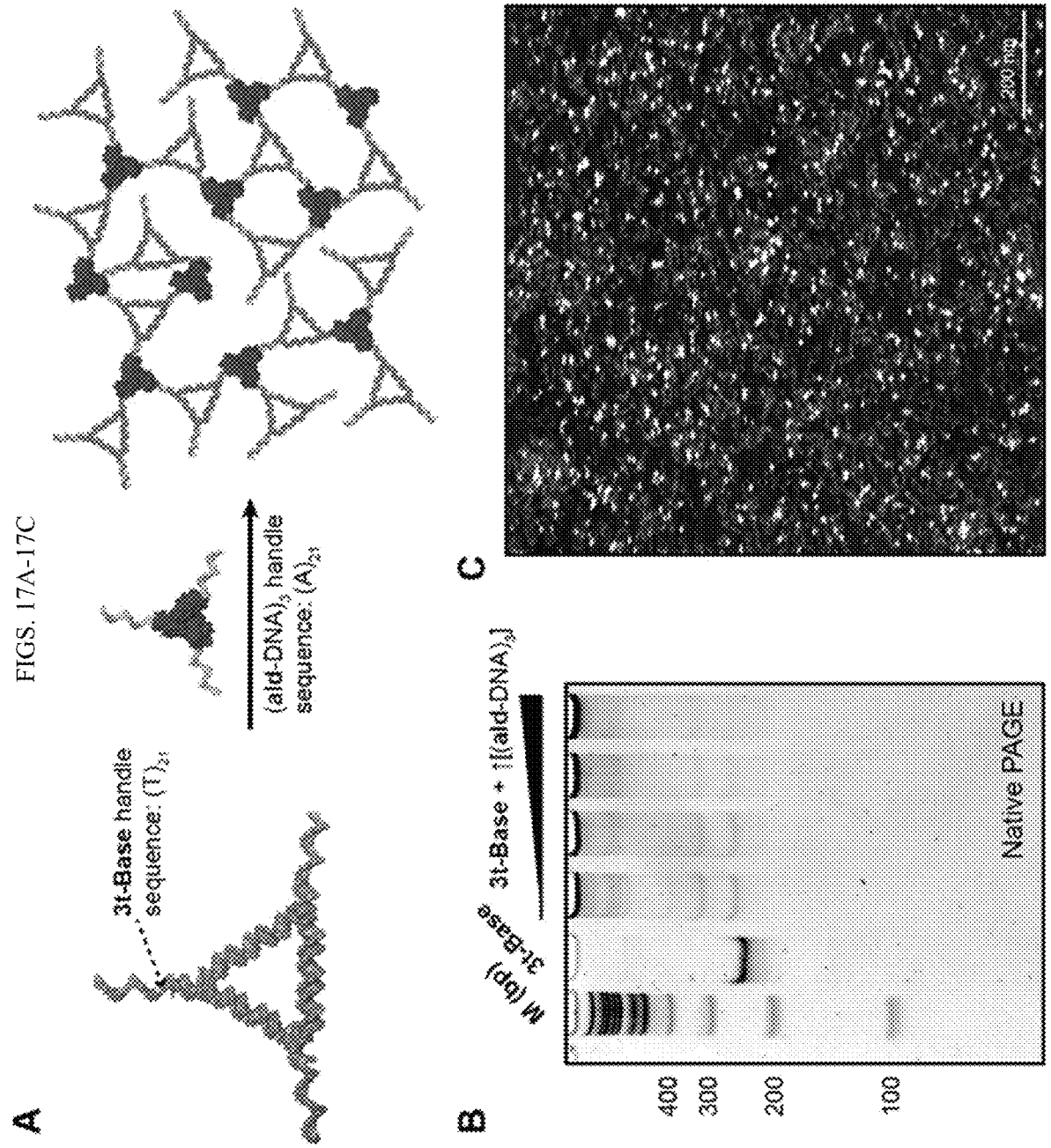
FIGS. 17A-17C show (ald-(A)$_{21}$)$_3$ self-assembly with 3t-Base((T)$_{21}$).
Figures 19A, 19B, 19C, 19D, 19E:
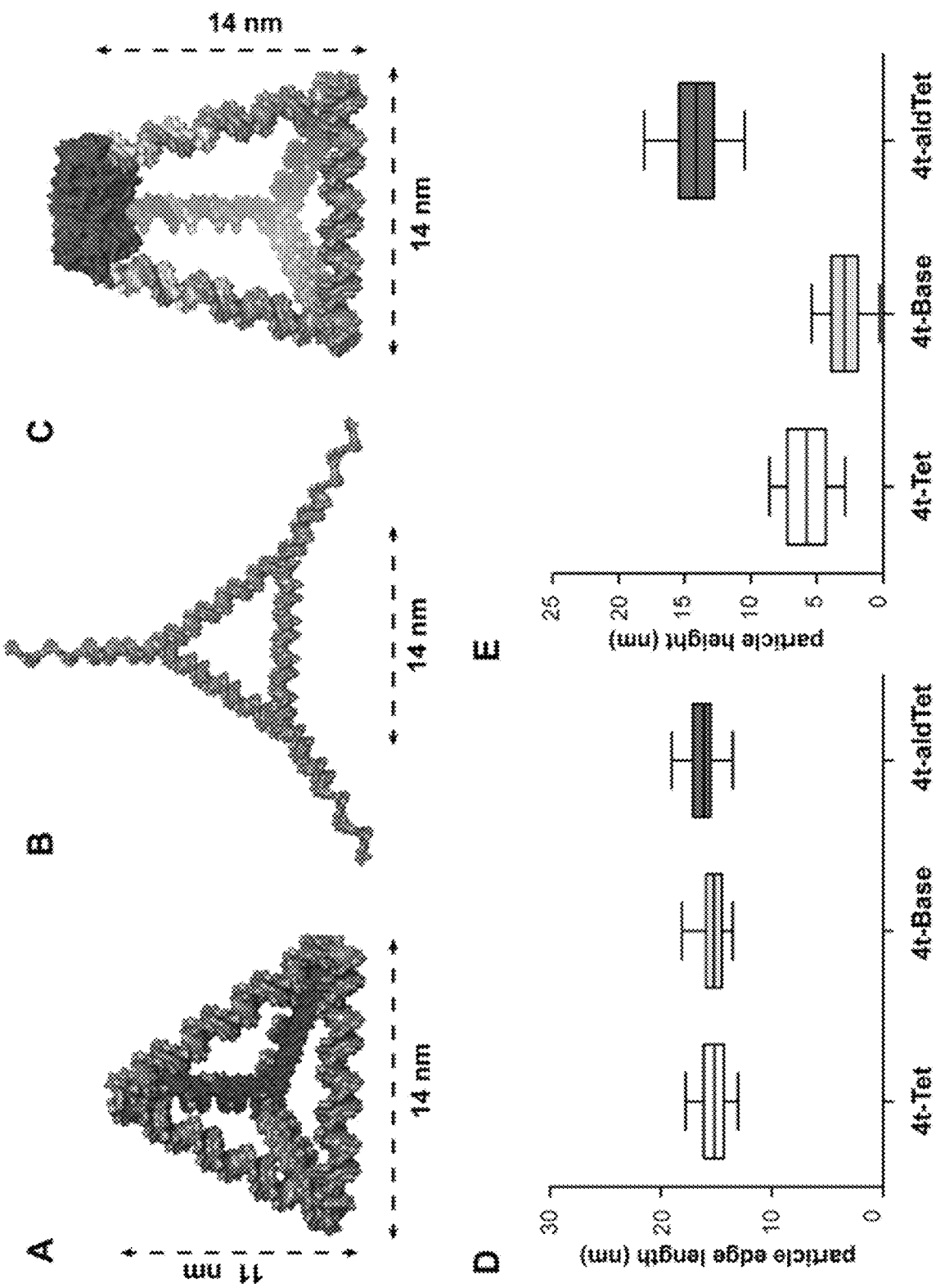
FIGS. 19A-19E show edge length and height measurements for four-turn samples.

Annealing of (ald-DNA)$_3$ with the 3t-Base yielded a distinct, lower-mobility band by native PAGE (FIG. 4B and FIGS. 14A-14B), due to the larger molecular weight of the three-turn protein-DNA tetrahedron (3t-aldTet). AFM imaging (FIG. 4C) showed compact structures with a white circular object at a vertex with straight edges and sharp corners, and in some images one or two of the arms connecting the top to the base can be directly visualized. The full triangular supporting DNA platform could not be seen due to the small size of the structures and partial occlusion by the protein. The average height for 3t-aldTet was 6 nm, slightly larger than either 3t-Base or 3t-Tet, though still less than expected from the design, with an average edge length of 11 nm as designed. The 3t-aldTet particles are somewhat flexible and deform, or lie flat on the surface upon adsorption similar to 3t-Tet. The vast majority of particles in the purified 3t-aldTet sample were the desired cage structures, but a few particles were malformed, with only one or two arms of the triangular DNA anchor bound to the protein (FIGS. 15A-15C). This could be due to co-migration of these structures with the fully assembled cage, or breakage of the cage during the processing steps involved in sample extraction from the gel.

One of the key advantages of DNA, and a motivation for building hybrid materials, is the high degree of programmability that oligonucleotides afford. The dimensions of the DNA cage can be tuned independently of the protein component by extending the length of the constituent strands, whereas in an all-protein cage an entirely new building block would have to be used. To demonstrate the tunability of the DNA scaffold, a larger tetrahedral cage with four helical turns of per side was designed, which can assemble from a triangular base with arms containing two full turns of DNA followed by the 21-nt handles (FIG. 4D and FIGS. 19A-19E). This structure has predicted dimensions of 14 nm (width) and 12 nm (height), ~40% larger than the three-turn variant. The sequences of these handles were designed so that the same (ald-DNA)$_3$ conjugate may be used as was used for the three-turn system. A four-turn all-DNA tetrahedron (4t-Tet) was designed to compare with the triangular base (4t-Base) and the protein-DNA cage (4t-aldTet). All samples were prepared as indicated previously (FIGS. 4E and 4F and FIGS. 16A-16C).

The 4t-Tet samples showed the expected tetrahedral structure with dimensions suggesting flexibility and deformation on the surface (average height 5.7 nm, average edge length 14.8 nm). The structure, with four individual triangular cavities comprising the sides, and all six distinct edges are more evident with these larger cages compared with the 3t-Tet. Similarly, the 4t-Base consisted of a larger triangular structure with three longer arms (average height 4 nm, average edge length 15.3 nm). Annealing (ald-DNA)$_3$ with 4t-Base produced a lower-mobility band when visualized by AFM yielded structures containing a triangular base with a circular structure that corresponded to the protein. The average height of these particles was noticeably larger than 4t-Tet (13 nm), and closer to the expected value of 12 nm from the design. Unlike 3t-aldTet, which appears to collapse on the mica surface, the 4t-aldTet seems to be more rigid and resists this deformation, though the origin of this rigidity is unclear. The average edge length was 15 nm, quite close to the 14 nm expected from the design. The base of the cage, with the protein at the apex of the structure, is more evident in 4t-aldTet due to the larger size of the DNA structure relative to the protein. Similar to the three-turn system, the majority of the particles in the 4t-aldTet structure were well-formed, with a minor fraction of broken or malformed structures. For both the three-turn and four-turn structures, control experiments with triangular bases bearing mismatched sequences to the (ald-DNA)$_3$ handles showed no cage formation by PAGE (FIGS. 14A-14B).

Although the images in FIGS. 4C and 4F were encouraging that the desired protein-DNA cages were formed, their small size precluded unambiguous confirmation of the structure by AFM. Two things required further investigation: (1) that the structures possessed three double-stranded arms connecting the base to the protein trimer, and (2) that the triangular base was still intact. To investigate the first point, three-turn triangular bases bearing only one or two ssDNA handles complementary to the trimer were synthesized, with the remaining arms consisting of a single, blunt-ended helical turn (FIGS. 20A-20D). When annealed with (ald-DNA)$_3$ these structures did not yield structures like 3t-aldTet as evidenced by either PAGE or AFM. Rather, two or three distinct triangular bases attached to a central protein hub were seen instead (FIG. 20C), providing indirect evidence that all three arms of the base were bound to the protein in 3t-aldTet.

Figures 20A, 20B, 20C, 20D:
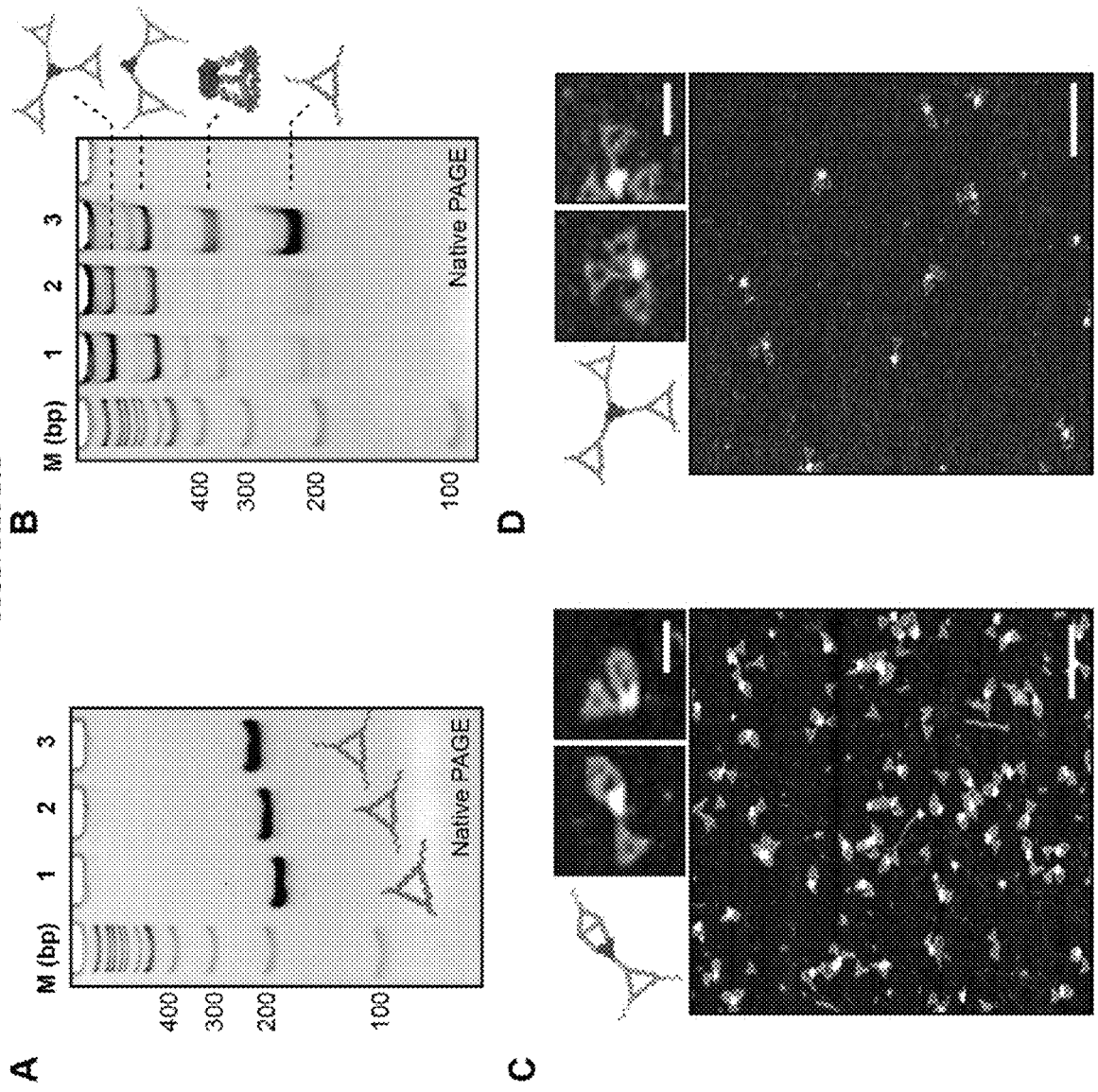
FIGS. 20A-20D show (ald-DNA)$_3$ assembly with 3t-Base bearing 1, 2, or 3 handles.
Figures 21A, 21B, 21C, 21D, 21E, 21F:
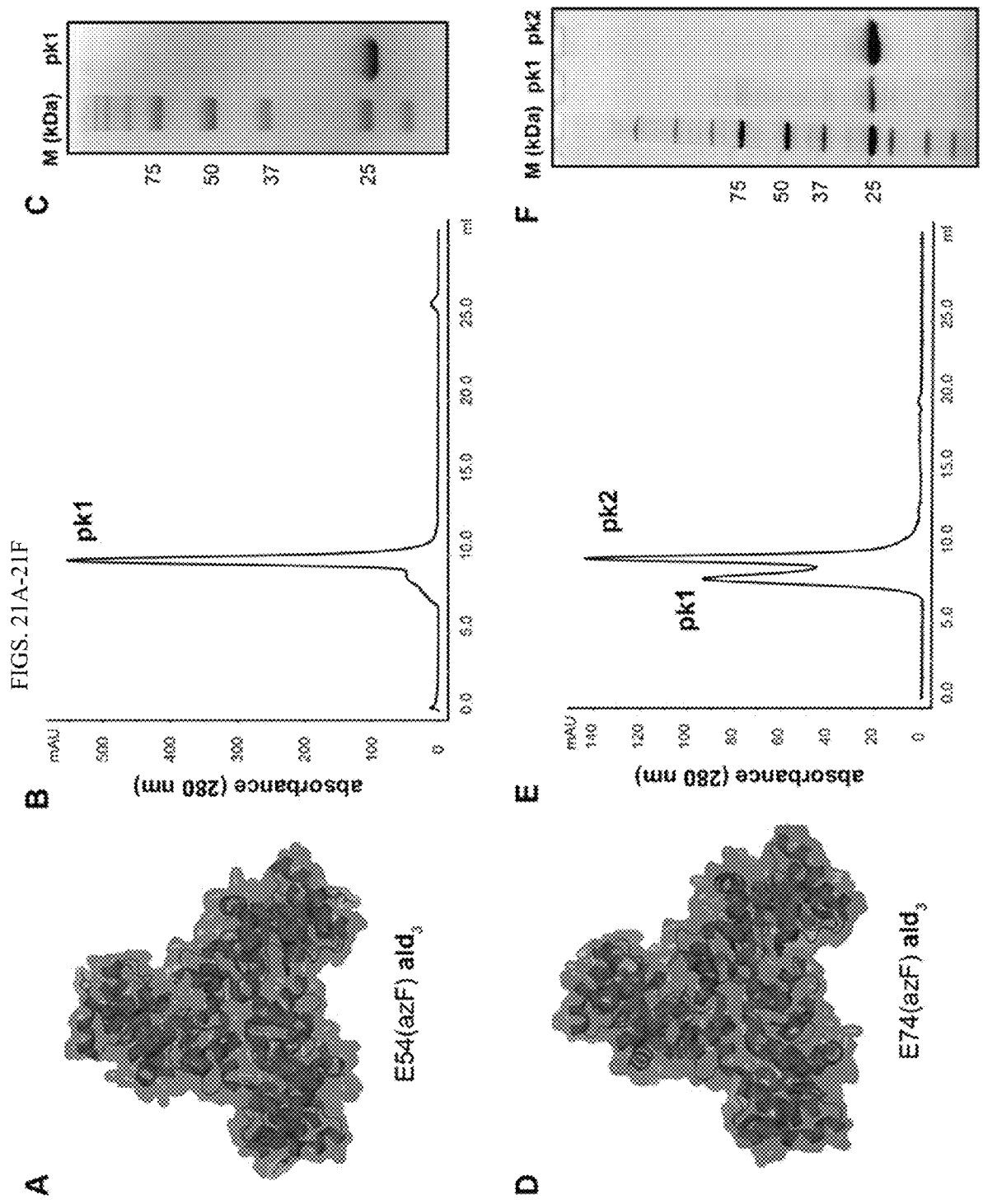
FIGS. 21A-21F show purification and characterization of azF-containing aldolase protein.
Figures 22A, 22B:
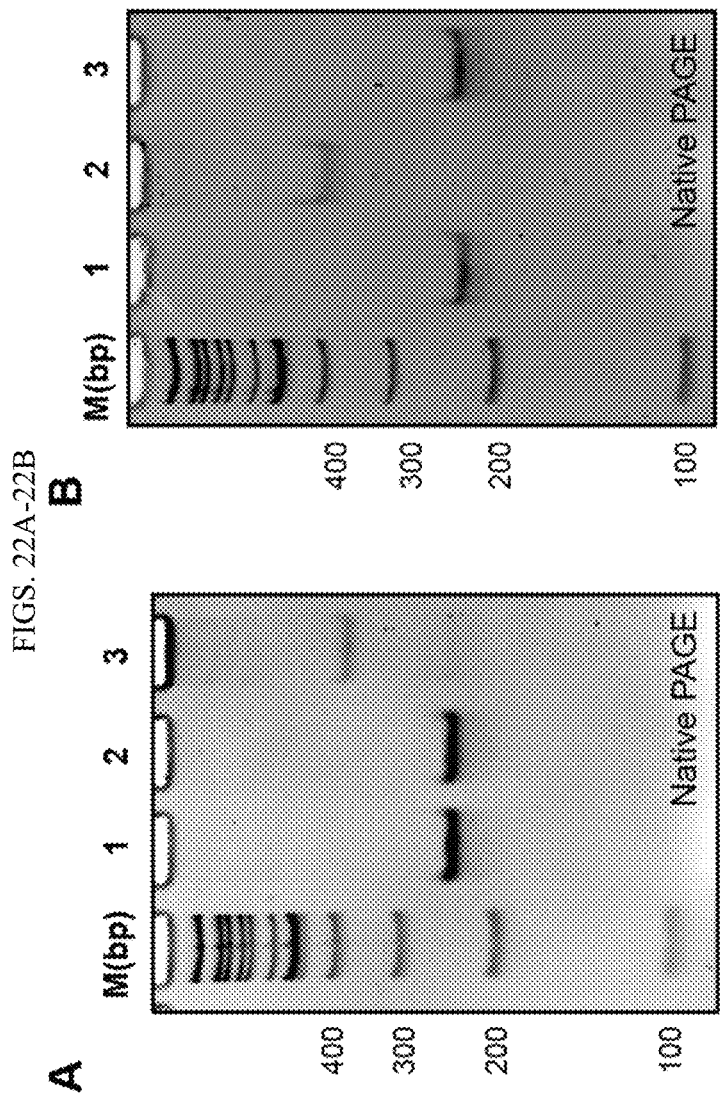
FIGS. 22A-22B show native PAGE of (ald-DNA)$_3$ with (azF) cage assembly.
Figures 23A, 23B, 23C, 23D, 23E, 23F:
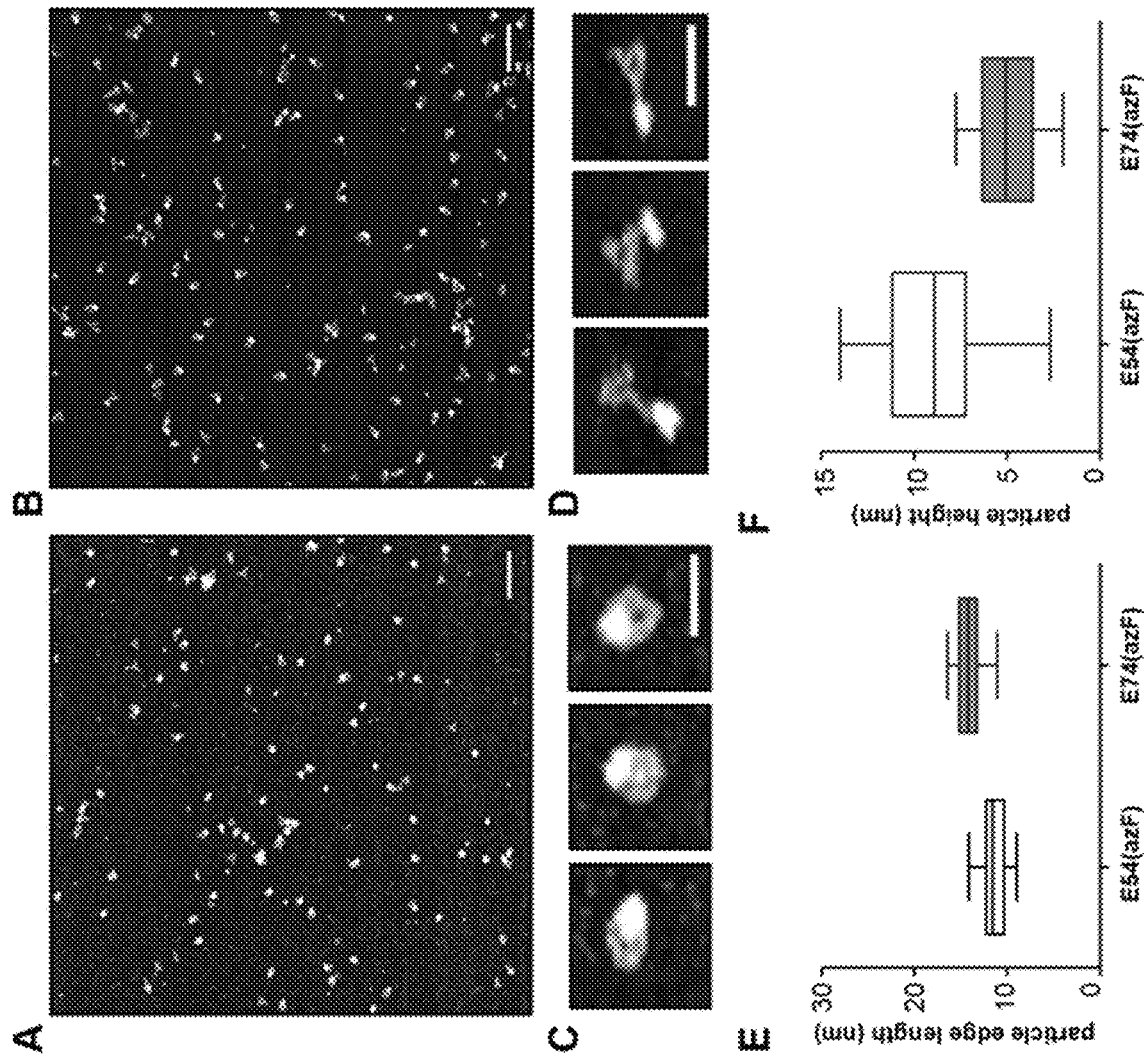
FIGS. 23A-23F show AFM analysis of protein-DNA cages with (azF)-aldolase.

As an indirect way to probe tetrahedral cage assembly, 3t-Base structures with only 1 or 2 arms bearing complementary handles to (ald-DNA)$_3$ as shown in FIG. 20A, were designed. Because these structures cannot form closed cages, they could be used to indirectly probe whether all three arms of the protein were bound to the base in the three-arm assemblies. By native PAGE and AFM (FIGS. 20A-20D) it is clear that with only 1 or 2 arms, the majority of structures are ald trimers bound to 2 or 3 different triangular bases. If the base has two arms, both can be bound to the protein (with a single additional base on the third arm, FIG. 20C, zoom-ins). With only a single arm, each base is attached to the trimer in only one location, leading to trimers with 2-3 bases each. The fact that 3t-Base samples with three arms show distinctly different structures (as in FIGS. 4C and 4F) suggests that in 3t-aldTet the protein does indeed have all three arms bound to the base. Otherwise, a second or third triangular base would have attached to the protein.

Figures 5A, 5B, 5C:
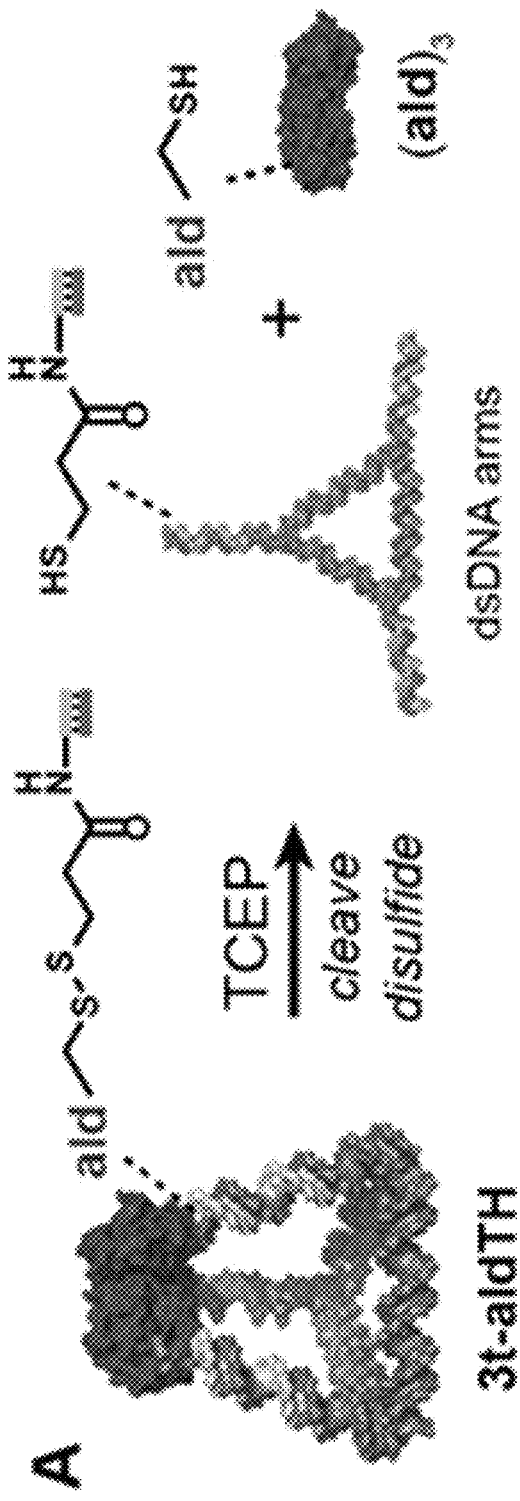
FIGS. 5A-5C show confirmation of 3D cage structure.

To further confirm that all three arms were bound to the protein, 3t-aldTet was exposed to the reducing agent tris(2-carboxyethyl)phosphine (TCEP), FIG. 5. The DNA handles on (ald-DNA)$_3$ are linked to the protein by a disulfide bond, so reduction of this linkage should yield a structure with three full turns of double stranded DNA per arm (FIG. 5A), as opposed to 3t-Base, which has only a single turn of dsDNA per arm. Indeed, treating 3t-aldTet with TCEP yielded a new band by native PAGE (FIG. 5B, lane 5), with a retention between the bands for 3t-aldTet (lanes 2 and 4) and 3t-Base (lane 4). This band had the same mobility as a sample of 3t-Base to which complementary oligonucleotides to the 21-nt handles were added in order to make them fully double-stranded (lane 3). Purification of the band in lane 5 from and imaging it by AFM clearly showed that it yielded the expected three-edge triangular platform (FIG. 5C), and the arms with three full helical turns appear longer than the 3t-Base arms in FIG. 4C. Taken together, these results suggest that the 3t-aldTet samples do indeed consist of a triangular base linked to the (ald)$_3$ by three double-stranded DNA arms. A faint lower band can be seen in both lanes 3 and 5 (marked by a red arrow), which is the 3t-Base with two double-stranded and one single-stranded arm. For lane 5, this band intensity corresponds to a minor fraction (~10%) of cages where only two of the arms are bound to the protein.

Site-Specific DNA Conjugation Using Non-Canonical Amino Acids—

Although the thiol-selective chemistry used for modification of ald is highly effective when site-specific bioconjugation with native amino acids is required,[45] many proteins have endogenous reactive cysteines that preclude this approach. Furthermore, it was found that the E54C ald$_3$ mutant was prone to aggregation due to spontaneous disulfide formation between Cys54 residues. This issue was circumvented by reducing the expressed protein with dithiothreitol (DTT) prior to conjugation, but the reaction conditions had to be carefully tuned to avoid breakage of the two internal disulfide bonds, which in turn led to overmodification with DNA. For a full discussion of protein aggregation and optimization of reduction conditions, see FIGS. 21A-21F, FIGS. 22A-22B, FIGS. 23A-23F, and FIGS. 24A-24B. To avoid these issues, it was determined whether the ald$_3$ could be modified with DNA using a chemical reaction completely orthogonal to native amino acids. For this purpose, the strain-promoted azide-alkyne cycloaddition (SPAAC), more commonly known as copper-free click chemistry, was selected. This reaction is selective, efficient, and has been used to conjugate DNA to peptides and proteins successfully.

Figures 6A, 6B, 6C, 6D, 6E, 6F:
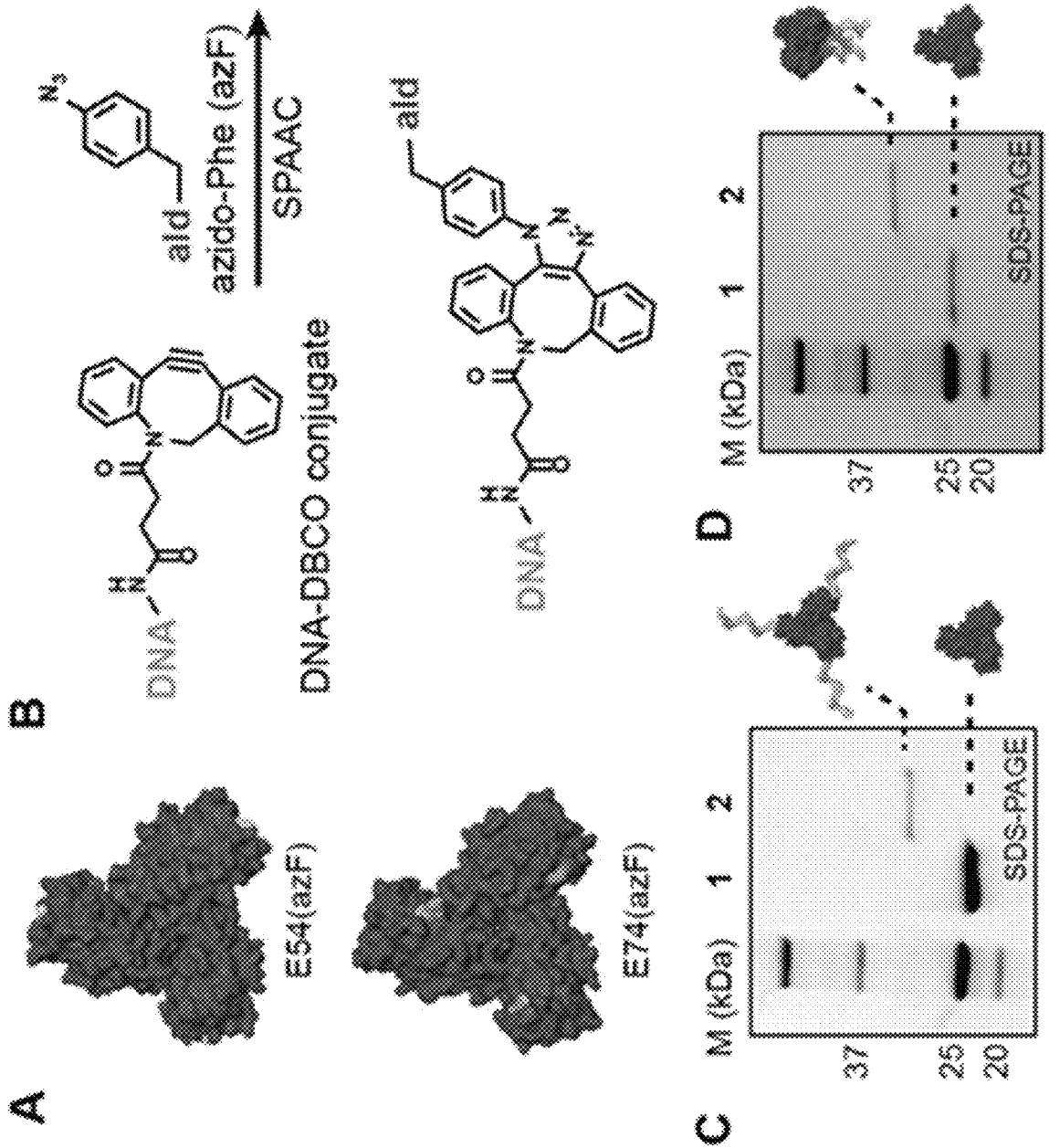
FIGS. 6A-6F show non-canonical amino acid cages.
Figures 6A, 6B, 6C, 6D, 6E, 6F:
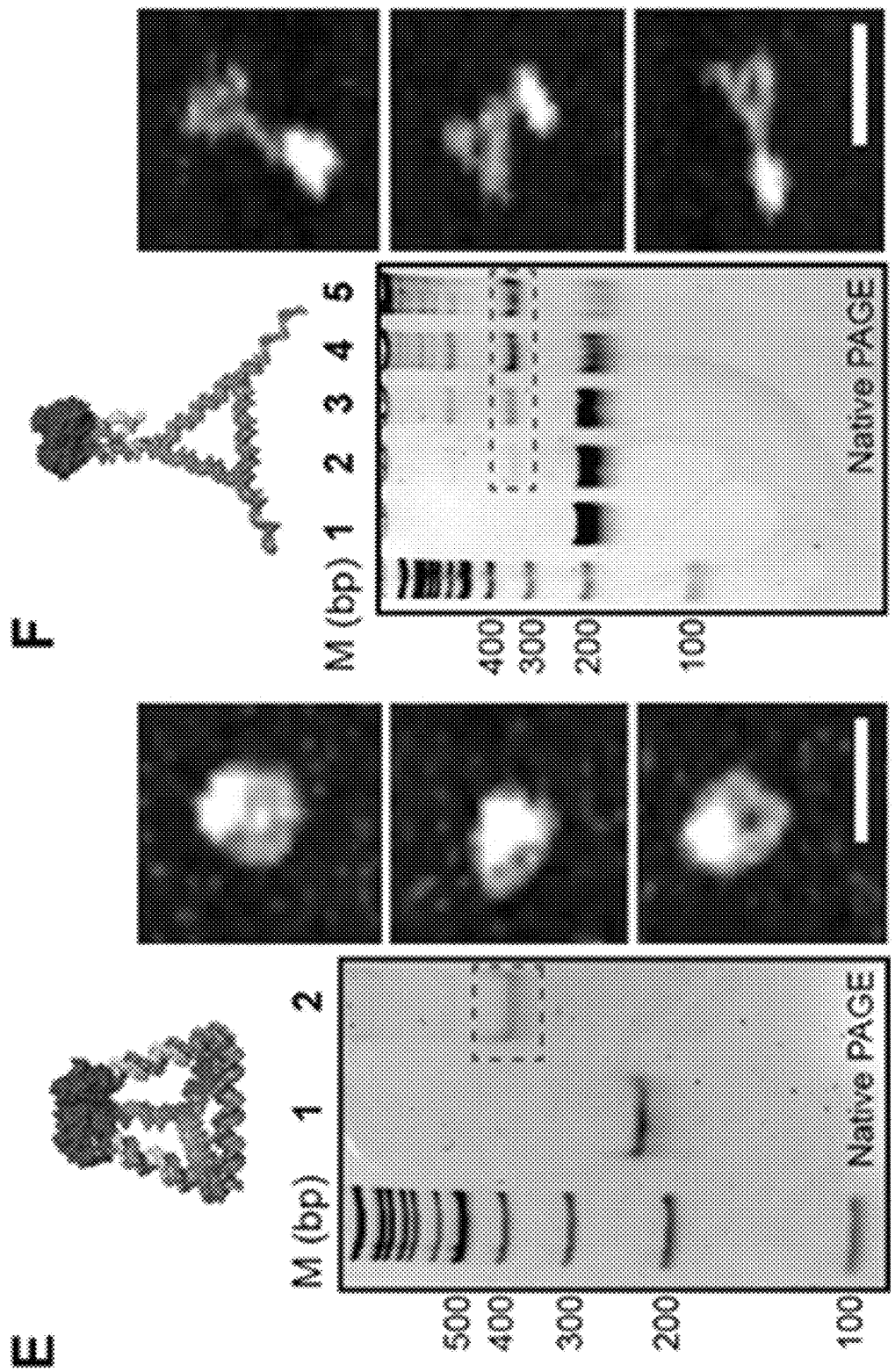
Figure 24A:
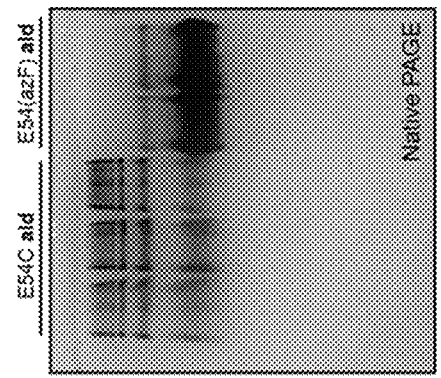
FIGS. 24A-24B show cysteine vs. 4-azidophenylalanine bioconjugation strategies.

The non-canonical amino acid 4-azidophenylalanine (azF) was introduced into ald, creating the E54(azF) mutant via the Schultz amber codon suppression method (FIG. 6A; for details of protein expression and characterization see FIGS. 21A-21F). The incorporation of azF did not affect the self-assembly of the protein into a homotrimer, and the purified protein was completely free from the aggregation seen in the E54C mutant (FIG. 24A). The E54(azF) ald$_3$ was reacted with a 21-nt DNA strand functionalized with a dibenzocyclooctyne (DBCO) moiety (FIG. 6B), isolated the (ald-DNA)$_3$ conjugate by anion exchange chromatography, and verified its complete conversion by SDS-PAGE (FIG. 6C). For details regarding the DNA-DBCO synthesis and characterization, conjugation to E54(azF) ald$_3$, and purification of the (ald-DNA)$_3$ conjugate, see FIGS. 24A-24B.

Upon annealing with 3t-Base, the E54(azF) (ald-DNA)$_3$ yielded a band with the same mobility as the original 3t-aldTet samples (FIG. 6E), and analysis of the purified band by AFM showed cages similar to those in FIG. 4C. The average height of these particles was 8.3 nm, and the average edge length was 11 nm (FIGS. 23A-23F). With the exception of the chemical linkage and minor differences in the linkers between the protein and DNA, the E54C and E54(azF) (ald-DNA)$_3$ conjugates are identical so it was not surprising that they would form highly similar three-dimensional hybrid cages. Modifying the attachment site of DNA should affect the angle of the dsDNA edges emanating from the protein, and might allow for the synthesis of cages with different sizes or symmetries as demonstrated using DNA hierarchical assembly.

A new mutant, E74(azF), was designed that positioned the reactive residues closer together on one surface of the trimer as opposed to the outer edge (FIG. 6A). This site would theoretically reduce the angle between the three edges of the cage and potentially lead to more efficient cage formation. The E74(azF) version of (ald-DNA)₃ was synthesized and purified similar to the E54(azF) conjugate. When annealed with 3t-Base, the E74(azF) mutant of (ald-DNA)₃ gave a higher-retention band by native PAGE, similar to the E54 (azF) mutant (FIG. 6D). The vast majority of isolated structures (~95%, FIG. 23B) were not well-formed, closed cages. Rather, the E74(azF) (ald-DNA)₃ primarily bound to a single arm of 3t-Base, resulting in open structures where both the trimer and the triangular base with two unbound arms are visible (FIG. 6F). A number of structures where the (ald-DNA)₃ has two arms attached to a single base, or one arm attached to each of two different bases, can also be seen. The upper bands in the gel are most likely protein with two 3t-Base structures bound, or oligomers of several proteins and DNA structures. The inefficiency in cage formation with the E74(azF) mutant is most likely due to the electrostatic repulsion incurred by trying to confine the three dsDNA arms in a small area, though entropic constraints imposed by the linkers cannot be ruled out. Overall, DNA-protein cage formation can be accomplished using a variety of chemical reactions, and that the conjugation site can be rationally moved around on the protein surface to influence the assembly of the final nanostructure.

Figure 24B:
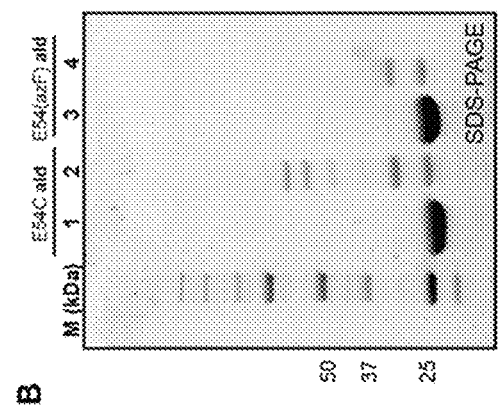

The Cys54 mutation leads to aggregation of (ald)₃ trimers due to disulfide formation, whereas 4-azidophenylalanine gives almost entirely monodisperse and non-aggregated trimers (FIG. 24A). To reverse the aggregation in the E54C samples and render C54 reactive for disulfide exchange with SPDP, the protein was treated with DTT prior to conjugation with DNA. However, the conditions had to be controlled carefully to obtain a satisfactory conversion: 25-30 minutes exposure to 40 mM DTT at 4° C. Longer incubation times resulted in reduction of the two internal disulfide bonds, which in turn yielded attachment of 1-4 more DNA strands (Figure S18B, lane 2). The E54(azF) mutant, by contrast, did not have any potential side reactions, even upon prolonged exposure to DNA-DBCO, and only showed a single modification (FIG. 24B, lane 4). Thus, using non-canonical amino acids in protein-DNA nanomaterials will simultaneously solve issues with aggregation and specificity compared with cysteine chemistry.

TABLE 1

Exemplary protein component sequences

| Protein Component | Amino Acid Sequence | SEQ ID NO: |
|---|---|---|
| ald (wild-type) | MKMEELFKKHKIVAVLRANSVEEAKEKALAVFEGGVHLIEITFTVPDA DTVIKELSFLKEKGAIIGAGTVTSVEQCRKAVESGAEFIVSPHLDEEISQ FCKEKGVFYMPGVMTPTELVKAMKLGHTILKLFPGEVVGPQFVKAMK GPFPNVKFVPTGGVNLDNVCEWFKAGVLAVGVGSALVKGTPDEVRE KAKAFVEKIRGCTE | 1 |
| ald E54C | MKMEELFKKHKIVAVLRANSVEEAKEKALAVFEGGVHLIEITFTVPDA DTVIKCLSFLKEKGAIIGAGTVTSVEQCRKAVESGAEFIVSPHLDEEISQ FCKEKGVFYMPGVMTPTELVKAMKLGHTILKLFPGEVVGPQFVKAMK GPFPNVKFVPTGGVNLDNVCEWFKAGVLAVGVGSALVKGTPDEVRE KAKAFVEKIRGCTE | 2 |
| ald E54(azF) | MKMEELFKKHKIVAVLRANSVEEAKEKALAVFEGGVHLIEITFTVPDA DTVIK(azF)LSFLKEKGAIIGAGTVTSVEQCRKAVESGAEFIVSPHLDEEI SQFCKEKGVFYMPGVMTPTELVKAMKLGHTILKLFPGEVVGPQFVKA MKGPFPNVKFVPTGGVNLDNVCEWFKAGVLAVGVGSALVKGTPDEV REKAKAFVEKIRGCTEGSENLYFQGSHHHHHH | 3 |
| ald E74(azF) | MKMEELFKKHKIVAVLRANSVEEAKEKALAVFEGGVHLIEITFTVPDA DTVIKELSFLKEKGAIIGAGTVTSV(azF)QCRKAVESGAEFIVSPHLDEEI SQFCKEKGVFYMPGVMTPTELVKAMKLGHTILKLFPGEVVGPQFVKA MKGPFPNVKFVPTGGVNLDNVCEWFKAGVLAVGVGSALVKGTPDEV REKAKAFVEKIRGCTEGSENLYFQGSHHHHHH | 4 |

TABLE 2

Plasmids

| Plasmid Name | Function |
|---|---|
| pEt28- kdgA | Expression of wild type aldolase |
| pEt28- kdgA (E54C) | Expression of aldolase with E54C mutation |
| pEt28- kdgA (E54AZF) | Expression of aldolase with E54(azF) |
| pEt28- kdgA (E74AZF) | Expression of aldolase with E74(azF) |
| pDule2 | Expression of 4-azidophenylalanine-tRNA synthetase |

TABLE 3

Primers

| Primer ID | Sequence | SEQ ID NO: | Description |
|---|---|---|---|
| Pbb1 F | 5' TAACTCGAGTCTGGTAAAGAAACCGCTGC 3' | 5 | Pet28 backbone For |
| Pbb1 R | 5'GAATTCACCTTGGAAATACAGATTCTCCGGATCC3' | 6 | Pet28 backbone Rev |
| Ins ald F | 5'CTGTATTTCCAAGGTGAATTCGCGGCCGCAATGAAGATGGAAGAGCTC 3' | 7 | Insert kdgA For |
| Ins ald R | 5'CAGCAGCGGTTTCTTTACCAGACTCGAGTTATTCTGTGCACCCCCTGAT 3' | 8 | Ins kdgA Rev |
| Ins C54 F | 5' CAGTCATCAAATGCCTCTCGTTCCTC 3' | 9 | Pet28 kdgA M54C For |
| Ins C54 R | 5' GAACGAGAGGCATTTGATGACTGTGTC 3' | 10 | Pet28 kdgA M54C Rev |
| Ins azf54 F | 5' AGTCATCAAATAGCTCTCGTTCCTCAAG 3' | 11 | Pet28 kdgA M54azf For |
| Ins azf54 R | 5' GTGTCAGCGTCTGGAACA 3' | 12 | Pet28 kdgA M54azf Rev |
| Ins azf74 F | 5' GACGAGTGTCTAGCAGTGCAGAAAAG 3' | 13 | Pet28 kdgA M74azf For |
| Ins azf74 R | 5' ACTGTACCTGCACCTATTATG 3' | 14 | Pet28 kdgA M74azf Rev |

We claim:

1. A three-dimensional nanocage comprising:
   a protein covalently linked to a polynucleotide handle, wherein the protein is a homotrimer;
   wherein the polynucleotide handle is covalently linked to a solvent exposed cysteine by a disulfide linkage or
   wherein the polynucleotide handle is covalently linked to a surface 4-azidophenylalanine residue; and
   wherein the polynucleotide handle is at least 15 base pairs long; and
   a DNA assembly comprising a polynucleotide arm complementary to the polynucleotide handle linked to the protein, wherein the polynucleotide handle and the polynucleotide arm form a double-stranded complex linked to the protein to the DNA assembly; and
   wherein the DNA assembly comprises 4 oligonucleotides.

2. The nanocage of claim 1, wherein the protein is a multimeric protein.

3. The nanocage of claim 1, wherein each monomer of the multimeric protein is covalently linked to a polynucleotide handle.

4. The nanocage of claim 1, wherein the DNA assembly comprises at least 5 oligonucleotides.

5. The nanocage of claim 1, additionally comprising a payload molecule.

6. The nanocage of claim 5, wherein the payload molecule is selected from the group consisting of a nucleic acid, a polypeptide, a protein, an enzyme, an antibody, a phospholipid, a carbohydrate, and a polysaccharide.

\* \* \* \* \*

SEQUENCE LISTING

<160> NUMBER OF SEQ ID NOS: 48

<210> SEQ ID NO 1
<211> LENGTH: 205
<212> TYPE: PRT
<213> ORGANISM: Thermotoga maritima

<400> SEQUENCE: 1

```
Met Lys Met Glu Glu Leu Phe Lys Lys His Lys Ile Val Ala Val Leu
1               5                   10                  15

Arg Ala Asn Ser Val Glu Glu Ala Lys Glu Lys Ala Leu Ala Val Phe
                20                  25                  30

Glu Gly Gly Val His Leu Ile Glu Ile Thr Phe Thr Val Pro Asp Ala
            35                  40                  45

Asp Thr Val Ile Lys Glu Leu Ser Phe Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
```

```
                    145                 150                 155                 160
Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu
        195                 200                 205

<210> SEQ ID NO 2
<211> LENGTH: 205
<212> TYPE: PRT
<213> ORGANISM: Artificial Sequence
<220> FEATURE:
<223> OTHER INFORMATION: Synthetic- ald E54C

<400> SEQUENCE: 2

Met Lys Met Glu Glu Leu Phe Lys Lys His Lys Ile Val Ala Val Leu
1               5                   10                  15

Arg Ala Asn Ser Val Glu Glu Ala Lys Glu Lys Ala Leu Ala Val Phe
            20                  25                  30

Glu Gly Gly Val His Leu Ile Glu Ile Thr Phe Thr Val Pro Asp Ala
        35                  40                  45

Asp Thr Val Ile Lys Cys Leu Ser Phe Leu Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu
        195                 200                 205

<210> SEQ ID NO 3
<211> LENGTH: 221
<212> TYPE: PRT
<213> ORGANISM: Artificial Sequence
<220> FEATURE:
<223> OTHER INFORMATION: Synthetic- ald E54(azF)
<220> FEATURE:
<221> NAME/KEY: MISC_FEATURE
<222> LOCATION: (54)..(54)
<223> OTHER INFORMATION: X is the non-canonical amino acid
      4-azidophenylalanine (azF)

<400> SEQUENCE: 3

Met Lys Met Glu Glu Leu Phe Lys Lys His Lys Ile Val Ala Val Leu
1               5                   10                  15

Arg Ala Asn Ser Val Glu Glu Ala Lys Glu Lys Ala Leu Ala Val Phe
```

```
            20                  25                  30
Glu Gly Gly Val His Leu Ile Glu Ile Thr Phe Thr Val Pro Asp Ala
        35                  40                  45

Asp Thr Val Ile Lys Xaa Leu Ser Phe Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu Gly Ser Glu
        195                 200                 205

Asn Leu Tyr Phe Gln Gly Ser His His His His His His
    210                 215                 220

<210> SEQ ID NO 4
<211> LENGTH: 221
<212> TYPE: PRT
<213> ORGANISM: Artificial Sequence
<220> FEATURE:
<223> OTHER INFORMATION: Synthetic- ald E74(azF)
<220> FEATURE:
<221> NAME/KEY: MISC_FEATURE
<222> LOCATION: (74)..(74)
<223> OTHER INFORMATION: X is the non-canonical amino acid
      4-azidophenylalanine (azF)

<400> SEQUENCE: 4

Met Lys Met Glu Glu Leu Phe Lys Lys His Lys Ile Val Ala Val Leu
1               5                   10                  15

Arg Ala Asn Ser Val Glu Glu Ala Lys Glu Lys Ala Leu Ala Val Phe
            20                  25                  30

Glu Gly Gly Val His Leu Ile Glu Ile Thr Phe Thr Val Pro Asp Ala
        35                  40                  45

Asp Thr Val Ile Lys Glu Leu Ser Phe Leu Lys Glu Lys Gly Ala Ile
    50                  55                  60

Ile Gly Ala Gly Thr Val Thr Ser Val Xaa Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140
```

```
Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu Gly Ser Glu
        195                 200                 205

Asn Leu Tyr Phe Gln Gly Ser His His His His His His
    210                 215                 220

<210> SEQ ID NO 5
<211> LENGTH: 29
<212> TYPE: DNA
<213> ORGANISM: Artificial Sequence
<220> FEATURE:
<223> OTHER INFORMATION: Synthetic- Pbb1 F primer

<400> SEQUENCE: 5
taactcgagt ctggtaaaga aaccgctgc                                        29

<210> SEQ ID NO 6
<211> LENGTH: 34
<212> TYPE: DNA
<213> ORGANISM: Artificial Sequence
<220> FEATURE:
<223> OTHER INFORMATION: Synthetic- Pbb1 R primer

<400> SEQUENCE: 6
gaattcacct tggaaataca gattctccgg atcc                                  34

<210> SEQ ID NO 7
<211> LENGTH: 48
<212> TYPE: DNA
<213> ORGANISM: Artificial Sequence
<220> FEATURE:
<223> OTHER INFORMATION: Synthetic- Ins ald F primer

<400> SEQUENCE: 7
ctgtatttcc aaggtgaatt cgcggccgca atgaagatgg aagagctc                   48

<210> SEQ ID NO 8
<211> LENGTH: 49
<212> TYPE: DNA
<213> ORGANISM: Artificial Sequence
<220> FEATURE:
<223> OTHER INFORMATION: Synthetic- Ins ald R primer

<400> SEQUENCE: 8
cagcagcggt ttctttacca gactcgagtt attctgtgca ccccctgat                  49

<210> SEQ ID NO 9
<211> LENGTH: 26
<212> TYPE: DNA
<213> ORGANISM: Artificial Sequence
<220> FEATURE:
<223> OTHER INFORMATION: Synthetic- Ins C54 F primer

<400> SEQUENCE: 9
cagtcatcaa atgcctctcg ttcctc                                           26

<210> SEQ ID NO 10
<211> LENGTH: 27
```

```
<212> TYPE: DNA
<213> ORGANISM: Artificial Sequence
<220> FEATURE:
<223> OTHER INFORMATION: Synthetic- Ins C54 R primer

<400> SEQUENCE: 10
gaacgagagg catttgatga ctgtgtc                                        27

<210> SEQ ID NO 11
<211> LENGTH: 28
<212> TYPE: DNA
<213> ORGANISM: Artificial Sequence
<220> FEATURE:
<223> OTHER INFORMATION: Synthetic- Ins azf54 F primer

<400> SEQUENCE: 11
agtcatcaaa tagctctcgt tcctcaag                                       28

<210> SEQ ID NO 12
<211> LENGTH: 18
<212> TYPE: DNA
<213> ORGANISM: Artificial Sequence
<220> FEATURE:
<223> OTHER INFORMATION: Synthetic- Ins azf54 R primer

<400> SEQUENCE: 12
gtgtcagcgt ctggaaca                                                  18

<210> SEQ ID NO 13
<211> LENGTH: 26
<212> TYPE: DNA
<213> ORGANISM: Artificial Sequence
<220> FEATURE:
<223> OTHER INFORMATION: Synthetic- Ins azf74 F primer

<400> SEQUENCE: 13
gacgagtgtc tagcagtgca gaaaag                                         26

<210> SEQ ID NO 14
<211> LENGTH: 21
<212> TYPE: DNA
<213> ORGANISM: Artificial Sequence
<220> FEATURE:
<223> OTHER INFORMATION: Synthetic- Ins azf74 R primer

<400> SEQUENCE: 14
actgtacctg cacctattat g                                              21

<210> SEQ ID NO 15
<211> LENGTH: 44
<212> TYPE: DNA
<213> ORGANISM: Artificial Sequence
<220> FEATURE:
<223> OTHER INFORMATION: Synthetic- S211 staple strand

<400> SEQUENCE: 15
tttacgaggc ccaatagcaa gcagagcaga cctgacggaa ctca                     44

<210> SEQ ID NO 16
<211> LENGTH: 44
<212> TYPE: DNA
<213> ORGANISM: Artificial Sequence
<220> FEATURE:
<223> OTHER INFORMATION: Synthetic- S212 staple strand

<400> SEQUENCE: 16
```
gcctttacgc cagttacaaa atagagcaga cctgacggaa ctca                44

<210> SEQ ID NO 17
<211> LENGTH: 44
<212> TYPE: DNA
<213> ORGANISM: Artificial Sequence
<220> FEATURE:
<223> OTHER INFORMATION: Synthetic- S213 staple strand

<400> SEQUENCE: 17
gttaagccag ccttaaatca agagagcaga cctgacggaa ctca                44

<210> SEQ ID NO 18
<211> LENGTH: 100
<212> TYPE: DNA
<213> ORGANISM: Artificial Sequence
<220> FEATURE:
<223> OTHER INFORMATION: Synthetic- T1 multi-crossover ("MX") tile DNA
      strand

<400> SEQUENCE: 18
gagcagacct agcggacttg ggtaaaccgt ataaaggcta tgttgcactc acggaccgat    60
gctcctcacc acttcagttg ggcaacggcc taagggcttg                        100

<210> SEQ ID NO 19
<211> LENGTH: 20
<212> TYPE: DNA
<213> ORGANISM: Artificial Sequence
<220> FEATURE:
<223> OTHER INFORMATION: Synthetic- T2 multi-crossover ("MX") tile DNA
      strand

<400> SEQUENCE: 19
gagttccgtc aggtctgctc                                              20

<210> SEQ ID NO 20
<211> LENGTH: 42
<212> TYPE: DNA
<213> ORGANISM: Artificial Sequence
<220> FEATURE:
<223> OTHER INFORMATION: Synthetic- T3 multi-crossover ("MX") tile DNA
      strand

<400> SEQUENCE: 20
caagtccgct cggcatctgg gtcccataag gtacggttta cc                     42

<210> SEQ ID NO 21
<211> LENGTH: 42
<212> TYPE: DNA
<213> ORGANISM: Artificial Sequence
<220> FEATURE:
<223> OTHER INFORMATION: Synthetic- T4 multi-crossover ("MX") tile DNA
      strand

<400> SEQUENCE: 21
agacgggcga gtgagtgcaa catagccttt aagcacacca gg                     42

<210> SEQ ID NO 22
<211> LENGTH: 42
<212> TYPE: DNA
<213> ORGANISM: Artificial Sequence
<220> FEATURE:
<223> OTHER INFORMATION: Synthetic- T5 multi-crossover ("MX") tile DNA
      strand

<400> SEQUENCE: 22

```
gcatcggtcc cgagctaaca acgcggaacc tagtggtgag ga                    42
```

<210> SEQ ID NO 23
<211> LENGTH: 42
<212> TYPE: DNA
<213> ORGANISM: Artificial Sequence
<220> FEATURE:
<223> OTHER INFORMATION: Synthetic- T6 multi-crossover ("MX") tile DNA
      strand

<400> SEQUENCE: 23

```
gtatatgctc cttaggccgt tgcccaactg atcagagagg gt                    42
```

<210> SEQ ID NO 24
<211> LENGTH: 20
<212> TYPE: DNA
<213> ORGANISM: Artificial Sequence
<220> FEATURE:
<223> OTHER INFORMATION: Synthetic- T7 multi-crossover ("MX") tile DNA
      strand

<400> SEQUENCE: 24

```
ttttcaagcc cggagctttt                                             20
```

<210> SEQ ID NO 25
<211> LENGTH: 100
<212> TYPE: DNA
<213> ORGANISM: Artificial Sequence
<220> FEATURE:
<223> OTHER INFORMATION: Synthetic- T8 multi-crossover ("MX") tile DNA
      strand

<400> SEQUENCE: 25

```
gctccggagc atatacaccc tctctgaagg ttccgcgttg ttagctcgtc gcccgtctcc    60
tggtgtgctc cttatgggac ccagatgccg gacggaactc                          100
```

<210> SEQ ID NO 26
<211> LENGTH: 77
<212> TYPE: DNA
<213> ORGANISM: Artificial Sequence
<220> FEATURE:
<223> OTHER INFORMATION: Synthetic- T3S2 Strand for 3t-Base (three-turn
      triangular base)

<400> SEQUENCE: 26

```
tagatgatag ctagatagta gatagtagaa gagatagata gatatgcgat cgatcggagc    60
agacctgacg gaactca                                                   77
```

<210> SEQ ID NO 27
<211> LENGTH: 77
<212> TYPE: DNA
<213> ORGANISM: Artificial Sequence
<220> FEATURE:
<223> OTHER INFORMATION: Synthetic- T3S3 Strand for 3t-Base (three-turn
      triangular base)

<400> SEQUENCE: 27

```
cgatcgatcg ctatagatag tagatagatg atagatgaga tgagtcgatc gtagctgagc    60
agacctgacg gaactca                                                   77
```

<210> SEQ ID NO 28
<211> LENGTH: 77
<212> TYPE: DNA
<213> ORGANISM: Artificial Sequence
<220> FEATURE:

<223> OTHER INFORMATION: Synthetic- T3S4 Strand for 3t-Base (three-turn triangular base)

<400> SEQUENCE: 28
agctacgatc gttagataga tgagagagaa gatagagaga taagtgctat catctagagc    60
agacctgacg gaactca                                                   77

<210> SEQ ID NO 29
<211> LENGTH: 99
<212> TYPE: DNA
<213> ORGANISM: Artificial Sequence
<220> FEATURE:
<223> OTHER INFORMATION: Synthetic- T3S5 Strand for 3t-Base (three-turn triangular base)

<400> SEQUENCE: 29
ctactatcta ctatctactt atctctctat cttctctctc atctatctat ctcatctcat    60
ctatcatcta tctactatct atctatctat ctatctctt                           99

<210> SEQ ID NO 30
<211> LENGTH: 32
<212> TYPE: DNA
<213> ORGANISM: Artificial Sequence
<220> FEATURE:
<223> OTHER INFORMATION: Synthetic- TC3S1 Strand for 3t-Tet (three-turn all-DNA tetrahedron)

<400> SEQUENCE: 30
gtctgaggca gttgagagat ctcgaacatt cc                                  32

<210> SEQ ID NO 31
<211> LENGTH: 61
<212> TYPE: DNA
<213> ORGANISM: Artificial Sequence
<220> FEATURE:
<223> OTHER INFORMATION: Synthetic- TC3S2 Strand for 3t-Tet (three-turn all-DNA tetrahedron)

<400> SEQUENCE: 31
taagtctgaa gatccattta tcaccagctg ctgcacgcca tagtagacgt atcacctgtc    60
c                                                                    61

<210> SEQ ID NO 32
<211> LENGTH: 61
<212> TYPE: DNA
<213> ORGANISM: Artificial Sequence
<220> FEATURE:
<223> OTHER INFORMATION: Synthetic- TC3S3 Strand for 3t-Tet (three-turn all-DNA tetrahedron)

<400> SEQUENCE: 32
cagctggtga taaaacgtgt agcaagtagc tttgatctgt aatcgactct acgggaagag    60
c                                                                    61

<210> SEQ ID NO 33
<211> LENGTH: 61
<212> TYPE: DNA
<213> ORGANISM: Artificial Sequence
<220> FEATURE:
<223> OTHER INFORMATION: Synthetic- TC3S4 Strand for 3t-Tet (three-turn all-DNA tetrahedron)

<400> SEQUENCE: 33
cagctggtga taaaacgtgt agcaagtagc tttgatctgt aatcgactct acgggaagag    60

<210> SEQ ID NO 34
<211> LENGTH: 32
<212> TYPE: DNA
<213> ORGANISM: Artificial Sequence
<220> FEATURE:
<223> OTHER INFORMATION: Synthetic- TC3S5 Strand for 3t-Tet (three-turn all-DNA tetrahedron)

<400> SEQUENCE: 34
atgcccatcc ggctcactac tatggcgtgc ag                         32

<210> SEQ ID NO 35
<211> LENGTH: 93
<212> TYPE: DNA
<213> ORGANISM: Artificial Sequence
<220> FEATURE:
<223> OTHER INFORMATION: Synthetic- TC3S6 Strand for 3t-Tet (three-turn all-DNA tetrahedron)

<400> SEQUENCE: 35
cgagtcctcg catgactcaa ctgcctcaga cggacaggtg atacgagagc cggatgggca     60
tgctcttccc gtagagatag tacggtattg gac                                 93

<210> SEQ ID NO 36
<211> LENGTH: 111
<212> TYPE: DNA
<213> ORGANISM: Artificial Sequence
<220> FEATURE:
<223> OTHER INFORMATION: Synthetic- T4S2 Strand for 4t-Base (four-turn triangular base)

<400> SEQUENCE: 36
gagcagacct gacggaactc aaggagtgtg atggagattt attttgagag agaagataga     60
gagataagag atagatagat agatagattt tccgtgtagt gttcaacgcc t             111

<210> SEQ ID NO 37
<211> LENGTH: 129
<212> TYPE: DNA
<213> ORGANISM: Artificial Sequence
<220> FEATURE:
<223> OTHER INFORMATION: Synthetic- T4S3 Strand for 4t-Base (four-turn triangular base)

<400> SEQUENCE: 37
atctctctat cttctctctc ttactatcta ctatctactt atctctctat cttctctctc     60
atctctcatc tcatctatca tctatctact atctatctat ctattcttct atctatctat    120
ctatctctt                                                            129

<210> SEQ ID NO 38
<211> LENGTH: 111
<212> TYPE: DNA
<213> ORGANISM: Artificial Sequence
<220> FEATURE:
<223> OTHER INFORMATION: Synthetic- T4S4 Strand for 4t-Base (four-turn triangular base)

<400> SEQUENCE: 38
gagcagacct gacggaactc aaggcgttga acactacacg gatttgaata gatagataga     60
tagtagatag atgatagatg agatgagttt ctctcgtagt taacatctag c             111

```
<210> SEQ ID NO 39
<211> LENGTH: 111
<212> TYPE: DNA
<213> ORGANISM: Artificial Sequence
<220> FEATURE:
<223> OTHER INFORMATION: Synthetic- T4S5 Strand for 4t-Base (four-turn
      triangular base)

<400> SEQUENCE: 39
gagcagacct gacggaactc agctagatgt taactacgag agtttgatga gagagaagat      60
agagagataa gtagatagta gatagtattt ataaatctcc atcacactcc t             111

<210> SEQ ID NO 40
<211> LENGTH: 122
<212> TYPE: DNA
<213> ORGANISM: Artificial Sequence
<220> FEATURE:
<223> OTHER INFORMATION: Synthetic- TC4S1 Strand for 4t-Tet (four-turn
      all-DNA tetrahedron)

<400> SEQUENCE: 40
catcacatta ccattaccta ctcattaccc ttacatccaa catcattcac atctatacct      60
acactaacct tacctacatt acctatcact accactctcc tcattaccta acctacatcc    120
ac                                                                   122

<210> SEQ ID NO 41
<211> LENGTH: 82
<212> TYPE: DNA
<213> ORGANISM: Artificial Sequence
<220> FEATURE:
<223> OTHER INFORMATION: Synthetic- TC4S2 Strand for 4t-Tet (four-turn
      all-DNA tetrahedron)

<400> SEQUENCE: 41
aatgtaggta aggttagtgt tgacgacgga gaggttctta atacttcaag tgaaatgttt      60
ttttaaacag gtttggtagg tg                                              82

<210> SEQ ID NO 42
<211> LENGTH: 41
<212> TYPE: DNA
<213> ORGANISM: Artificial Sequence
<220> FEATURE:
<223> OTHER INFORMATION: Synthetic- TC4S3 Strand for 4t-Tet (four-turn
      all-DNA tetrahedron)

<400> SEQUENCE: 42
cacggactct gtcgtataca tggagagtgg tagtgatagg t                         41

<210> SEQ ID NO 43
<211> LENGTH: 123
<212> TYPE: DNA
<213> ORGANISM: Artificial Sequence
<220> FEATURE:
<223> OTHER INFORMATION: Synthetic- TC4S4 Strand for 4t-Tet (four-turn
      all-DNA tetrahedron)

<400> SEQUENCE: 43
gactggagtg taatcgctag tggtaatggt aatgtgatga gtggatgtag gttaggtaat      60
gttgtatacg acagagtccg tgcacctacc aaacctgttt aatatagcga acgattataa    120
tga                                                                  123

<210> SEQ ID NO 44
<211> LENGTH: 82
```

```
<212> TYPE: DNA
<213> ORGANISM: Artificial Sequence
<220> FEATURE:
<223> OTHER INFORMATION: Synthetic- TC4S5 Strand for 4t-Tet (four-turn
      all-DNA tetrahedron)

<400> SEQUENCE: 44
tggatgtaag ggtaatgagt tctagcgatt acactccagt ctcattataa tcgttcgcta        60
ttaaaacatt tcacttgaag ta                                                 82

<210> SEQ ID NO 45
<211> LENGTH: 41
<212> TYPE: DNA
<213> ORGANISM: Artificial Sequence
<220> FEATURE:
<223> OTHER INFORMATION: Synthetic- TC4S6 Strand for 4t-Tet (four-turn
      all-DNA tetrahedron)

<400> SEQUENCE: 45
ttaagaacct ctccgtcgtc tggtatagat gtgaatgatg t                            41

<210> SEQ ID NO 46
<211> LENGTH: 21
<212> TYPE: DNA
<213> ORGANISM: Artificial Sequence
<220> FEATURE:
<223> OTHER INFORMATION: Synthetic- 5'-amine-modified DNA oligo (with 5'
      Amino Modifier C6)

<400> SEQUENCE: 46
tgagttccgt caggtctgct c                                                  21

<210> SEQ ID NO 47
<211> LENGTH: 21
<212> TYPE: DNA
<213> ORGANISM: Artificial Sequence
<220> FEATURE:
<223> OTHER INFORMATION: Synthetic- (A)21

<400> SEQUENCE: 47
aaaaaaaaaa aaaaaaaaaa a                                                  21

<210> SEQ ID NO 48
<211> LENGTH: 21
<212> TYPE: DNA
<213> ORGANISM: Artificial Sequence
<220> FEATURE:
<223> OTHER INFORMATION: Synthetic- (T)21

<400> SEQUENCE: 48
tttttttttt tttttttttt t                                                  21
```